(12) United States Patent
Markle et al.

(10) Patent No.: US 8,838,195 B2
(45) Date of Patent: Sep. 16, 2014

(54) OPTICAL SYSTEMS AND METHODS FOR RATIOMETRIC MEASUREMENT OF BLOOD GLUCOSE CONCENTRATION

(75) Inventors: David R. Markle, Berwyn, PA (US); Ritchie A. Wessling, Watsonville, CA (US); Donald J. Kolehmainen, Laguna Niguel, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1873 days.

(21) Appl. No.: 12/027,158

(22) Filed: Feb. 6, 2008

(65) Prior Publication Data

US 2008/0188725 A1 Aug. 7, 2008

Related U.S. Application Data

(60) Provisional application No. 60/888,477, filed on Feb. 6, 2007.

(51) Int. Cl.
*A61B 5/1455* (2006.01)
*G01N 21/64* (2006.01)
*A61B 5/1459* (2006.01)
*A61B 5/145* (2006.01)

(52) U.S. Cl.
CPC .......... *A61B 5/1459* (2013.01); *G01N 21/6428* (2013.01); *G01N 21/645* (2013.01); *A61B 5/14532* (2013.01)
USPC ............ 600/316; 600/310; 600/322; 600/344

(58) Field of Classification Search
USPC ................................. 600/309–344
See application file for complete search history.

(56) References Cited

U.S. PATENT DOCUMENTS

| | | | |
|---|---|---|---|
| 1,120,700 A | 12/1914 | Ehrlich |
| 1,334,901 A | 3/1920 | Higdon |
| 2,018,792 A | 10/1935 | Kern |
| 2,094,224 A | 9/1937 | Tietz et al. |
| 2,112,244 A | 3/1938 | Jurist |
| 2,274,551 A | 2/1942 | Kenyon et al. |
| 2,496,151 A | 1/1950 | Dawson et al. |
| 2,812,524 A | 11/1957 | Pruitt |
| 3,011,293 A | 12/1961 | Rado |
| 3,302,219 A | 2/1967 | Harris |
| 3,488,098 A | 1/1970 | Sobczak |

(Continued)

FOREIGN PATENT DOCUMENTS

| | | |
|---|---|---|
| CN | 85108331 | 6/1987 |
| CS | 7707425 | 2/1980 |

(Continued)

OTHER PUBLICATIONS

"Optical Glucose Sensor Holds Promise for Diabetics and Intensive Care Patients," in ScienceDaily, Mar. 18, 2004.

(Continued)

*Primary Examiner* — Eric Winakur
*Assistant Examiner* — Marjan Fardanesh
(74) *Attorney, Agent, or Firm* — Medtronic MiniMed, Inc.

(57) ABSTRACT

Novel optical devices, methods and systems relating to the detection of glucose, and more particularly to real-time glucose monitoring, are disclosed herein. More particularly, various hardware and methodological means are disclosed for ratiometric correction of optical glucose measurements for artifacts of optical systems.

28 Claims, 20 Drawing Sheets

(56) References Cited

U.S. PATENT DOCUMENTS

| | | |
|---|---|---|
| 3,659,586 A | 5/1972 | Johns et al. |
| 3,685,059 A | 8/1972 | Bokros et al. |
| 3,795,239 A | 3/1974 | Eberhard et al. |
| 3,827,089 A | 8/1974 | Grow |
| 3,865,548 A | 2/1975 | Padawer |
| 3,874,010 A | 4/1975 | Geary |
| 3,884,225 A | 5/1975 | Witter |
| 3,895,403 A | 7/1975 | Davis |
| 3,905,888 A | 9/1975 | Mindt et al. |
| 3,909,504 A | 9/1975 | Browne |
| 3,924,281 A | 12/1975 | Gibbs |
| 3,930,580 A | 1/1976 | Bazell et al. |
| 3,996,345 A | 12/1976 | Ullman |
| 4,003,707 A | 1/1977 | Lübbers et al. |
| 4,041,932 A | 8/1977 | Fostick |
| 4,094,578 A | 6/1978 | DiVita et al. |
| 4,118,485 A | 10/1978 | Eriksson et al. |
| 4,180,879 A | 1/1980 | Mann |
| 4,197,853 A | 4/1980 | Parker |
| 4,200,110 A | 4/1980 | Peterson et al. |
| 4,240,438 A | 12/1980 | Updike et al. |
| 4,245,645 A | 1/1981 | Arseneault et al. |
| 4,269,605 A | 5/1981 | Dean et al. |
| 4,306,562 A | 12/1981 | Osborne |
| 4,307,933 A | 12/1981 | Palmer et al. |
| 4,308,254 A | 12/1981 | Tayot et al. |
| 4,344,438 A | 8/1982 | Schultz |
| 4,345,606 A | 8/1982 | Littleford |
| 4,358,851 A | 11/1982 | Scilfres et al. |
| 4,361,918 A | 12/1982 | Roisseth |
| 4,371,374 A | 2/1983 | Cerami et al. |
| 4,459,712 A | 7/1984 | Pathan |
| 4,465,335 A | 8/1984 | Eppes |
| 4,469,357 A | 9/1984 | Martin |
| 4,474,431 A | 10/1984 | Bricheno |
| 4,476,870 A | 10/1984 | Peterson et al. |
| 4,490,867 A | 1/1985 | Gabrielsson |
| 4,495,293 A | 1/1985 | Shaffar |
| 4,502,169 A | 3/1985 | Persson |
| RE31,879 E | 5/1985 | Lübbers et al. |
| 4,528,616 A | 7/1985 | Koppensteiner |
| 4,548,907 A | 10/1985 | Seitz et al. |
| 4,557,900 A | 12/1985 | Heitzmann |
| 4,560,248 A | 12/1985 | Cramp et al. |
| 4,568,444 A | 2/1986 | Nakamura et al. |
| 4,579,641 A | 4/1986 | Shimomura et al. |
| 4,600,310 A | 7/1986 | Cramp et al. |
| 4,621,049 A | 11/1986 | Wang |
| 4,629,451 A | 12/1986 | Winters et al. |
| 4,636,144 A | 1/1987 | Abe et al. |
| 4,649,271 A | 3/1987 | Hök et al. |
| 4,650,472 A | 3/1987 | Bates |
| 4,654,031 A | 3/1987 | Lentz |
| 4,654,127 A | 3/1987 | Baker et al. |
| 4,659,817 A | 4/1987 | Gallop et al. |
| 4,675,925 A | 6/1987 | Littleton |
| 4,684,538 A | 8/1987 | Klemarczyk |
| 4,689,308 A | 8/1987 | Gerhard |
| RE32,514 E | 10/1987 | Steklenski |
| 4,703,756 A | 11/1987 | Gough et al. |
| 4,707,056 A | 11/1987 | Bittner |
| 4,710,623 A | 12/1987 | Lipson et al. |
| 4,727,730 A | 3/1988 | Boiarski et al. |
| 4,737,153 A | 4/1988 | Shimamura et al. |
| 4,744,618 A | 5/1988 | Mahlein |
| 4,746,751 A | 5/1988 | Oviatt |
| 4,750,795 A | 6/1988 | Blotekjaer |
| 4,751,918 A | 6/1988 | Bernard et al. |
| 4,754,538 A | 7/1988 | Stewart, Jr. et al. |
| 4,776,047 A | 10/1988 | DiMatteo |
| 4,785,814 A | 11/1988 | Kane |
| 4,792,689 A | 12/1988 | Peterson |
| 4,794,619 A | 12/1988 | Tregay |
| 4,796,633 A | 1/1989 | Zwirkoski |
| 4,798,738 A | 1/1989 | Yafuso et al. |
| 4,801,187 A | 1/1989 | Elbert et al. |
| 4,803,049 A | 2/1989 | Hirschfeld et al. |
| 4,810,655 A | 3/1989 | Khalil et al. |
| 4,816,130 A | 3/1989 | Karakelle et al. |
| 4,820,636 A | 4/1989 | Hill et al. |
| 4,821,738 A | 4/1989 | Iwasaki et al. |
| 4,822,127 A | 4/1989 | Kamiya et al. |
| 4,833,091 A | 5/1989 | Leader et al. |
| 4,838,269 A | 6/1989 | Robinson et al. |
| 4,844,841 A | 7/1989 | Koller et al. |
| 4,846,543 A | 7/1989 | Kapany et al. |
| 4,851,195 A | 7/1989 | Matthews et al. |
| 4,854,321 A | 8/1989 | Boiarski |
| 4,861,728 A | 8/1989 | Wagner |
| 4,872,226 A | 10/1989 | Lonardo |
| 4,872,759 A | 10/1989 | Stich-Baumeister |
| 4,886,338 A | 12/1989 | Yafuso et al. |
| 4,889,407 A | 12/1989 | Markle |
| 4,903,707 A | 2/1990 | Knute et al. |
| 4,906,232 A | 3/1990 | Reynolds |
| 4,923,273 A | 5/1990 | Taylor |
| 4,927,222 A | 5/1990 | Kamiya et al. |
| 4,937,901 A | 7/1990 | Brennan |
| 4,939,801 A | 7/1990 | Schaal et al. |
| 4,941,308 A | 7/1990 | Grabenkort et al. |
| 4,943,364 A | 7/1990 | Koch et al. |
| 4,946,038 A | 8/1990 | Eaton |
| 4,955,862 A | 9/1990 | Sepetka |
| 4,960,412 A | 10/1990 | Fink |
| 4,966,597 A | 10/1990 | Cosman |
| 5,000,901 A | 3/1991 | Iyer et al. |
| 5,005,576 A | 4/1991 | Günther |
| 5,007,704 A | 4/1991 | McCartney |
| 5,012,809 A | 5/1991 | Shulze |
| 5,018,225 A | 5/1991 | Fergni et al. |
| 5,030,420 A | 7/1991 | Bacon |
| 5,047,208 A | 9/1991 | Schweitzer et al. |
| 5,047,627 A | 9/1991 | Yim et al. |
| 5,054,497 A | 10/1991 | Kapp et al. |
| 5,068,931 A | 12/1991 | Smith |
| 5,069,674 A | 12/1991 | Fearnot et al. |
| 5,082,112 A | 1/1992 | Dunklee |
| 5,093,266 A | 3/1992 | Leader et al. |
| 5,098,618 A | 3/1992 | Zelez |
| 5,104,388 A | 4/1992 | Quackenbush |
| 5,108,502 A | 4/1992 | Pawlowski et al. |
| 5,109,452 A | 4/1992 | Selvin et al. |
| 5,114,676 A | 5/1992 | Leiner et al. |
| 5,119,463 A | 6/1992 | Vurek |
| 5,132,432 A | 7/1992 | Haugland et al. |
| 5,137,833 A | 8/1992 | Russell |
| 5,141,497 A | 8/1992 | Erskine |
| 5,156,962 A | 10/1992 | Suzuki et al. |
| 5,162,130 A | 11/1992 | McLaughlin |
| 5,166,990 A | 11/1992 | Riccitelli et al. |
| 5,167,715 A | 12/1992 | Kalafala et al. |
| 5,168,587 A | 12/1992 | Shutes |
| 5,175,016 A | 12/1992 | Yafuso et al. |
| 5,176,882 A | 1/1993 | Gray et al. |
| 5,178,267 A | 1/1993 | Grabenkort et al. |
| 5,180,376 A | 1/1993 | Fischell |
| 5,182,353 A | 1/1993 | Hui et al. |
| 5,185,263 A | 2/1993 | Kroneis et al. |
| 5,188,803 A | 2/1993 | Hochberg |
| 5,217,691 A | 6/1993 | Greene et al. |
| 5,230,031 A | 7/1993 | Markle |
| 5,246,109 A | 9/1993 | Markle et al. |
| 5,246,441 A | 9/1993 | Ross et al. |
| 5,257,338 A | 10/1993 | Markle |
| 5,262,037 A | 11/1993 | Markle et al. |
| 5,279,596 A | 1/1994 | Castaneda et al. |
| 5,280,130 A | 1/1994 | Markle et al. |
| 5,280,548 A | 1/1994 | Atwater et al. |
| 5,286,294 A | 2/1994 | Ebi et al. |
| 5,290,266 A | 3/1994 | Rohling et al. |
| 5,302,731 A | 4/1994 | Pitner et al. |
| 5,305,740 A | 4/1994 | Kolobow |
| 5,310,471 A | 5/1994 | Markle et al. |
| 5,312,344 A | 5/1994 | Grinfeld |

(56) References Cited

U.S. PATENT DOCUMENTS

| | | | |
|---|---|---|---|
| 5,322,513 A | 6/1994 | Walker |
| 5,330,718 A | 7/1994 | Hui et al. |
| 5,334,157 A | 8/1994 | Klein et al. |
| 5,354,448 A | 10/1994 | Markle et al. |
| 5,357,732 A | 10/1994 | Markle et al. |
| 5,361,758 A | 11/1994 | Hall et al. |
| 5,380,304 A | 1/1995 | Parker |
| 5,389,217 A | 2/1995 | Singer |
| 5,409,469 A | 4/1995 | Schaerf |
| 5,503,770 A | 4/1996 | James et al. |
| 5,511,408 A | 4/1996 | Yoshioka et al. |
| 5,511,547 A | 4/1996 | Markle et al. |
| 5,512,246 A | 4/1996 | Russell et al. |
| 5,514,710 A | 5/1996 | Haugland et al. |
| 5,536,783 A | 7/1996 | Olstein et al. |
| 5,545,179 A | 8/1996 | Williamson, IV |
| 5,558,714 A | 9/1996 | Watanabe et al. |
| 5,569,186 A | 10/1996 | Lord et al. |
| 5,578,818 A * | 11/1996 | Kain et al. ............... 250/234 |
| 5,596,988 A | 1/1997 | Markle et al. |
| 5,605,152 A | 2/1997 | Slate et al. |
| 5,618,587 A | 4/1997 | Markle et al. |
| 5,622,259 A | 4/1997 | Church |
| 5,634,911 A | 6/1997 | Hermann et al. |
| 5,643,212 A | 7/1997 | Coutre et al. |
| 5,658,264 A | 8/1997 | Samson |
| 5,669,920 A | 9/1997 | Conley et al. |
| 5,676,784 A | 10/1997 | McGaffigan |
| D388,418 S | 12/1997 | Polson et al. |
| 5,700,253 A | 12/1997 | Parker |
| 5,702,373 A | 12/1997 | Samson |
| 5,747,666 A | 5/1998 | Willis |
| 5,755,704 A | 5/1998 | Lunn |
| 5,763,238 A | 6/1998 | James et al. |
| 5,797,876 A | 8/1998 | Spears et al. |
| 5,810,985 A | 9/1998 | Bao et al. |
| 5,827,242 A | 10/1998 | Follmer et al. |
| 5,891,100 A | 4/1999 | Fleckenstein |
| 5,891,114 A | 4/1999 | Chien et al. |
| 5,922,612 A | 7/1999 | Alder et al. |
| 5,947,940 A | 9/1999 | Beisel |
| 5,951,929 A | 9/1999 | Wilson |
| 5,954,651 A | 9/1999 | Berg et al. |
| 6,002,954 A | 12/1999 | Van Antwerp et al. |
| 6,011,984 A | 1/2000 | Van Antwerp et al. |
| 6,019,736 A | 2/2000 | Avellanet et al. |
| 6,117,290 A | 9/2000 | Say et al. |
| 6,152,933 A | 11/2000 | Werp et al. |
| 6,156,010 A | 12/2000 | Kuracina et al. |
| 6,175,752 B1 | 1/2001 | Say et al. |
| 6,187,130 B1 | 2/2001 | Berard et al. |
| 6,200,301 B1 | 3/2001 | Pfeiffer et al. |
| 6,254,829 B1 | 7/2001 | Hartmann et al. |
| 6,273,874 B1 | 8/2001 | Parris |
| 6,304,766 B1 | 10/2001 | Colvin, Jr. |
| 6,319,540 B1 | 11/2001 | Van Antwerp et al. |
| 6,363,273 B1 | 3/2002 | Mastrorio et al. |
| 6,370,406 B1 | 4/2002 | Wach et al. |
| 6,375,627 B1 | 4/2002 | Mauze et al. |
| 6,387,672 B1 | 5/2002 | Arimori et al. |
| 6,464,849 B1 | 10/2002 | Say et al. |
| 6,544,212 B2 | 4/2003 | Galley et al. |
| 6,584,335 B1 | 6/2003 | Haar et al. |
| 6,585,665 B1 | 7/2003 | Chapman et al. |
| 6,602,702 B1 | 8/2003 | McDevitt et al. |
| 6,623,490 B1 | 9/2003 | Crane et al. |
| 6,627,177 B2 | 9/2003 | Singaram et al. |
| 6,653,141 B2 | 11/2003 | Singaram et al. |
| 6,663,595 B2 | 12/2003 | Spohn et al. |
| 6,682,938 B1 | 1/2004 | Satcher, Jr. et al. |
| 6,702,972 B1 | 3/2004 | Markle |
| 6,711,423 B2 | 3/2004 | Colvin |
| 6,766,183 B2 | 7/2004 | Walsh et al. |
| 6,794,195 B2 | 9/2004 | Colvin |
| 6,800,451 B2 | 10/2004 | Daniloff et al. |
| 6,804,544 B2 | 10/2004 | Van Antwerp et al. |
| 6,858,403 B2 | 2/2005 | Han et al. |
| 7,064,103 B2 | 6/2006 | Pitner et al. |
| D525,632 S | 7/2006 | Jost et al. |
| 7,181,260 B2 | 2/2007 | Gutierrez |
| D544,871 S | 6/2007 | Lim et al. |
| 7,226,414 B2 | 6/2007 | Ballerstadt |
| 7,229,450 B1 | 6/2007 | Chitre et al. |
| D550,242 S | 9/2007 | Niijima |
| D550,245 S | 9/2007 | Niijima |
| 7,276,029 B2 | 10/2007 | Goode, Jr. et al. |
| 7,277,740 B2 | 10/2007 | Rohleder et al. |
| 7,277,745 B2 | 10/2007 | Natarajan et al. |
| D559,264 S | 1/2008 | Niijima |
| D560,224 S | 1/2008 | Park et al. |
| 7,316,909 B2 | 1/2008 | Pitner et al. |
| 7,317,111 B2 | 1/2008 | Bhatt et al. |
| D610,065 S | 2/2008 | Park et al. |
| 7,353,055 B2 | 4/2008 | Hogan |
| 7,358,094 B2 | 4/2008 | Bell et al. |
| 7,381,938 B2 | 6/2008 | Kobayashi et al. |
| 7,390,462 B2 | 6/2008 | Rao et al. |
| 7,417,164 B2 | 8/2008 | Suri |
| D580,950 S | 11/2008 | Steele et al. |
| D582,939 S | 12/2008 | Neuhaus |
| 7,470,420 B2 | 12/2008 | Singaram et al. |
| D592,223 S | 5/2009 | Neuhaus |
| 7,559,894 B2 | 7/2009 | McEowen |
| 7,615,007 B2 | 11/2009 | Shults et al. |
| 7,661,301 B2 | 2/2010 | Moor |
| 7,751,863 B2 | 7/2010 | Markle et al. |
| 7,767,846 B2 | 8/2010 | Suri |
| D626,143 S | 10/2010 | Karten et al. |
| 7,807,210 B1 | 10/2010 | Roorda et al. |
| 7,824,918 B2 | 11/2010 | Suri |
| 7,829,341 B2 | 11/2010 | Gamsey et al. |
| 7,879,024 B2 | 2/2011 | Thorstenson et al. |
| 7,881,780 B2 | 2/2011 | Flaherty |
| 7,939,664 B2 | 5/2011 | Gamsey et al. |
| 8,088,097 B2 | 1/2012 | Markle et al. |
| 8,110,251 B2 | 2/2012 | Markle et al. |
| 8,178,676 B2 | 5/2012 | Gamsey et al. |
| 8,202,731 B2 | 6/2012 | Suri |
| 8,512,245 B2 | 8/2013 | Markle et al. |
| 8,535,262 B2 | 9/2013 | Markle et al. |
| 2001/0016682 A1 | 8/2001 | Berner et al. |
| 2002/0018843 A1 | 2/2002 | Van Antwerp et al. |
| 2002/0026108 A1 | 2/2002 | Colvin, Jr. |
| 2002/0107178 A1 | 8/2002 | Van Den Berghe |
| 2002/0128546 A1 | 9/2002 | Silver |
| 2002/0193672 A1 | 12/2002 | Walsh et al. |
| 2003/0013974 A1 | 1/2003 | Natarajan et al. |
| 2003/0028089 A1 | 2/2003 | Galley et al. |
| 2003/0065254 A1 | 4/2003 | Schulman et al. |
| 2003/0100821 A1 | 5/2003 | Heller et al. |
| 2003/0171666 A1 * | 9/2003 | Loeb et al. ............... 600/407 |
| 2003/0232383 A1 | 12/2003 | Daunert et al. |
| 2004/0028612 A1 | 2/2004 | Singaram et al. |
| 2004/0072358 A1 | 4/2004 | Ballerstadt |
| 2004/0087842 A1 | 5/2004 | Lakowicz et al. |
| 2004/0136924 A1 | 7/2004 | Boyd et al. |
| 2004/0219535 A1 | 11/2004 | Bell et al. |
| 2004/0243018 A1 | 12/2004 | Organ et al. |
| 2004/0260158 A1 | 12/2004 | Hogan |
| 2004/0260162 A1 | 12/2004 | Rohleder et al. |
| 2004/0267203 A1 | 12/2004 | Potter et al. |
| 2005/0054975 A1 | 3/2005 | Patel et al. |
| 2005/0090014 A1 | 4/2005 | Rao et al. |
| 2005/0113658 A1 | 5/2005 | Jacobson et al. |
| 2005/0118726 A1 * | 6/2005 | Schultz et al. ............... 436/518 |
| 2005/0123935 A1 | 6/2005 | Haugland et al. |
| 2005/0130249 A1 | 6/2005 | Parris et al. |
| 2005/0193860 A1 | 9/2005 | Schulman et al. |
| 2005/0233465 A1 | 10/2005 | Miller |
| 2005/0240086 A1 | 10/2005 | Akay |
| 2005/0241959 A1 | 11/2005 | Ward et al. |
| 2005/0266038 A1 | 12/2005 | Glauser et al. |
| 2005/0267326 A1 | 12/2005 | Loeb et al. |
| 2005/0282225 A1 | 12/2005 | Daunert et al. |

(56) References Cited

U.S. PATENT DOCUMENTS

| | | |
|---|---|---|
| 2005/0283204 A1 | 12/2005 | Buhlmann et al. |
| 2006/0083688 A1* | 4/2006 | Singaram et al. ............... 424/9.6 |
| 2006/0084854 A1 | 4/2006 | Cho et al. |
| 2006/0088722 A1 | 4/2006 | Aller et al. |
| 2006/0105174 A1 | 5/2006 | Aller et al. |
| 2006/0173252 A1 | 8/2006 | Ellingsen et al. |
| 2006/0189863 A1 | 8/2006 | Peyser et al. |
| 2006/0189979 A1 | 8/2006 | Esch et al. |
| 2006/0195042 A1 | 8/2006 | Flaherty |
| 2006/0287600 A1 | 12/2006 | McEowen |
| 2007/0020181 A1 | 1/2007 | Workman et al. |
| 2007/0038155 A1 | 2/2007 | Kelly, Jr. et al. |
| 2007/0060872 A1 | 3/2007 | Hall et al. |
| 2007/0100356 A1 | 5/2007 | Lucatero et al. |
| 2007/0123775 A1 | 5/2007 | Meyer et al. |
| 2007/0136825 A1 | 6/2007 | Frommer et al. |
| 2007/0156079 A1 | 7/2007 | Brown |
| 2007/0175828 A1 | 8/2007 | Goedje et al. |
| 2007/0179437 A1 | 8/2007 | Grage et al. |
| 2007/0256477 A1 | 11/2007 | Moor |
| 2008/0001091 A1 | 1/2008 | Kobayashi et al. |
| 2008/0009687 A1 | 1/2008 | Smith et al. |
| 2008/0027245 A1 | 1/2008 | Suri |
| 2008/0086042 A1 | 4/2008 | Brister et al. |
| 2008/0154101 A1 | 6/2008 | Jain et al. |
| 2008/0154107 A1 | 6/2008 | Jina |
| 2008/0183061 A1 | 7/2008 | Goode et al. |
| 2008/0188722 A1 | 8/2008 | Markle et al. |
| 2008/0287761 A1 | 11/2008 | Hayter et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0311675 A1 | 12/2008 | Thomas et al. |
| 2008/0312560 A1 | 12/2008 | Jamsen et al. |
| 2009/0005266 A1 | 1/2009 | Ostermeier et al. |
| 2009/0018418 A1 | 1/2009 | Markle et al. |
| 2009/0018426 A1 | 1/2009 | Markle et al. |
| 2009/0048430 A1 | 2/2009 | Hellinga et al. |
| 2009/0061528 A1 | 3/2009 | Suri |
| 2009/0062696 A1 | 3/2009 | Nathan et al. |
| 2009/0076336 A1 | 3/2009 | Mazar et al. |
| 2009/0081803 A1 | 3/2009 | Gamsey et al. |
| 2009/0082566 A1 | 3/2009 | Mitra |
| 2009/0088329 A1 | 4/2009 | Brennan et al. |
| 2009/0098052 A1 | 4/2009 | Schilling et al. |
| 2009/0104714 A1 | 4/2009 | Thomas et al. |
| 2009/0112075 A1 | 4/2009 | Klok et al. |
| 2009/0143659 A1 | 6/2009 | Li et al. |
| 2009/0171381 A1 | 7/2009 | Schmitz et al. |
| 2009/0177143 A1 | 7/2009 | Markle et al. |
| 2009/0182217 A1 | 7/2009 | Li et al. |
| 2009/0192416 A1 | 7/2009 | Ernst et al. |
| 2009/0196864 A1 | 8/2009 | Bulla |
| 2009/0200620 A1 | 8/2009 | Omura et al. |
| 2009/0228068 A1 | 9/2009 | Buhlmann et al. |
| 2009/0264719 A1 | 10/2009 | Markle et al. |
| 2009/0275815 A1 | 11/2009 | Bickoff et al. |
| 2009/0324945 A1 | 12/2009 | Licht et al. |
| 2010/0173065 A1 | 7/2010 | Michal et al. |
| 2010/0274110 A1 | 10/2010 | Markle |
| 2010/0279424 A1 | 11/2010 | Suri |
| 2010/0292617 A1 | 11/2010 | Lei et al. |
| 2010/0312483 A1 | 12/2010 | Peysr |
| 2011/0077477 A1 | 3/2011 | Romey et al. |
| 2011/0105866 A1 | 5/2011 | Markle |
| 2011/0152658 A1 | 6/2011 | Peyser |
| 2011/0171742 A1 | 7/2011 | Gamsey |
| 2011/0224516 A1 | 9/2011 | Romey |
| 2011/0236989 A1 | 9/2011 | Suri et al. |
| 2011/0263953 A1 | 10/2011 | Markle |
| 2012/0053427 A1 | 3/2012 | Markle |
| 2012/0116191 A1 | 5/2012 | Markle |
| 2012/0208286 A1 | 8/2012 | Gamsey |
| 2012/0282412 A1 | 11/2012 | Markle |
| 2013/0267801 A1 | 10/2013 | Romey |
| 2013/0267802 A1 | 10/2013 | Markle |
| 2013/0287631 A1 | 10/2013 | Romey |

FOREIGN PATENT DOCUMENTS

| | | |
|---|---|---|
| DE | 3036868 | 5/1982 |
| DE | 3509262 | 10/1985 |
| DE | 3720736 | 1/1989 |
| DE | 195 02 183 | 8/1996 |
| DE | 298 17 986 | 2/1999 |
| DE | 198 20 808 | 11/1999 |
| EP | 0 073 558 | 3/1983 |
| EP | 0 147 168 | 7/1985 |
| EP | 0 596 700 | 5/1994 |
| EP | 0 617 977 A1 | 10/1994 |
| EP | 0 758 451 B1 | 1/1999 |
| EP | 000760723-0001 | 7/2007 |
| EP | 2 162 057 | 3/2010 |
| EP | 2 217 316 | 7/2010 |
| EP | 2 222 686 | 8/2010 |
| EP | 2 147 003 | 4/2011 |
| EP | 2 054 476 | 6/2011 |
| EP | 2 438 152 | 4/2012 |
| EP | 2 496 139 | 9/2012 |
| FR | 2 350 831 | 12/1977 |
| FR | 2 624 007 | 6/1989 |
| GB | 1 123 094 | 8/1968 |
| GB | 1 447 163 | 8/1976 |
| GB | 2 048 682 | 12/1980 |
| JP | 52-52496 | 4/1977 |
| JP | 53-68249 | 6/1978 |
| JP | 54-13347 | 1/1979 |
| JP | 54-111363 | 8/1979 |
| JP | 54-155856 | 12/1979 |
| JP | 56-116752 | 9/1981 |
| JP | 56-116754 | 9/1981 |
| JP | 58-162921 | 9/1983 |
| JP | 3-52936 | 3/1991 |
| JP | 06-016859 | 4/1994 |
| JP | 2003-262613 | 9/2003 |
| JP | 2005-287762 | 10/2005 |
| JP | 2005-315871 | 11/2005 |
| JP | 1332866 | 5/2008 |
| JP | 2009-544729 | 12/2009 |
| JP | 2010-507711 | 3/2010 |
| JP | 2010-517693 | 5/2010 |
| JP | 2010-518397 | 5/2010 |
| JP | 2010-526599 | 8/2010 |
| JP | 2010-527010 | 8/2010 |
| JP | 2010-535903 | 11/2010 |
| JP | 2011-504399 | 2/2011 |
| JP | 2011-511755 | 4/2011 |
| JP | 5017377 | 6/2012 |
| JP | 2012-529060 | 11/2012 |
| SU | 6216724 | 8/1978 |
| WO | WO 87/00920 | 2/1987 |
| WO | WO 88/004415 | 6/1988 |
| WO | WO 91/09312 | 6/1991 |
| WO | WO 92/019150 | 11/1992 |
| WO | WO 93/16406 | 8/1993 |
| WO | WO 94/10553 | 5/1994 |
| WO | WO 95/30148 | 11/1995 |
| WO | WO 96/22730 | 8/1996 |
| WO | WO 96/022798 | 8/1996 |
| WO | WO 97/020530 | 6/1997 |
| WO | WO 97/037713 | 10/1997 |
| WO | WO 97/048437 | 12/1997 |
| WO | WO 98/08554 | 3/1998 |
| WO | WO 00/02048 | 1/2000 |
| WO | WO 00/13003 | 3/2000 |
| WO | WO 00/43536 | 7/2000 |
| WO | WO 01/20019 | 3/2001 |
| WO | WO 01/60248 | 8/2001 |
| WO | WO 02/46752 | 6/2002 |
| WO | WO 03/034047 | 4/2003 |
| WO | WO 03/060464 | 7/2003 |
| WO | WO 2004/054438 | 7/2004 |
| WO | WO 2004/099778 | 11/2004 |

(56) References Cited

FOREIGN PATENT DOCUMENTS

| WO | WO 2005/090014 | 4/2005 |
|---|---|---|
| WO | WO 2005/065241 | 7/2005 |
| WO | WO 2006/044973 | 4/2006 |
| WO | WO 2007/059311 | 5/2007 |
| WO | WO 2007/067743 | 6/2007 |
| WO | WO 2007/105140 | 9/2007 |
| WO | WO 2008/001091 | 1/2008 |
| WO | WO 2008/014280 | 1/2008 |
| WO | WO 2008/072338 | 6/2008 |
| WO | WO 2008/097747 | 8/2008 |
| WO | WO 2008/098011 | 8/2008 |
| WO | WO 2008/098087 | 8/2008 |
| WO | WO 2008/137604 | 11/2008 |
| WO | WO 2008/141241 | 11/2008 |
| WO | WO 2008/141243 | 11/2008 |
| WO | WO 2009/009756 | 1/2009 |
| WO | WO 2009/018426 | 1/2009 |
| WO | WO 2009/021057 | 2/2009 |
| WO | WO 2009/067626 | 5/2009 |
| WO | WO 2009/129186 | 10/2009 |
| WO | WO 2010/141888 | 9/2010 |
| WO | WO 2010/123972 | 10/2010 |
| WO | WO 2011/041546 | 4/2011 |
| WO | WO 2011/056274 | 5/2011 |
| WO | WO 2011/075710 | 6/2011 |
| WO | WO 2011/075711 | 6/2011 |
| WO | WO 2011/084713 | 7/2011 |
| WO | WO 2011/097586 | 8/2011 |
| WO | WO 2011/112030 | 9/2011 |
| WO | WO 2011/137178 | 11/2011 |
| WO | WO 2013/033076 | 3/2013 |
| WO | WO 2013/049068 | 4/2013 |

OTHER PUBLICATIONS

International Search Report and Written Opinion Received in PCT/US2008/053226 Dated Oct. 15, 2008.
U.S. Reexamination, Request for Inter parties Reexamination, dated Sep. 6, 2012.
U.S. Transmittal of Communication toThird Party Requste Inter Partes Reexamination dated Oct. 22, 2012.
Agayn, V. I. and Dr. R. Walt (1993). "Fiber-optic sensor for continuous monitoring of fermentation pH." Biotechnology 72(6):6-9.
Angel, S. M., "Optrodes: Chemically Selective Fiber Optic Sensors," Spectoscopy, Apr. 1987, pp. 38-47.
Atherton, S. J., et al.: "Reactions of Three Bis(viologen) Tetraquaternary Salts and Their Reduced Radicals", J. Am. Chern. Soc. 1986, 108,3380-3385.
Badugu R., et al, "Wavelength-ratiometric near-physiological pH sensors based on 6-aminoquinolinium boronic acid probes" Talanta, Elsevier, Amsterdam, NL, Apr. 30, 2005, vol. 66, Issue No. 3, pp. 569-574.
Badugu, R. et al. "Boronic acid fluorescents ensors for monosaccharide signaling based on the 6-methoxyquinolinium heterocyclic nucleus: progress toward noninvasive and continuous glucose monitoring." 2005 Bioorg. Med. Chem. 13 (1):113-119.
Badugu, R. et al. "Fluorescence sensors for monosaccharides based on the 6-methylquinolinium nucleus and boronic acid moiety: potential application to ophthalmic diagnostics." 2005 Talanta 65 (3):762-768.
Badugu, R., et al.: "A Glucose sensing contact lens: A new approace to non-invasive continuous physiological glucose monitoring", SPIE Proceedings, The International Society for Optical Engineering—SPIE, Bellingha, Washington, USA, vol. 5317, Jan. 25, 2004.
Ballerstadt, Ralph, et al.: "Fluorescence Resonance Energy Transfer-Based Near-Infrared Fluorescence Sensor for Glucose Monitoring", Diabetes Technology & Therapeutics, vol. 6, No. 2, Apr. 1, 2004.
Bean & Johnson, 54 J. Am. Chem. Soc. 4415 (1932).
Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495.
Burnett, Peebles & Hageman, 96 Biochemical and Biophysical Research Communications 157 (1980).
Cappuccio, F.E. et al. 2004 "Evaluation of pyranine derivatives in boronic acid based saccharide sensing: Significance of charge interaction between dye and quencher in solution and hydrogel" Journal of Fluorescence 14:521-533.
Cao, H., et al.: "Fluorescent Chemosensors for Carbohydrates: A Decade's Worth of Bright Spies for Saccharides in Review", Journal of Fluorescence, vol. 14, No. 5, Sep. 2004.
Check, W., "ICUs tighten belts on blood glucose levels", Cap Today, Feb. 2005, in 7 pages, vol. 19-2, pp. 1,95-96,98,100,102, and 104 ("Check").
Choleau et al.: "Calibration of a subcutaneous amperometric glucose sensor implanted for 7 days in diabetic patients, Part 2. Superiority of the one-point calibration method." Biosensors and Bioelectrics, vol. 17, No. 8, Aug. 1, 2002.
Cordes, D. B., et al., 2006, in Topics in Fluorescence Spectroscopy; vol. 11, Glucose Sensing, Springer "Two component optical sugar sensing using boronic acid-substituted viologens with anionic fluorescent dyes" pp. 47-87. (ISBN: 978-0-387-29571-8 paQe 76, scheme 3.7).
Cordes, D. B., et al.: "The Interaction of Boronic Acid-Substituted Viologens with Pyranine: The Effects of Quencher Charge on Fluorescence Quenching and Glucose Response", Langmuir 2005,21, 6540-6547.
Dawson, et al., 98 JACS 5996 (1970).
Definition of "cathether" from Webster's Ninth New Collegiate Dictionary, 1990, p. 216.
DiCesare, N., et al.: "Saccharide Detection Based on the Amplified Fluorescence Quenching of a Water-Soluble Poly(phenylene ethynylene) by a Boronic Acid Functionalized Benzyl Viologen Derivativ~", LanQrnuir.2002,18, 7785-7787.
English Translation of DE 3,720,736.
EPO Exam Report re EP App. No. 08 728 399.0, dated Dec. 7, 2010.
European Examination Report dated May 11, 2010, re EP Application No. 08 729 209.0.
European Examination Report dated Jan. 25, 2012, re EP Application No. 08 729209.0.
European Examination Report dated Jul. 2, 2012, re EP Application No. 08 729209.0.
EPO Office Action re App. No. 07 799 791.4 dated Jan. 29, 2010.
European Examination Report re Application No. 08 755 267.5, dated Apr. 26, 2010.
European Examination Report re Application No. 08 755 267.5, dated Sep. 14, 2010.
European Examination Report re App, No. 08 797 302.0, dated Nov. 7, 2011.
European Examination Report re App. No. 08 797 302.0, dated Jan. 24, 2011.
European Examination dated Apr. 1, 2010, re EP Application No. 08 769 266.1-1211.
European Supplementary Search Report, re EP Application EP 10 78 4194, dated Nov. 8, 2012.
"Fiber Optic Oxygen Sensors: Theory of Operation", Fiber Optic Oxygen Sensors Theory of Operation, http://www.oceanoptics.com/Products/sensortheory.asp—4 pages.
Forster, "Intermolecular Energy Transfer and Fluorescence, Annaten der Physik" (1948) pp. 55-75.
Furnary A.P. et al. "Effect of hyperglycemia and continuous intravenous insulin infusions on outcomes of cardiac surgical procedures: The Portland Diabetic Project", Endocrine Practice, Mar./Apr. 2004, pp. 21-33, vol. 10.
Gamoh, et al., 222 Analytica Chimica Acta 201 (1989).
Gamsey, S. et al. 2007 "Boronic acid based bipyridinium salts as tunable receptors for monosaccharides and alpha-hydroxycarboxylates" J Am Chem Soc 129:1278-1286.
Gamsey, Soya et al.: "Continuous glulcose detection using boronic acid-substituted viologens in, fluorescent hydrogels: linker effects and extension to fiber optics" Langmuir, ACS, Washington, DC vol. 22, No. 21, Oct. 10, 2006, pp. 9067-9074 (XP002442273ISSN: 0743-7463, compound (1) schemata 1,2 figure 1).

(56) References Cited

OTHER PUBLICATIONS

Gehrich, J. L., D. W. Lubbers, et al. (1986). "Optical fluorescence and its application to an intravascular blood gas monitoring system." IEE TBio-med Eng BME-33: 117-132.

Glazer, "The Time-Dependent Specific Interaction of 4-(4'-Aminophenylazo)Phenylarsonic Acid with Subtilisins," 59 Biochemistry 996 (1968).

Glazer, Chemical Abstracts, vol. 68, No. 23, Jun. 3, 1968, p. 111809 (total 3 pages).

Guilbault, George E., "Practical Fluorescence" (1973), pp. 599-600.

Hakkinen, Lajunen & Purokoski, A Potentiometric Study on the Complex Formation of Lactitol and Maltitol with Some Inorganic Oxyacids in Aqueous Solution, Chemical Abstracts, vol. 110, No. 83116f (1989).

Hakkinen, Purokoski & Lajunen, A Potentiometric Study on the Complex Formation of Germanic Acid and Germanate Ion with Sugar Acids and Disaccharides in Aqueous Solution, Chemical Abstracts, vol. 105, No. 233265s (1986).

Hayashi, et al., "Fluorometric measurement of glycosylated albumin in human serum," 149 Clinica Chimica Acta 149 (1985), 13-19 Elsevier.

Hirata O. et al. 2002 "Allosteric saccharide sensing by a phenylboronic-acids-appended 5,15-bis(triarylethynyl)porphyrin" J Supramolecular Chemistry 2:133-142.

Hirsch Irl B. et al. "Acute Complications of Diabetes" Endocrinology and Metabolism Clinics of North America, Dec. 2000, pp. 745-771, vol. 29-4.

Hirshfeld, "Reabsorption Sensing in Fluorescence Spectroscopy," UCRL Abstract No. 89736 ABST, published by Pittsberg Conference on Scientific Instrumentation, Mar. 1984.

Hvastkovs, E. G., et al.: "Minor Groove Binding of a Novel Tetracationic Diviologen", Langmuir 2006, 22, 10821-10829.

Japanese First Office Action, re JP Application No. 2009-549167, dated Nov. 29, 2011.

Japanese Office Action, re JP Application No. 2009-521962, dated Jul. 31, 2012.

Japanese Office Action, re JP Application No. 2009-549225, mailed Sep. 4, 2012.

Japanese Office Action, re JP Application No. 2010-507712, dated Jun. 15, 2012.

Kirk-Othmer, Encyclopedia of Chemical Technology, 3rd ed., vol. 8, John Wiley and Sons, New York, pp. 201-203 (1979).

Kostov, Y., P. Harms, et al. (2001). "Low-cost microbioreactor for high-throughput bioprocessing." Biotechnol Bioeng 72: 346-352.

Kuraganov, B. I., et al.: Criterion for Hill equation validity for description of biosensor calibration curves', Analytica Chimica Acta, vol. 427, No. 1, Jan. 1, 2001.

Kuwabara, T., et al.: "Effect of Alkali Metal Ions on Photochromic Behavior of Bisviologen-incorporated Oligo-oxyethylene Units", Rapid Communication. Photochemistry and Photobiology, 2003, 77(5); 572-575.

Lakowitz et al., :"Optical sensing of glucose using phase-modulation fluorimtry," Analytica Chimica Acta, 271, (1993), 155-164.

Lee, S. K., et al.: "Conform¯tion and binding properties of polymethylene-linked bisviologens-2-naphthol complexes", Journal of the Chemical Society, Perkin Transactions 2 2001, 1983-1988.

Leijten FSS & De Weerdt A W 1994 Critical illness polyneuropathy: a review of the literature, definition and pathophysiology. Clinical Neurology and Neurosurgery, 96: 10-19.

Levetan et al., "Hospital Management of Diabetes," in Acute Complications of Diabetes, vol. 29, No. 4, 745-71, at 745-54 (Dec. 2000).

Lindner, et al., 473 J. Chromatography 227-240 (1989).

Lutty, G. A. (1978). "The acute intravenous toxicity of stains, dyes, and other fluorescent substances." Toxical Pharmacol. 44: 225-229.

Meadows and Schultz, "Design, manufacture and characterization of an optical fiber glucose affinity sensor based on an homogeneous fluorescence energy transfer assay system," (1993) Anal. Chim. Acta 280: pp. 21-30.

Medtronic, Features of the Guardian REAL-Time Continuous Glucose Monitoring System, Features that fit your diabetes management lifestyle, located at http://www.minimed.com/products/guardian/features.html on Aug. 28, 2007.

Mizock B A. Am J Med 1995; 98: 75-84.

Mohr, G. J. et al.: Application of a Novel Lipophilized Fluorescent dye in an Opitcal Nitrate Sensor, Journal of Fluorescence 1995, 5, 135-138.

Mosbach, Methods in Enzymology, vol. XLIV, 53 (1976).

Nielsen, Jannik K., et al.: "Clinical Evaluation of a Transcutaneous Interrogated Fluorescence Lifetime-Based Microsensor for Continuous Glucose Reading", Journal of Diabetes Science and Technology, vol. 3, No. 1, Jan. 1, 2009.

Niu C.G. et al. "Fluorescence ratiometric pH sensor prepared from covalently immobilized porphyrin and benzothioxanthen e." 2005 Anal. Bioanal. Chem. 383(2):349-357.

Offenbacher, H., O. S. Wolfbeis, et al. (1986). "Fluorescence optical sensors for continuous determination of near-neutral pH values." Sensor Actuator 9: 73-84.

"Optical Glucose Sensor Holds Promise for Diabetics and Intensive Care Patients," in Science Daily, Mar. 18, 2004 (archived on Apr. 4, 2004 at: <http://web.archive.org/web/20040404161607/http://www.ScienceDaily.com/releases/2004/03/0403529.htm> ("ScienceDaily Article").

Park, Y. S., et al.: "Facile Reduction of ZeoliteOEncapsulated Viologens with Solvated Electrons and Selective Dispersion of Inter- and Intramolecular Dimers of Propylene-Bridged Bisviologen Radical Cation", LanQmuir 2000,16,4470-4477.

PCT International Search Report and Written Opinion re PCT/US2008/062303 dated Aug. 14, 2008.

PCT International Report on Patentability re PCT/US2010/044761, dated May 8, 2012.

PCT International Preliminary Report on Patentability and Written Opinion re PCT Application No. PCT/US20101061169, dated Jun. 19, 2012.

PCT International Preliminary Report on Patentability re PCT/US201 01037502, dated Dec. 6, 2011.

PCT International Preliminary Report on Patentability and Written Opinion date of Issuance Apr. 3, 2012.

PCT International Search Report and Report on Patentability re PCT Application No. PCT/US20101061163, dated (mailed) Jun. 28, 2012.

PCT International Preliminary Report on Patentability and Written Opinion re PCT Application No. PCT/US201 01061173, dated Jun. 19, 2012.

PCT International Preliminary Report on Patentability re PCT/US2011/034167, issued Oct. 30, 2012.

Purokoski, Lajunen & Hakkinen, A Potentiometric Study on the Complex Formation of Arsenious Acid, Arsenite Ion, Telluric Acid and Tellurate Ion with Sugar Acids and Disaccharides in Aqueous Solution, Chemical Abstracts, vol. 107, No. 122178n (1987).

Retrieved from the Internet <URL: http://www.invitrogen.com/site/us/en/home/References/Molecular-Probes-The-Handbook/Fluorophores-and-Their-Amine-Reactive-Derivatives/Fluorescein-Oregon-Green-and-Rhodamine-Green-Dyes.html#>, 11 pages.

Reyes-De-Corcuera, Josi et al.: "Enzyme-electropolymer-based amperometric biosensors: an innovative platform for time-temperature integrators." Journal of Agricultural and Food Chemistry, vol. 53, No. 23, Nov. 1, 2005.

Roy, et al., J. Inorg. Nucl. Chem., 106 (1957).

Sato, H., et al.: "Polymer Effect in Electrochromic Behavior of Oligomeric Viologens", Journal of Applied Polymer Science, vol. 24, 2075-2085 (1979).

Schulman, S. G., S. Chen, et al. (1995). "Dependence of the fluorescence of immobilized 1-hydroxypyrene-3,6,8-trisulfonate on solution pH: extension of the range of applicability of a pH fluorosensor." Anal Chim Acta 304: 165-170.

Seitz, "Chemical Sensors Based on Fiber Optics," Analytical Chemistry, vol. 56, pp. 16a-34a, 1984.

Sharrett, Z. et al. 2008 "Boronic acid-appended bis-viologens as a new family of viologen quenchers for glucose sensing" Tetrahedron Letters 49:300-304.

(56) References Cited

OTHER PUBLICATIONS

Snyder, et al., "The Preparation of Some Azo Boronic Acids," 70 J. Am. Chem. Soc. 232 (1948).
Song, A., S. Parus, et al. (1997) "High-performance fiber-optic pH microsensors for practical physiological measurements using a dual-emission sensitive dye." Analytical Chemistry 69: 863-867.
Stokes, et al.: "An optical oxygen sensor and reaction vessel for high-pressure applications", Limnol. Oceanogr., 44(1),1999,189-195.
Streitwieser, Jr. & Heathcock, Introduction to Organic Chemistry (1976).
Sturdevant, M. F.: "How Sterilization Changes Long-Term Resin Properties", Plastics Engineering, Jan. 1991, pp. 27-32.
Suri, J. T. et al. 2003 "Continuous glucose sensing with a fluorescent thin-film hydrogel" Angew Chem Int Ed 42:5857-5859.
Suri, J. T. et al.: "Monosaccharide Detection with 4,7-Phenanthrolinium Salts: Charge-Induced Fuorescence Sensig", Langmuir 2003,19,5145-5152.
Takashima, H., et al.: "Remarkably stereoselective photoinduced electron-transfer reaction between zinc myoglobin and optically active binaphthyl bisviologen", Journal 0 Biological Inorganic Chemistry 2003, 8, 499-506.
The Immunoassay Handbook, pp. 1-618, ed. David Wild, Macmillan Press, 1994, United Kingdom.
Tsukahara, K., et al.: "Syntheses, Characterizations, and Redox Behavior of Optically Active Viologens and Bisviologens", Bulletin of the Chemical Society of Japan 1999, 72,139-149.
Turner N. G. et al. "Determination of the pH Gradient Across the Stratum Corneum." 1998 J. Investig. Dermatol. Symp. Proc. Aug. 3(2):110-3.
Udenfreund, "Fluorescence Assay in Biology and Medicine" (1962) pp. 108-109.
Van Den Berghe G., et al. "Intensive Insulin Therapy in the Medical ICU", The New England Journal of Medicine, Feb. 2, 2006, pp. 449-461, vol. 354-5.
Van Kempien & Kreuzer, "A Single-Unit Carbon Dioxide Sensing Microelectrode System," Respiration Physiology, (1975), 23, 371-379.
Vermeer, et al., 37 Tetr. Letters 3255 (1970).
Volker, Ludwig et al.: "Continuous Glucose Monitoring with Glucose Sensors: Calibration and Assessment Criteria", Diabetes Technology & Therapeutics, vol. 5, No. 4, Aug. 1, 2003.
Wang, D. et al. 2001 "Ph()toh,Jminescence quenching of conjugated macromolecules by bipyridinium derivatives in aqueous media: charge dependence" Langmuir 17:1262-1266.
Wilson, Intensive Insulin Therapy in Critical Care, Diabetes Care, Apr. 2007, pp. 1005-1011, vol. 30-4.
Wolfbeis, O. S., E. Fuerlinger, et al. (1983). "Fluorimetric analysis. I. Study on fluorescent indicators for measuring near neutral ('physiological') pH values." Fresneius' Z. Anal. Chem. 314 (2): 119-124.
Xu, Z., A. Rollins, et al. (1998) "A novel fiber-optic pH sensor incorporating carboxy SNAFL-2 and fluorescent wavelength-ratiometric detection" Journal of Biomedical Materials Research 39:9-15.

Zhang, S., S. Tanaka, et al. (1995). "Fibre-optical sensor based on fluorescent indicator for monitoring physiological pH values." Med Biol Eng Comput 33: 152-156.
Zhujun, Z. and W. R. Seitz (1984). "A fluorescence sensor for quantifying pH in the range from 6.5 to 8.5." Analytical Chimica Acta 160:47-55.
Zhujun, Z., et al. (1984). Analytical Chimica Acta 160:305-309.
Gott, "Heparin Bonding on Colloidal Graphite Surfaces," Department of Surgery, University of Wisconsin Medical School, Madison 6 Science, vol. 142, pp. 1297-1298, Dec. 6, 1963.
Japanese Office Action (Notice of Reason for Rejection), re JP Application No. 2009-549225, dated Dec. 3, 2013.
PCT Partial Search Report re PCT/US2008/053226 dated Jun. 27, 2008.
U.S. Transmittal of Communication toThird Party Requste Inter Partes Reexamination, Right of Appeal Notice, dated Jun. 20, 2013.
Ayala et al., Database Caplus, DN 133:189758. (Protein Science (2000), 9(8), 1589-1593).
Baldini "Invasive Sensors in Medicine." Optical Chemical Sensors, NATO Science Series 11: Mathematics, Physics and Chemistry [online], 2006 [Retrieved on Nov. 15, 2010], vol. 224, pp. 417-435, Retrieved from the Internet: <URL http:www.springerlink.com>.
Benmakroha et al. "Haemocompatibility of invasive sensors," Med. & Biol. Eng. & Comput., 1995, 33,811-821 (Nov. 1995).
European Examination Report dated Apr. 30, 2013, re EP Application No. 08 729209.0.
Fidaleo et al., Database Caplus, DN 140:249134 (Chemical and Biochemical Engineering Quarterly (2003), 17(4), 311-318).
Hunneche, "Antioxidant Activity of a Combinatorial Library of Emulsifier—Antioxidant Bioconjugates," J. Agric. Food Chem. 2008, 56, 9258-9268.
Japanese Office Action (Notice f Reason for Rejection), re JP Application No. 2009-549225, dated Mar. 12, 2013.
Liu, et al., "Characterization of Immobilization of an Enzyme in a Modified Y Zeolite Matrix and Its Application to an Amperometric Glucose Biosensor," Anal. Chem. 1997, 69, pp. 2343-2348.
Mignani et al. "Biomedical sensors using optical fibres." Reports on Progress in Physics [online], Jan. 1996 [Retrieved on Nov. 15, 2010], vol. 59, No. 1, pp. 1-28, Retrieved from the internet: <URL http//iopscience.iop.org>.
Peterson et al. "Fiber-optic for in vive measurement of oxygen partial pressure," Analytical Chemistry [online], Jan. 1984 [Retrieved on Nov. 15, 2010], vol. 57, No. 1, pp. 62-67, Retrieved from the Internet: <URL: http://pubs.acs.org>.
Piper, Hannah G. "Real-Time Continuous Glucose Monitoring in Pediatric Patients During and After Cardiac Surgery," in Pediatrics, vol. 118, No. 3, Sep. 2006.
Su et al., "Polyethersulfone Hollow Fiber Membranes for Hemodialysis," Progress in Hemodialysis—From Emergent Biotechnology to Clinical Practice, www.intechopen.com, Nov. 7, 2011. ISBN 978-953-307-377-4.
Zisser, MD, et al. "Excitation: The use of Fluorescence in Glucose Monitoring (Part 11)," GLUMETRICS, Feb. 13, 2010.
Zochodne D W et al. 1987 Polyneuropathy associated with critical illness: a complication of sepsis and multiple organ failure. Brain, 110: 819-842.

\* cited by examiner

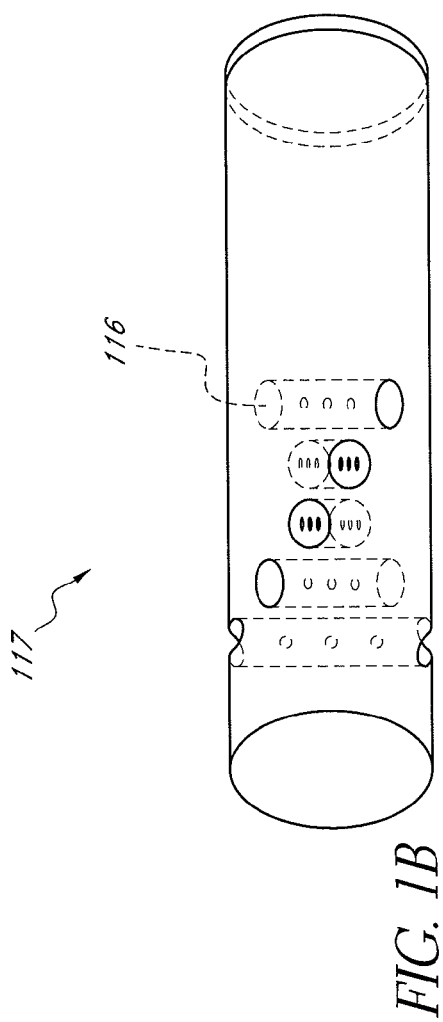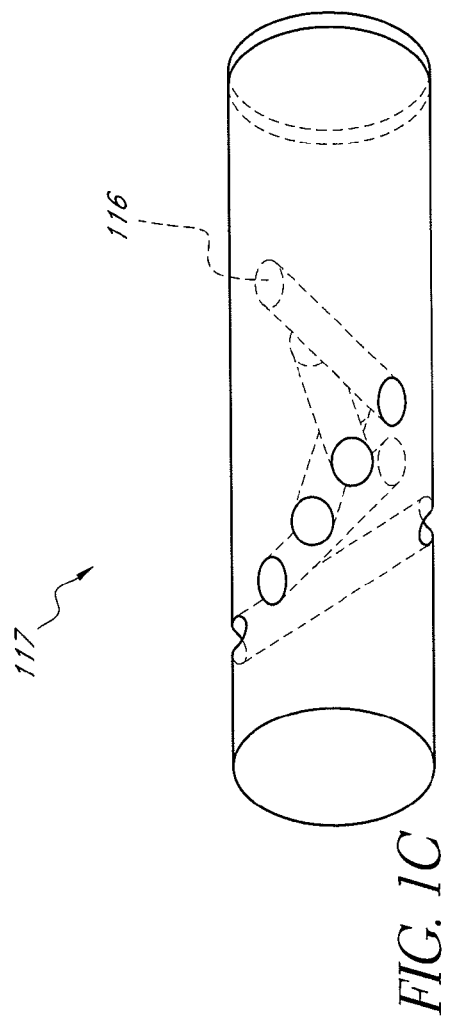

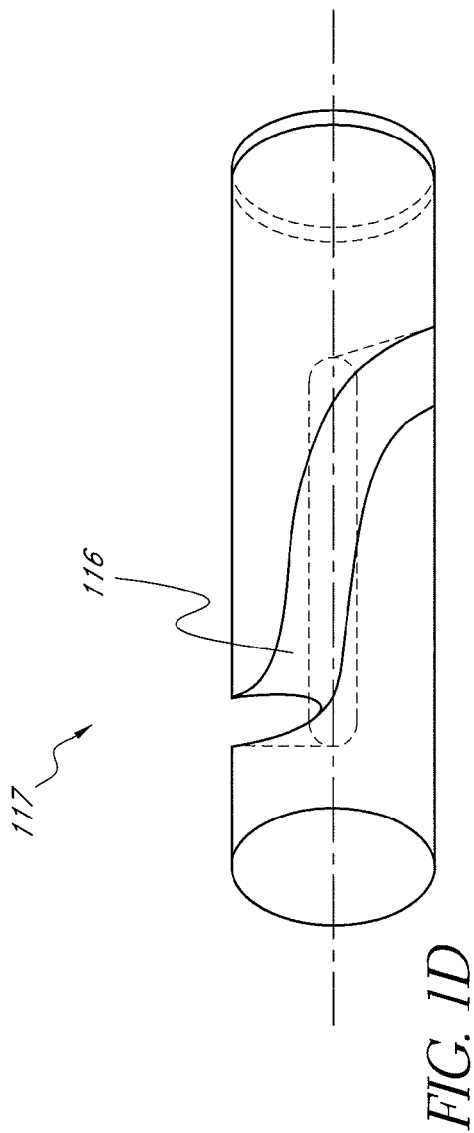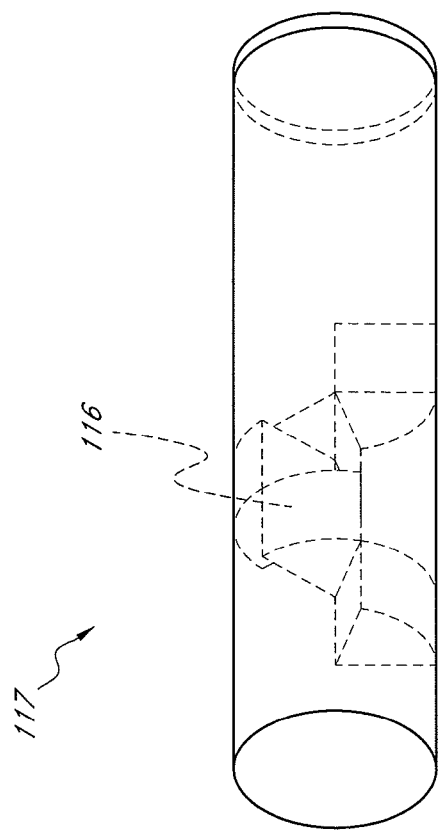
FIG. 1D
FIG. 1E

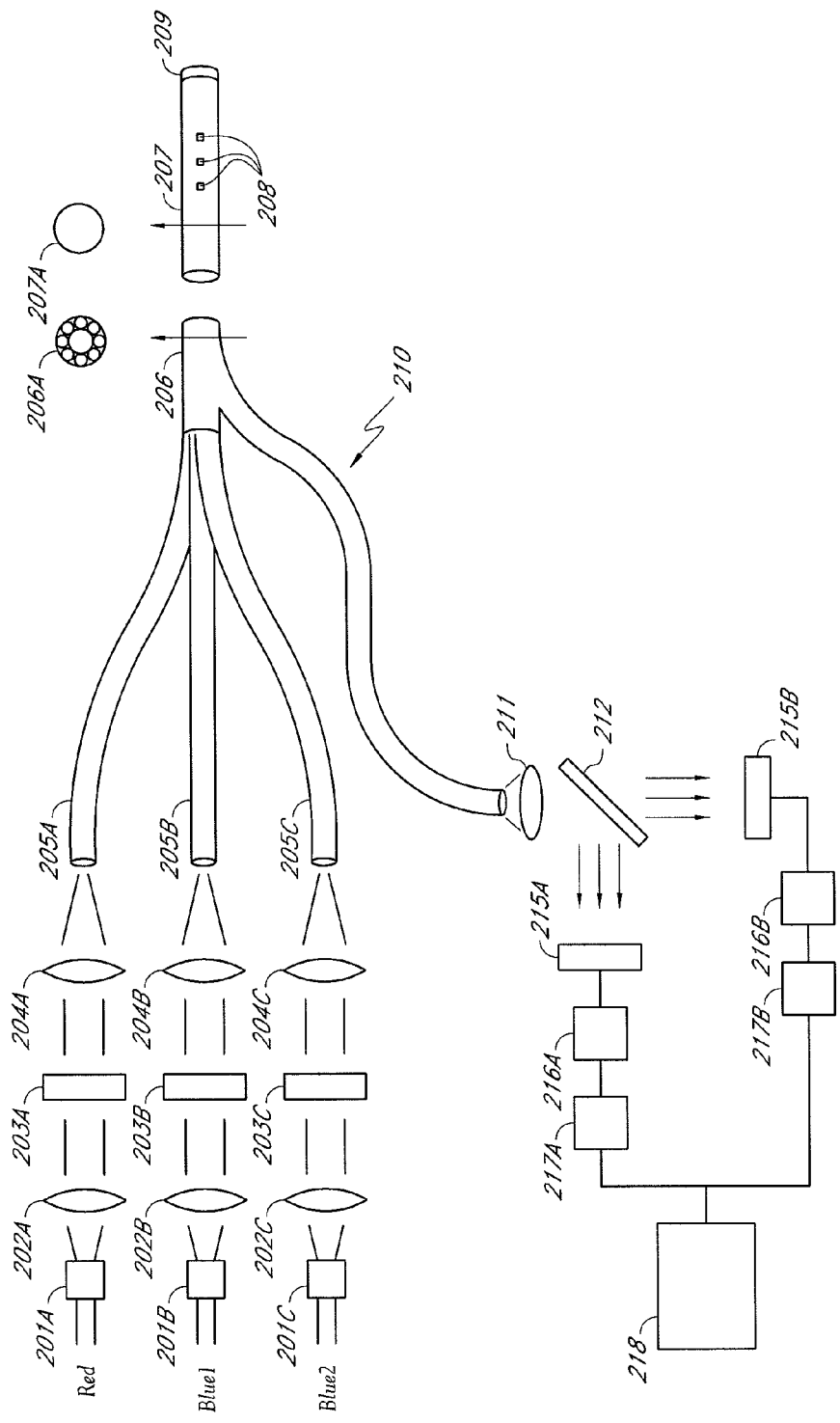

OPTICAL SYSTEMS AND METHODS FOR RATIOMETRIC MEASUREMENT OF BLOOD GLUCOSE CONCENTRATION

CROSS-REFERENCE TO RELATED APPLICATIONS

This application claims the benefit of U.S. Provisional Application No. 60/888,477, titled OPTICAL SYSTEMS AND METHODS FOR RATIOMETRIC MEASUREMENT OF BLOOD GLUCOSE CONCENTRATION and filed on Feb. 6, 2007, which is hereby incorporated by reference in its entirety, specifically the optical systems and methods for obtaining ratiometric measurements of blood glucose concentrations that are disclosed therein.

BACKGROUND

1. Field of the Invention

In preferred embodiments, the invention relates to the detection of blood glucose, and more particularly to ratiometric correction of optical glucose measurements for potential artifacts of optical systems.

2. Description of the Related Art

Hyperglycemia and insulin resistance are common in critically ill patients, even if such patients have not previously had diabetes. In these situations, glucose levels rise in critically ill patients thereby increasing the risk of damage to a patient's organs. Further, studies have shown that normalization of blood glucose levels with insulin therapy improves the prognosis for such patients, thereby decreasing mortality rates.

More recent scientific evidence confirms that dramatic improvements in the clinical outcome of hospitalized Intensive Care Unit (ICU) patients can result from tight therapeutic control of blood glucose to normal ranges. These studies indicate that Tight Glycemic Control (TGC) of ICU patients may reduce mortality by as much as 40%, and significantly lower complication rates. In these situations, it is necessary to accurately, conveniently and continuously monitor blood sugar in a real-time device specifically designed to meet the challenging needs of the ICU environment. Researchers at Johns Hopkins University estimate that TGC can save as many as 150,000 lives and reduce U.S. healthcare costs by as much as $18 billion annually.

Performing TGC requires continuous and accurate monitoring of a patient's blood glucose levels. Thus, there is a need for a real-time glucose monitoring system that is adapted to meet the needs of ICU patients.

SUMMARY OF THE INVENTION

Various embodiments of optical systems and methods are disclosed herein for determining blood glucose concentrations. The various embodiments share at least two features. First, they involve exciting a chemical indicator system with an excitation light signal and measuring the emission light signal of the indicator system, wherein the indicator system comprises a fluorophore operably coupled to a glucose binding moiety—such that the emission light signal generated by the indicator system upon excitation is related to the blood glucose concentration. Second, they involve correcting the blood glucose concentration measurements from the aforementioned indicator system for potential artifacts and errors derived from the optical systems themselves, which are unrelated to the blood glucose concentration. The correcting is performed by ratiometric analysis. More particularly, the ratio of emission light signal to a second light signal that is propagated through the optical system, e.g., the excitation light signal or a separate reference light signal, is used for correcting any non-glucose related contributions of the optical system. All of the various hardware embodiments and methods disclosed herein are configured to provide optical determination and ratiometric correction of blood glucose concentration. More detailed descriptions of the many embodiments may be found in the accompanying Drawings and Detailed Description.

An optical device for determining blood glucose concentration is disclosed in accordance with preferred aspects of the present invention. The device comprises: a fiber optic sensor sized to be positioned within a blood vessel, the sensor being optically coupled to the excitation light source and comprising an indicator system comprising a fluorophore operably coupled to a glucose binding moiety, wherein upon absorption of at least a portion of the excitation light signal, the indicator system emits an emission light signal having an intensity related to the blood glucose concentration; and a light sensitive module operably coupled to at least the fiber optic sensor, wherein the light sensitive module detects the emission light signal and at least a second light signal, wherein the second light signal is derived from the excitation light source or an optional reference light source.

In preferred embodiments, the optical device further comprises a data processing device configured to determine the blood glucose concentration in the blood vessel by performing a ratiometric analysis of the emission light signal and the at least second light signal thereby substantially compensating for changes in the optical emission signal intensity unrelated to the blood glucose concentration.

In certain embodiments, the optical device for determining blood glucose concentration comprises a reference light source that emits a reference light signal. The optical device for determining blood glucose concentration can also comprise at least one optical module configured to deliver the excitation light signal and the reference light signal to the fiber optic sensor. The optical module can comprise a collimator lens, an interference filter, and/or a focusing lens for each light source.

The optical device for determining blood glucose concentration can also comprise a mode mixing scrambler configured to remove high mode light from at least the excitation light signal. The fluorophore in the optical device can be excited by the excitation light signal and emits at least a first emission light signal and a second emission light signal, wherein the first and second emission light signals are related to glucose concentrations, and wherein a ratio of the first and second emission light signals is pH insensitive.

The optical device can also comprise a second excitation light source that emits an excitation light signal at a different wavelength than the first excitation light source. In this embodiment, the fluorophore can be excited by the first and second excitation light signals and emits a single emission light.

In certain embodiments, the light sensitive module (or detector system) in the optical device comprises a beam splitter configured to receive at least the emission light signal and the excitation light signal from the fiber optic sensor, wherein the beam splitter is configured to reflect a first portion of light and configured to allow a second portion of light to pass through the beam splitter. In other embodiments, the light sensitive module (or detector system) comprises at least a first detector, a second detector, a first amplifier, a second amplifier, and a first analog to digital converter, and a second analog to digital converter. The light sensitive module (or detector system) can also comprise, in other embodiments, a microspectrometer or spectrometer.

The fiber optic sensor in the optical device can also comprise a second fluorophore, wherein upon absorption of at least a portion of the excitation light signal, the second fluorophore emits a second emission light signal having an intensity insensitive to the blood pH and glucose concentration.

The fiber optic sensor in the optical device can also comprise a second optical fiber that is embedded with a dye, wherein the dye emits a second emissions light upon excitation by the excitation light signal. The fiber optic sensor can also comprise a dye coated surface that emits a second emission light upon excitation by the excitation light signal.

In certain embodiments, the optical device for determining blood glucose concentration, comprises: an excitation light source that emits an excitation light signal; a fiber optic sensor sized to be positioned within a blood vessel, the sensor being operably coupled to the excitation light source and comprising an indicator system comprising a fluorophore operably coupled to a glucose binding moiety, wherein upon absorption of at least a portion of the excitation light signal, the indicator system emits an emission light signal having an intensity related to the blood glucose concentration; and a detector system operably coupled to at least the sensor, wherein the detector system comprises a means for detecting the emission light signal and at least a second light signal, wherein the second light signal is derived from the excitation light source or an optional reference light source. The means for detecting the emission light signal and at least a second light signal can comprise a microspectrometer. In other embodiments, the means for detecting the emission light signal and at least a second light signal comprises at least two light detectors.

The optical device can also comprise a data processing device in communication with the detector system, wherein the data processing device determines the blood glucose concentration substantially corrected for artifacts of the optical device unrelated to the blood glucose concentration by performing a ratiometric analysis of the emission light signal and the second light signal.

In certain embodiments, an optical system for determining blood glucose concentration, comprises: an excitation light source that emits an excitation light signal; a fiber optic sensor sized to be positioned within a blood vessel, the sensor being operably coupled to the excitation light source and comprising an indicator system comprising a fluorophore operably coupled to a glucose binding moiety, wherein upon absorption of at least a portion of the excitation light signal, the indicator system emits an emission light signal having an intensity related to the blood glucose concentration; at least one optical module configured to deliver the excitation light signal to the fiber optic sensor and the emission light signal from the fiber optic sensor to a detector system, wherein the detector system comprises a means for detecting the emission light signal and at least a second light signal, wherein the second light signal is derived from the excitation light source or an optional reference light source; and a computer system configured to receive data from the detector system, wherein the computer system is configured to perform ratiometric calculations on the data to substantially eliminate optical artifacts unrelated to glucose concentrations, wherein the computer system comprises a monitor for outputting data to a user, an input device for allowing the user to input additional data into the computer system, a processor for performing the ratiometric calculations, a storage device for storing data, and a memory.

In certain embodiments, the means for detecting the emission light signal and at least a second light signal comprises a microspectrometer. The means for detecting the emission light signal and at least a second light signal can also comprise at least two light detectors.

A ratiometric method for correcting an optical measurement of blood glucose concentration for optical artifacts unrelated to the blood glucose concentration is disclosed in accordance with further aspects of the invention. The method comprises the steps of:

(1) providing an optical device comprising an excitation light source that emits an excitation light signal; a fiber optic sensor sized to be positioned within a blood vessel, the sensor being optically coupled to the excitation light source and comprising an indicator system comprising a fluorophore operably coupled to a glucose binding moiety, wherein upon absorption of at least a portion of the excitation light signal, the indicator system emits an emission light signal having an intensity related to the blood glucose concentration; and a light sensitive module operably coupled to at least the fiber optic sensor, wherein the light sensitive module detects the emission light signal and at least a second light signal, wherein the second light signal is derived from the excitation light source or an optional reference light source;

(2) deploying the fiber optic sensor within a blood vessel;

(3) actuating the excitation light source thereby exciting the indicator system, and optionally actuating the optional reference light source;

(4) detecting the emission light signal and the second light signal; and (5) correcting the blood glucose concentration, comprising: (i) calculating a ratio of the emission light signal to the second light signal; and (ii) comparing said ratio with a predetermined function that correlates ratios of emission light signals to second light signals with blood glucose concentrations.

A disposable fiber optic glucose sensor, comprising an elongate member having proximal and distal end regions, wherein the proximal end region of the elongate member is configured for operably coupling to an optical device comprising an excitation light source and a detector, and wherein the distal end region of the elongate member is sized to be positioned within a blood vessel and comprises a cavity disposed therein and a reflective surface, wherein the cavity houses an indicator system comprising a fluorophore operably coupled to a glucose binding moiety immobilized within a hydrogel configured to be permeable to glucose in the blood vessel, such that upon excitation with an excitation light signal from the excitation light source, the indicator system emits an emission light signal having an intensity related to a blood glucose concentration, wherein the reflective surface is configured to reflect the emission light signal and the excitation light signal through the optical device, and the cavity comprises a design. The disposable fiber optic glucose sensor of claim 30, wherein the reflective surface is a mirror.

In one embodiment, the hydrogel in the disposable fiber optic glucose sensor is confined by a semi-permeable membrane that allows passage of glucose and blocks passage of the binding moiety. Further, the design of the cavity in the disposable fiber optic glucose sensor of claim can comprise a plurality of holes in the elongate member. In certain embodiments, the plurality of holes are positioned perpendicular to a tangent along a length of the elongate member, and wherein the plurality of holes are evenly spaced horizontally and evenly rotated around the sides of the elongate member. The plurality of holes can also be positioned at an angle to a tangent along a length of the elongate member, and wherein the plurality of holes are evenly spaced horizontally and evenly rotated around the sides of the elongate member.

In one embodiment, the design of the cavity in the disposable fiber optic glucose sensor comprises a groove along a length of the elongate member. The groove can also comprise a depth that extends to the center of the elongate member. In other embodiments, the groove spirals around the length of the elongate member. The design of the cavity can also comprise a plurality of sections cut from the elongate member. The sections can form a triangular wedge area that extends to the center of the elongate member, and the sections can be evenly spaced horizontally and evenly rotated around the sides of the elongate member.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIG. 1B illustrates a glucose sensor embodiment comprising a series of holes that form a helical configuration.

FIG. 1C shows for example a glucose sensor embodiment comprising a series of holes drilled or formed at an angle.

FIG. 1D is an embodiment of a glucose sensor comprising at least one spiral groove.

FIG. 1E depicts a glucose sensor embodiment comprising a series of triangular wedge cut-outs.

FIG. 2A illustrates an embodiment of a glucose measurement system comprising a beam splitter with three light sources transmitting light into the glucose sensor.

DETAILED DESCRIPTION

Figure 1:
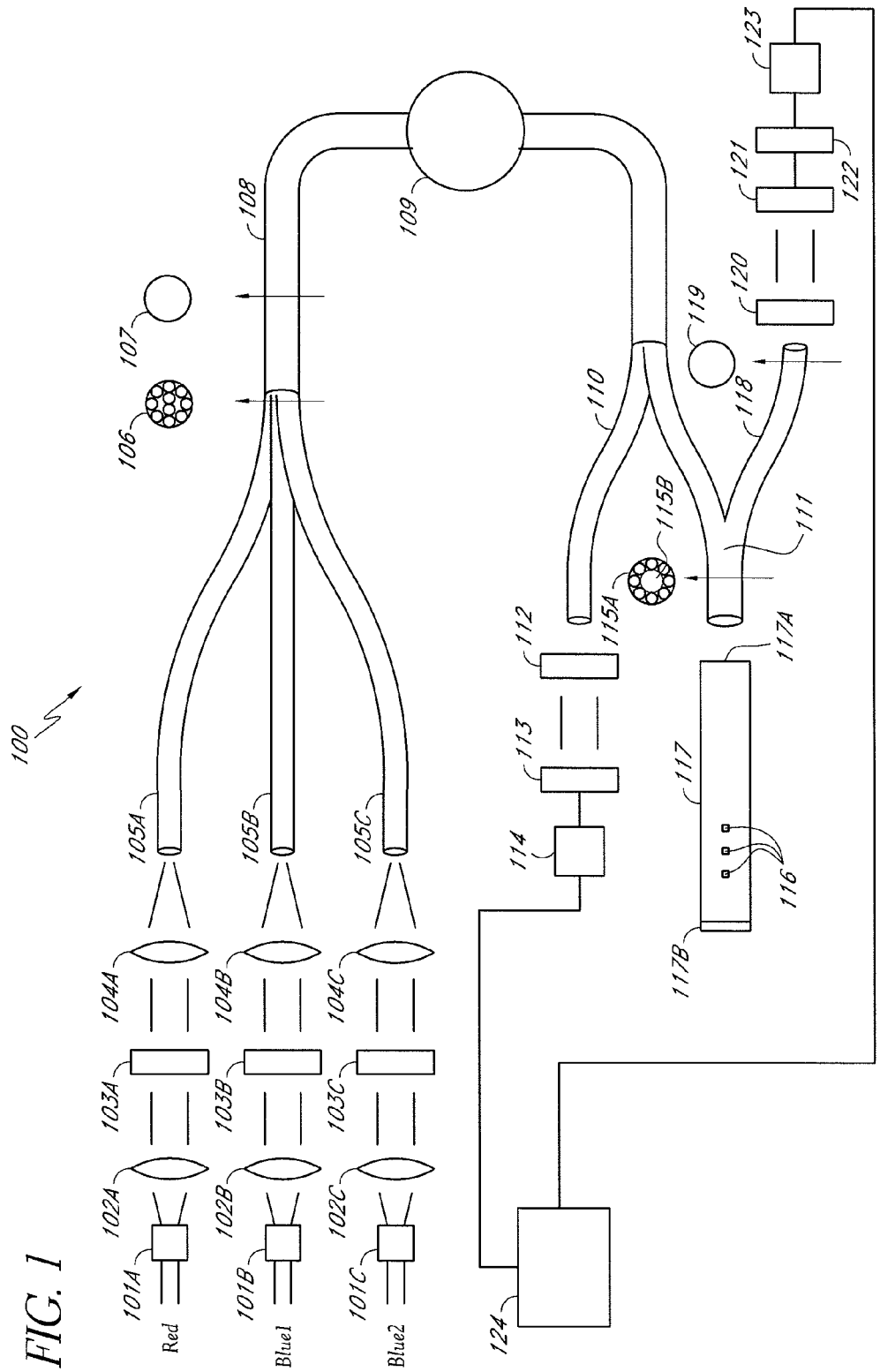
FIG. 1 illustrates an embodiment of a glucose measurement system comprising a mode-stripping scrambler.

In certain embodiments, the optical glucose measurement system measures glucose concentration levels using glucose-sensing chemical indicator systems. Such indicator systems preferably comprise a fluorophore operably coupled to a glucose binding moiety. Preferably, the glucose binding moiety acts as a quencher with respect to the fluorophore (e.g., suppresses the fluorescent emission signal of the fluorophore in response to excitation light when it associates with the fluorophore). In preferred embodiments, as the glucose binding moiety binds glucose (e.g., as glucose concentrations rise), it dissociates from the fluorophore, which then generates a fluorescent emission signal upon excitation. Accordingly, in such embodiments, the higher the glucose concentration, the more glucose bound by the binding moiety, the less quenching, and the higher the fluorescence intensity of the fluorophore upon excitation.

The optical glucose measurement system measures, in certain embodiments, the glucose concentrations intravascularly and in real-time through the use of such fluorophore-quencher indicator systems. The glucose-sensing indicator systems can be immobilized in a hydrogel. The hydrogel can be inserted into an optical fiber such that light may be transmitted through the hydrogel while at least a portion of the hydrogel is in contact with blood. The hydrogel is preferably permeable to blood and analytes, specifically glucose. The optical fiber together with the hydrogels can comprise a glucose sensor that is placed in a mammalian (human or animal) blood vessel. In certain embodiments, light is transmitted into the glucose sensor from a light source. The light source can be a light emitting diode that emits an optical excitation signal. The optical excitation signal can excite the fluorophore systems in the presence of glucose, such that the fluorophores emit light at an emission wavelength. In certain embodiments, the fluorophore systems can be configured to emit an optical emission signal at a first wavelength having an intensity related to the blood glucose concentration in the blood vessel. The light can be directed out of the glucose sensor such that the light is detected by a light sensitive module (or detector system) that can comprise at least one detector. Detectors include any component capable of converting light into a measurable signal, and may include but are not limited to photomultipliers, photodiodes, diode arrays, or the like. The at least one detector can be configured to measure the intensity of the emission wavelength because the intensity of the emission wavelength, in certain embodiments, is related to the glucose concentration present in the blood. In certain embodiments, the light sensitive module (or detector system) comprises an interference filter, an amplifier, and/or an analog-to-digital converter. The light sensitive module (or detector system) can also comprise a microspectrometer, spectrometer, or the like.

Various non-glucose related factors can effect the measurements of the intensity of the emission wavelength, resulting in measurement errors. In certain embodiments, the measurement errors are eliminated or are substantially eliminated or reduced by employing a ratio of certain signals. The measurement errors that may be eliminated include but are not limited to changes in the intensity of the light generated from the light source(s), changes in the coupling efficiency of light into the optical fibers, bending of the optical fiber and the ensuing loss of light from the fiber, changes in the sensitivity of the detection circuit due to, for example, temperature or age or duration of use. In certain embodiments, the ratio of certain signals is unaffected by changes in the light source intensity, the coupling efficiency of the light source into the optical fibers, bending of the optical fibers or the like. The ratio of certain signals can be the ratio of an emission signal to an excitation signal. In certain embodiments, the ratio of certain signals is the ratio of an emission signal to a second optical signal. The second signal may be the excitation light signal which is transmitted through the optical system, through the sensor and indicator system, and reflects back at least in part from the sensor into the light sensitive module (or detector system). Alternatively, the second signal may be generated by a separate reference light, for example red light, which is not absorbed by the indictor system. The second signal may be generated by certain fluorophores as a second emission signal at a different wavelength—the intensity of which is independent of glucose. Any light that is propagated through the optical system, can be either not altered by the glucose concentration or is the excitation light. Light not altered by the glucose concentration can be detected by the light sensitive system (or detector system) and may be used as the second or reference light signal.

From the disclosure herein, it will be apparent to those of ordinary skill in the art that other sources of measurement errors may also be eliminated by employing a ratio of certain of certain signals.

Example 1

Figure 1A:
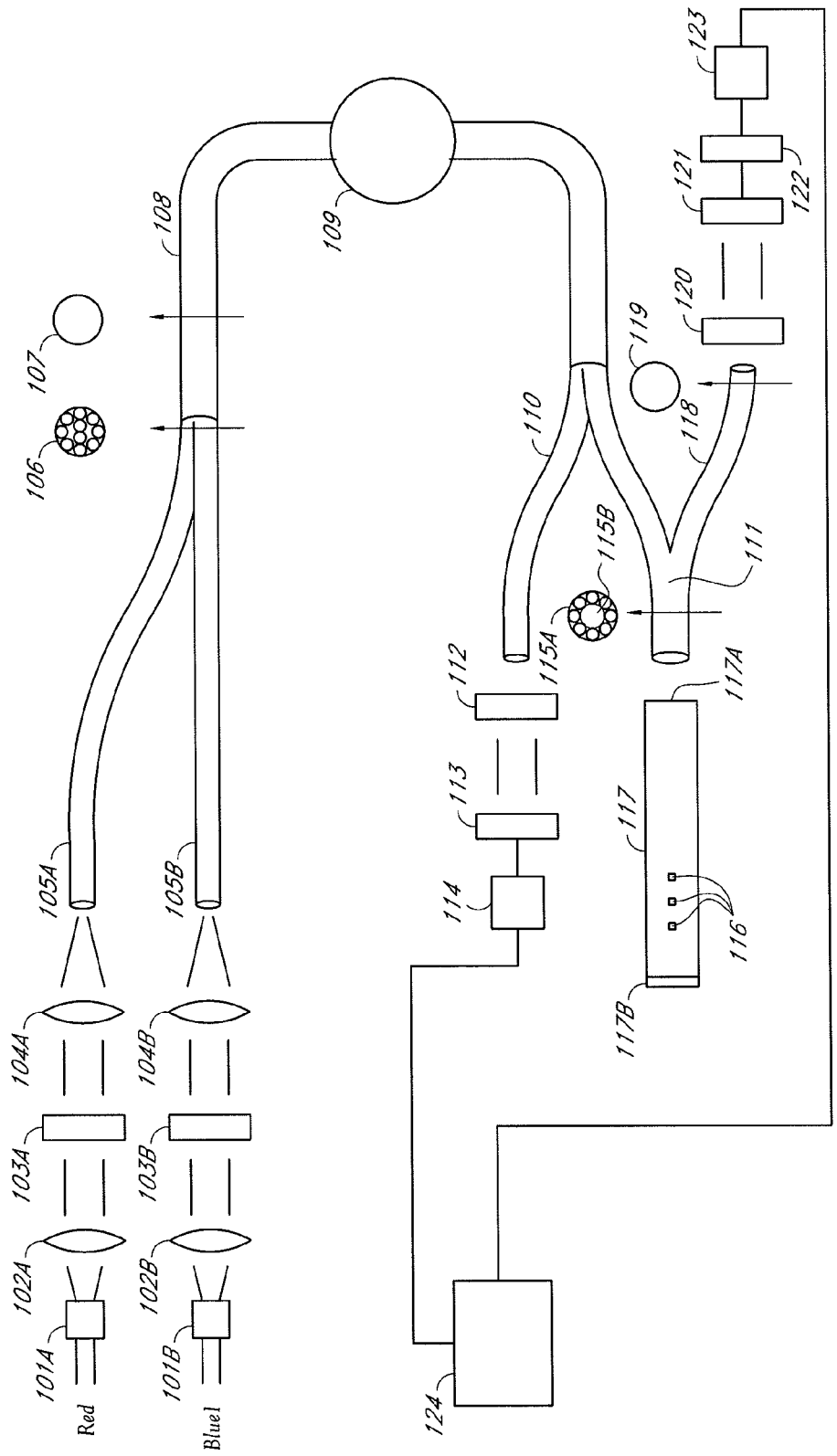
FIG. 1A illustrates an embodiment of a glucose measurement system comprising a mode stripping scrambler with one reference light and one excitation light.

System without a Beamsplitter and Using a Reference Light that does not Cause the Fluorophore to Fluoresce With reference to FIG. 1, the foregoing disclosure applies to certain embodiments comprising at least three light sources. With reference to FIG. 1A, the foregoing disclosure applies to certain embodiments comprising two light sources. In certain embodiments, the light sources 101 are light-emitting diodes (LED's); however, other types of light sources may also be employed. One of the light sources 101A can be a reference light (for example, red) whereas the other two light sources (101B and 101C) are excitation lights having different wavelengths (for example, blue1 and blue2). In certain embodiments, light is transmitted from each of the light sources 101A-C through a optical module comprising a collimator lens 102A-C, an interference filter 103A-C, and/or a focusing lens 104A-C. The light impinging on, transmitting through or striking the interference filter 103 preferably falls within a certain degree of collimation, in order for the interference filter 103 to optimally block light outside the desired band spectrum. The collimator lens 102 can be an aspheric lens but other types of collimator lens may also be employed. The interference filter can be replaced with other types of filters for example wratten filters.

The interference filter 103 can block a portion of the spectrum of each light that is transmitted from the light sources 101. In certain embodiments, the interference filter 103 blocks the portion of spectrum that overlaps with the emission wavelength generated from the fluorophore systems. For example, if a system that employs a blue excitation light to produce a green emission, then an interference filter is preferably used to narrow the band of blue excitation, because the blue excitation light may comprise both blue and green light. An unfiltered excitation blue that comprises green light can produce inaccurate green emission signal because the green light from the excitation light will add to the green emission signal of the fluorophore to produce a green light of greater intensity.

The interference filter 103 can be a short pass filter that blocks all wavelengths beyond a certain point. The interference filter 103 can be a band pass filter that only allows a particular band of wavelengths to pass through the filter. In certain embodiments, the system 100 employs interference filters 102B and 102C that are band pass filters because, in certain embodiments, the excitation lights 101B and 101C have similar wavelengths. The use of two band pass filters can avoid frequency overlap between the two excitation lights, thereby resulting in two excitation lights with two distinct bands.

The use of the interference filter 103 can avoid the wavelength overlap between the excitation and emission wavelengths. In certain embodiments, the resulting light from the interference filters 103A-C can be transmitted through a focusing lens 104A-C. The focusing lens 104A-C directs the light into the respective optical fibers 105A-C. The optical fiber lines 105 may each comprise a single fiber or a bundle of fibers. The use of the fiber bundles can reduce the amount of dead space when the fibers are joined to the single fiber 108. In certain embodiments, each of the fiber optic lines 105 comprises a bundle of fibers that are bundled together to form a fiber bundle 106. The fiber bundle 106 can be connected to a single fiber optic line 108.

A measurement taken across the cross-section of fiber optic line 108 can show an uneven distribution of light. For example, some areas of the fiber may be darker than other areas of the fiber. In certain embodiments, a mode-mixing scrambler 109 is used to distribute the light such that the light is transmitted more uniformly across the optical fiber. The mode-mixing scrambler 109 can be configured to cause the light traveling down the fiber to lose the higher mode light. In certain embodiments, higher mode light is light propagating with large angles of incidence. In certain embodiments, higher mode light with an angle of incidence greater than the critical angle will pass out of the optical fiber. The mode-mixing scrambler 109 can be a length of fiber that is curved around a particular radius to create an optical fiber with a lower critical angle. Light transmitted through the mode-mixing scrambler 109 can result in a low-mode light that tends to travel straighter in the fiber. The single optical fiber 108 can be connected to another fiber optic line 110. The fiber optic line 110 may be a bundle of fibers or a single fiber.

In this embodiment, the light sensitive module (or detector system) comprises two detectors 112, 121. A portion of the light traveling through optical fiber 108 can be transmitted through the fiber optic line 110 and can be measured using the light sensitive module (or detector system) comprising a first detector 112. In certain embodiments, the signal produced from the first detector 112 can be amplified by an amplifier 113. The amplified signal can be converted from an analog signal to a digital signal by the analog-to-digital converter 114. In certain embodiments, the digital signal is transmitted to a data processing device 124 for storage and ratiometric processing. The data processing device 124 can be any data processing device of any type known in the art, for example, microprocessor, embedded processor, multiprocessor, general purpose computer, special purpose processor, computational devices, digital signal processor, microcontroller, programmable gate array or any combinations thereof. In certain embodiments, the single optical fiber 108 is connected to another fiber optic line 111. The fiber optic line 111 may be a bundle of fibers 115 or a single fiber.

A portion of the light traveling through the fiber optic line 108 can be transmitted through the fiber optic line 111 and into the glucose sensor 117. In certain embodiments, the cross-section of line 111 comprises a bundle of fibers 115A placed around a larger single fiber 115B before connecting to glucose sensor 117 at a first end 117A. The glucose sensor 117 can be an optical fiber. In certain embodiments, the glucose sensor has a mirror or reflective surface 117B at a second end of the glucose sensor 117. The fluorophore system of the glucose sensor can be embedded within, immobilized or otherwise associated with hydrogels that reside within holes or cavities 116 in the optical fiber. The fluorophore system can emit a fluorescent light when glucose is present and when the fluorophores are excited by an excitation light 101B, 101C. In certain embodiments, the fluorophore system comprises a dual exciter-single emitter dye (for example, a dye that produces a single emission peak in response to two different excitation lights). Of course other fluorophore systems may be used, including inter alia, single excitation-single emission, dual excitation-dual emission, and single excitation-dual emission).

The emission intensity can be directly related to the glucose concentration (that is, the greater the concentration of glucose, the stronger the intensity of light emitted by the fluorophore system). In certain embodiments, the emission intensity is inversely related to the glucose concentration (that is, the greater the concentration of glucose, the lower the intensity of light emitted by the fluorophore system). A portion of the excitation and emission wavelengths can be transmitted into the fiber optic line 118. The fiber optic line 118 may be a single fiber line, as shown in cross-section 119, or a bundle of optical fibers (not shown). The light transmitted through fiber optic line 118 can be filtered through an interference filter 120. The interference filter 120 can block the excitation lights generated from the light sources 101B and 101C.

The remaining light spectrum comprises emission wavelengths from the fluorophore reporters and the reference light from the light source 101A. In certain embodiments, the remaining light spectrum is measured using the light sensitive module (or detector system) comprising a second detector 121. The signal produced by the second detector 121 can be amplified by an amplifier 122. The amplified signal can be converted from an analog signal to a digital signal by an analog-to-digital converter 123. In certain embodiments, the resulting digital signal is transmitted to computer 124 for storage and ratiometric processing.

The optical glucose measurement system 100 can be configured to pulse light from the light sources 101. For example, the system 100 may transmit light from the reference light source 101A for one second, and then wait one second, and then transmit light from the first excitation light source 101B for one second, and then wait one second, and then transmit light from the second excitation light source 101C for one second and then wait one second before repeating this light pulsation pattern. In certain embodiments, the system 100 would continuously repeat such a light pulsation pattern until the system 100 was turned off. The pulse frequency and duration could vary greatly depending on the desired effect as will be appreciated by one skilled in the art.

The ambient light can affect the intensity of the emission wavelengths. In certain embodiments, the optical glucose measurement system 100 accounts for ambient light effects by taking a first measurement of the light intensity in the system 100 when one of the light sources 101 is on and then taking a second measurement of the light intensity in the system when all the light sources 101 are off. The ambient light effect can be eliminated by subtracting the second measurement from the first measurement.

The bending of the fiber optic lines affects the intensity of the emission wavelengths. The bending of the fiber can create light loss from the fiber optic line. In certain embodiments, the temperature changes affect the performance of the detectors and amplifiers of the system 100, thereby affecting the intensity of the emission wavelength that is detected. There can be factors that affect emission wavelength intensity that do not relate to changes in glucose concentration. To account for the fiber bending, the temperature changing, and other non-glucose related effects on emission wavelength intensity, the system 100 is configured, in certain embodiments, to employ ratiometric calculations to eliminate non-glucose related intensity changes.

The second detector 121 can be configured to measure emission wavelength emitted from the fluorophore system in the sensing cavities 116. In certain embodiments, the detector 121 measures the reference light generated from light source 101A. The fiber bending, the temperature changing, and other non-glucose related factors can affect the intensity of the reference light and the emission wavelength in the same way, thereby allowing ratiometric calculations to eliminate non-glucose related effects on light intensity. The ratiometric calculation employed can involve dividing the measured emission wavelength by the measured reference light, where both measurements are taken at the second detector 121. The ratio of the measured emission wavelength to the measured reference light can cross referenced with a pre-determined function that correlates this ratio to the amount of glucose present. In certain embodiments, the ratio of measured emission wavelength to measured reference light changes only if the glucose concentration changes.

The reference light emitted from light source 101A can be affected by various factors in the system 100, whereas, for example, the first excitation light emitted from light source 101B is unaffected. The system 100 can account for such disparate changes between the reference light and the excitation lights by periodically measuring these lights over time at the first detector 112. In certain embodiments, a ratio is produced that compares the periodic measurements with the first measurement of each light, for example, reference light at time equals zero seconds divided by reference light at time equals one second. A similar ratio can be created for the excitation lights. For example, if the reference light ratio does not equal one then a change occurred in the reference light that should be accounted for before determining the glucose concentration. For example, if a change to the reference light was detected at the first detector 112, then the reference light measured at the second detector 121 should be adjusted to account for this change. For example, if the reference light measurement at the first detector 112 increased then the reference light measured at the second detector 121 must be decreased. In certain embodiments, the decrease is determined by multiplying the measured reference light at the second detector 121 by the following, (reference light at time=0/reference light at time=1), where the reference light measurements were taken from the first detector 112. The same ratiometric calculations can be completed for the emission wavelengths detected at the second detector 121 except that the first and second excitation lights are measured instead of the reference light.

The emission signals and the reference signal can be affected by various factors such that the percent change in all the signals is essentially the same. In certain embodiments these changes can be corrected for by taking the ratio of the emission signal and the reference signal after they are adjusted for changes over time as previously described. Examples of such factors include but are not limited to fiber bending which can result in a loss of light from the fiber.

In certain embodiments, the glucose sensing chemistry is immobilized within the hydrogels in cavities 116. With reference to FIG. 1B, in certain embodiments, the glucose sensor 117 is a solid optical fiber with a series holes drilled straight through the sides of the optical fiber. The holes can be filled with the hydrogels 116. The series of holes that can be drilled through the glucose sensor 117 are in some embodiments evenly spaced horizontally and evenly rotated around the sides of the glucose sensor 117 to form a spiral or helical configuration. The series of holes can also be drilled through the diameter of the glucose sensor. With reference to FIG. 1C, in certain embodiments, the glucose sensor is a solid optical fiber with a series of holes drilled through the sides of the fiber at an angle. The series of holes drilled at an angle, which can be filled with hydrogel 116, are in some embodiments evenly spaced horizontally and evenly rotated around the sides the glucose sensor 117. With reference to FIG. 1D, in certain embodiments, the optical fiber comprises a groove along the length of the optical fiber, wherein the groove is filled with hydrogel 116. The depth of the groove can extend to the center of the optical fiber. In certain embodiments, the groove spirals around the optical fiber. The groove can configured to spiral around the optical fiber to complete at least one rotation. In certain embodiments, the groove spirals around the optical fiber to complete multiple rotations around the optical fiber.

With reference to FIG. 1E, in certain embodiments, the glucose sensor 117 is a solid optical fiber with triangular wedges cut from the fiber. The triangular wedge areas can be filled with hyrdrogel 116. The triangular wedges cut-outs can be evenly spaced horizontally and around the sides of the glucose sensor 117. In certain embodiments, all light traveling in the glucose sensor 117 is transmitted through at least one hole or groove filled with hydrogel.

The hyrdogels can be associated with a plurality of fluorophore systems. The fluorophore systems can comprise a quencher with a glucose receptor site. When there is no glucose present to bind with the glucose receptor, the quencher can prevent the fluorophore system from emitting light when the dye is excited by an excitation light. In certain embodiments, when there is glucose present to bind with the glucose receptor, the quencher allows the fluorophore system to emit light when the dye is excited by an excitation light.

The emission produced by the fluorophore system can vary with the pH of the solution (for example, blood), such that different excitation wavelengths (one exciting the acid form of the fluorophore and the other the base form of the fluorophore) produce different emissions signals. In preferred embodiments, the ratio of the emissions signal from the acid form of the fluorophore over the emission signal from the base form of the fluorophore is related to the pH level of the blood. An interference filter can be employed to ensure that the two excitation lights are exciting only one form (the acid form or the base form) of the fluorophore.

Example 2

System Using a Beamsplitter and a Reference Light Source that does not Cause the Fluorophor to Fluoresce, for Example, a Red Light Source With reference to FIG. 2A, in certain embodiments, the optical glucose measurement system 100 measures glucose concentrations intravascularly and in real-time through the use of fluorophores. In certain embodiments, the optical glucose measurement system 200 comprises at least three light sources as shown in FIG. 2A. The light sources 101 can be light-emitting diodes; however, other types of light sources may also be employed. In certain embodiments, one of the light sources 201A is a reference light (for example, red) whereas the other two lights sources 201B, 201C are excitation lights having different wavelengths (for example, blue1 and blue2). The optical glucose measurement system 200 can be configured to pulse light from the light sources 201 as described above with reference to FIG. 1.

In certain embodiments, light is transmitted from each of the light sources 201 through an optical module comprising a collimator lens 202, an interference filter 203, and/or a focusing lens 204. The resulting substantially collimated light can be transmitted through an interference filter 203 that blocks a portion of the spectrum of each light. The inference filter 203 can block the portion of spectrum that overlaps with the emission wavelengths generated from the glucose sensing fluorophore systems 208, which correspond to the hydrogels 116 as described above with reference to FIG. 1.

The resulting light from the interference filter 203 can be transmitted through a focusing lens 204. The focusing lens 204 can be configured to direct the light into the fiber optic lines 205. The fiber optic lines 205 may each comprise a single fiber or a bundle of fibers. The use of fiber bundles can reduce the amount of dead space when the fibers are joined to the single fiber 206. In certain embodiments, each of the fiber optic lines 205 comprises a bundle of fibers that are bundled together to form a fiber bundle 206. The fiber bundle 206 can comprise a single optical fiber 210 surrounded by fiber optic lines 205. The fiber optic line 210 can comprise a bundle of fiber optic lines.

The fiber bundle 206 can be configured to connect to a first end of a glucose sensor 207. The glucose sensor 207 can comprise a single optical fiber 207A that further comprises a hydrogel 208 as described above in reference to FIGS. 1B, 1C, 1D, and 1E. The glucose sensor 207 can comprise a mirror or a reflective surface 209 that is attached to a second end of the glucose sensor 207. In certain embodiments, the hydrogel 208 comprises fluorophore systems that emit a fluorescent light when glucose is present and when the dyes are excited by an excitation light 201B, 201C. The fluorophore systems can comprise a single exciter-single emitter dye. In certain embodiments, the fluorophore systems comprise a single exciter-dual emitter dye. The fluorophore systems can comprise a dual exciter-single emitter dye. In certain embodiments, the fluorophore systems comprise a dual exciter-dual emitter dye.

The excitation light can be configured to generate from the light sources 201B, 201C and the reference light generated from the light source 201A are transmitted into the glucose sensor. In certain embodiments, the excitation light excites the fluorophore systems when glucose is present. The excitation light, the reference light and the emission light can be reflected off the mirror or reflective surface 209 and into the fiber optic line 210. In certain embodiments, the excitation light, the reference light and the emission light is transmitted into the fiber optic line 210.

The light transmitted through optical fiber 210 can be transmitted through a collimator lens 211. In certain embodiments, the resulting light is substantially collimated, and is transmitted to a beam splitter 212. The beam splitter 212 can be configured to reflect substantially all emission light and substantially all reference light, while transmitting substantially all excitation light.

The beam splitter 212 can be an interference filter that can be designed to work at a substantially forty-five degree angle. In certain embodiments, the beam splitter 212 is a glass surface with a coating that will reflect light having a certain wavelength and allow all other light to pass through the beam splitter 212. The beam splitter can be positioned at a substantially forty-five degree angle relative the direction of the light traveling from the collimator lens 211. In certain embodiments, the beam splitter 212 reflects all of the emission light and a portion of the reference light. The beam splitter 212 can transmit or allow the excitation light and the remaining portion of the reference light to pass through the beam splitter 212. The reference light can have a spectral bandwidth. In certain embodiments, the beam splitter 212 divides the reference spectral band light at a wavelength near the point where the reference light experiences maximum amplitude in order to minimize intensity changes due to spectral shifts in the reference light.

In this embodiment, the light sensitive module (or detector system) comprises two detectors 215A, 215B. The emission light and the portion of reference light that can be reflected by the beam splitter 212 can be measured using the light sensitive module (or detector system) comprising a first detector 215A. In certain embodiments, the signal produced by detector 215A is amplified by amplifier 216A. The amplified signal can be converted from an analog to a digital signal by an analog-to-digital converter 217A. The digital signal can be transmitted to computer 218 for storage and ratiometric processing. In certain embodiments, the excitation light and the portion of the reference light that is transmitted through the beam splitter 212 is measured by a second detector 215B. The signal produced by detector 215B can be amplified by amplifier 216B. In certain embodiments, the amplified signal is converted from an analog to a digital signal by an analog-to-digital converter 217B. The digital signal is transmitted to computer 218 for storage and ratiometric processing.

The optical glucose measurement system 200 can determine the glucose concentration in the blood by taking the ratio of the emission light over the excitation light, wherein the emission light is measured at the first detector 215 and the excitation light is measured at the second detector 216. In certain embodiments, the ratio of the emission light to the excitation light is cross referenced with a pre-determined function that correlates this ratio to the glucose concentration in the blood. The ratio of the emission light to the excitation light is known as the Glucose Ratio. The glucose ratio can, in certain embodiments, be unaffected by changes in the light source intensity, the coupling efficiency of the light source into the optical fibers, bending of the optical fibers or the like. In certain embodiments, the ratio of emission light over excitation light changes only if the glucose concentration changes.

The detectors 215, 216 and the amplifiers 215A, 216A can be affected by various factors, such as temperature, that result in variances in the measured light intensity. These variances created by the two detectors 215, 216 and two amplifiers 215A, 216A can be eliminated or substantially eliminated by taking the ratio of the reference light measured at the first detector 215 and the reference light measured at the second detector 216. In certain embodiments, the foregoing ratio compares the differences between the first detector 215 system and the second detector system 216.

The optical glucose measurement system 200 can determine the ratio of the reference light measured at the first detector 215 and the reference light measured at the second detector 216 at time equals zero, and this ratio is used as a Reference Ratio to compare with measurements taken at subsequent periods. In certain embodiments, a difference between the reference ratio and subsequent ratios indicates that a change has occurred in one of the detectors systems. For example, the foregoing ratio equals to 1/1 at time equals zero, whereas the ratio equals to 1/10 at time equals one. In this example, the two ratios are not equal because the second detector 216 has measured a signal that is ten times the signal that was measured at time equals zero, therefore, to account for this disparity the inverse of the foregoing ratio at time equals one, specifically the ratio of 10/1, is multiplied against the Glucose Ratio.

Example 3

Figure 2B:
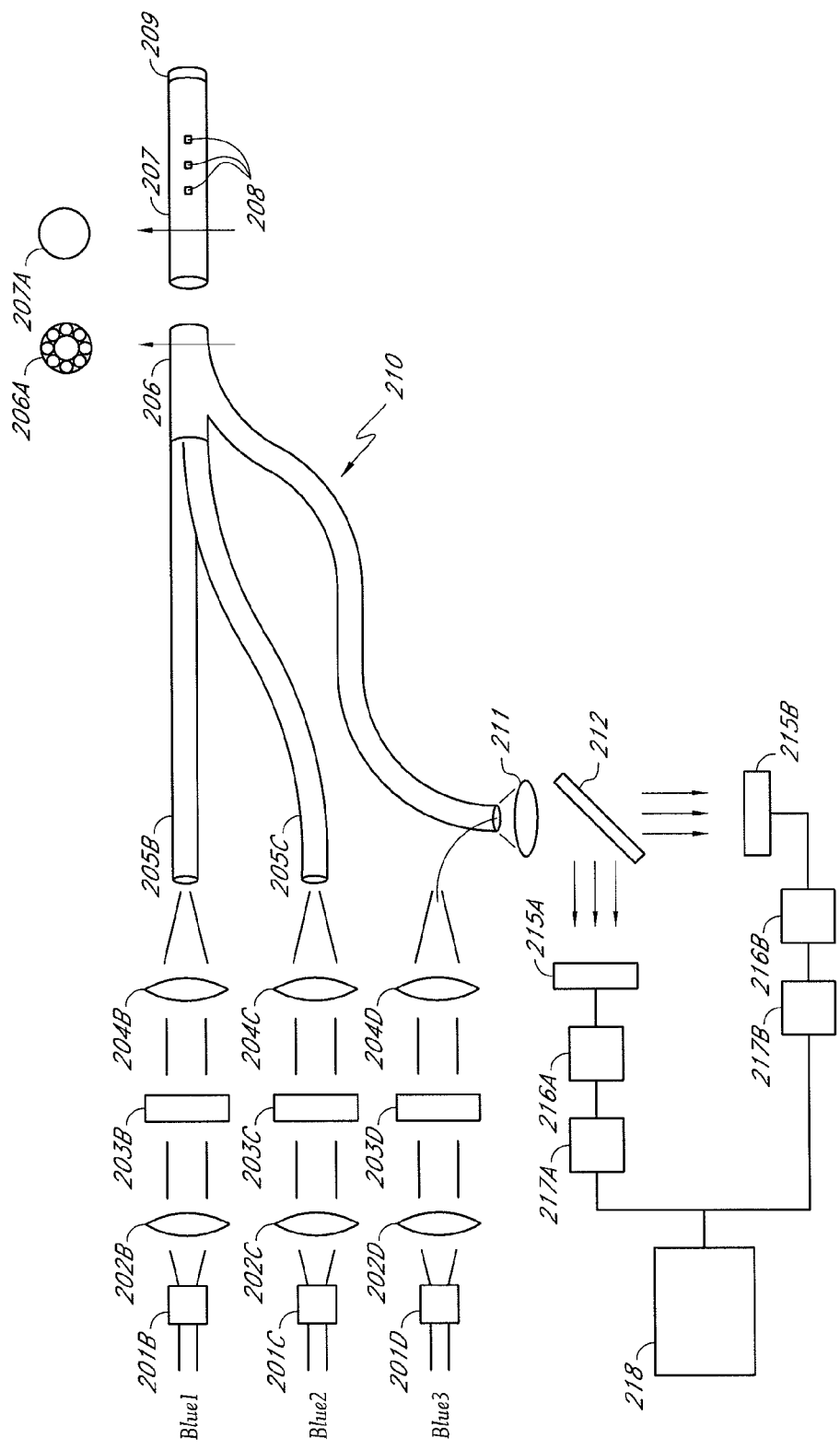
FIG. 2B depicts an embodiment of a glucose measurement system comprising a beam splitter with two light sources transmitting light into the glucose sensor.

System with a Beamsplitter but without a Nonfluoresing (for Example, Red) Reference Light Source With reference to FIG. 2B, certain embodiments comprise at least three light sources 201B, 201C, 201D (for example, blue1, blue2, and blue3). The first excitation light 201B and the second excitation light 201C can be transmitted through collimator lenses 202B, 202C, and interference filters 203B, 203C, and focusing lenses 204B, 204C. In certain embodiments, the light from the light sources 201B, 201C are transmitted through fiber optic lines 205B, 205C, wherein the fiber optic lines may comprise a single optical fiber or a bundle of fibers for the reasons discussed above.

The fiber optic lines 205B, 205C can surround a fiber optic line 210, which is shown in FIG. 206A. In certain embodiments, the fiber optic line 210 may comprise a single optical fiber or a bundle of fiber optic lines. The fiber optic lines 205B, 205C, and 210 can connect to a first end of a glucose sensor 207 wherein the excitation lights can shine through the hydrogels 208 thereby exciting the fluorophore systems immobilized in the hydrogels 208. In certain embodiments, a mirror 209 is attached to a second end of the glucose sensor 207. The emission light and the excitation light can be reflected off the mirror or reflective surface 209 and into fiber optic line 210. The light transmitted by fiber optic line 210 can be directed to collimator lens 211. As described above with reference to FIG. 2A, in certain embodiments, the light resulting from the collimator lens 211 strikes a beam splitter 212 that either reflects the light or allows the light to pass through the beam splitter 212. As described above with reference to FIG. 2A, the wavelengths are detected and measured. As described above with reference to FIG. 2A, the ratio of the reflected light (the emission light) over the transmitted light (the excitation light) can be related to glucose concentrations in the blood. In certain embodiments, the foregoing ratio is known as the Glucose Ratio.

Similar to the embodiment described above with reference to FIG. 2A, the Glucose Ratio can be adjusted by ratiometric calculations. As described in FIG. 2A above, the embodiment depicted in FIG. 2B comprises a light sensitive module (or detector system) comprising two detectors that may be affected by various factors in different ways. Therefore, ratiometric calculations can be employed to eliminate non-glucose related light intensity changes. In certain embodiments, a third light source 201D can be used to provide a reference signal used in the ratiometric calculations.

The light generated by the light source 201D can be transmitted through a collimator lens 202D. In certain embodiments, a focusing lens 204D focuses the resulting light from the collimator lens 202D into a optical fiber 210 which transmits the light through collimator lens 211. The light generated by the light source 201D can comprise two colors of different wavelengths. The two colors can be the same as the excitation light and the emission wavelength. For example, in a system where the excitation light is blue and the emission wavelength is green, then light generated by the light source 201D is a blue light comprising both blue and green light. In certain embodiments, the beam splitter 212 will reflect the green light while allowing the blue to pass through the lens. The reflected green light can be measured at detector 215A and the transmitted light is measured at detector 215B.

Ratiometric calculations can be performed by taking the ratio of the reflected light over the transmitted light at time equals zero, wherein this ratio is used as a reference ratio. In certain embodiments, the foregoing ratio is taken at subsequent times and compared to the reference ratio. Where subsequent ratios do not equal the reference ratio, the inverse of the subsequent ratio can be multiplied against the Glucose Ratio, as described above with reference to FIG. 2A.

Example 4

System where the Beam Splitter is Replaced with a Beam Splitting Polarizer

The systems described above may be augmented, in certain embodiments, by substituting the beam splitter 212 as described above with a beam splitter that reflects s-polarized light towards the first detector 215A in the light sensitive module while allowing p-polarized light to pass through the beam splitter 212 and to the second detector 215B in the light sensitive module. In certain embodiments, an interference filter is placed before the first detector 212 that blocks all excitation light before transmitting the remaining light (emission light and reference light) to first detector 215A. An interference filter can be placed before the second detector 215B that blocks all emission light before transmitting the remaining light (excitation light and reference light) to the second detector 215B. The disadvantage of this system is that some of the emission and excitation signals are not being fully measured.

Figure 2C:
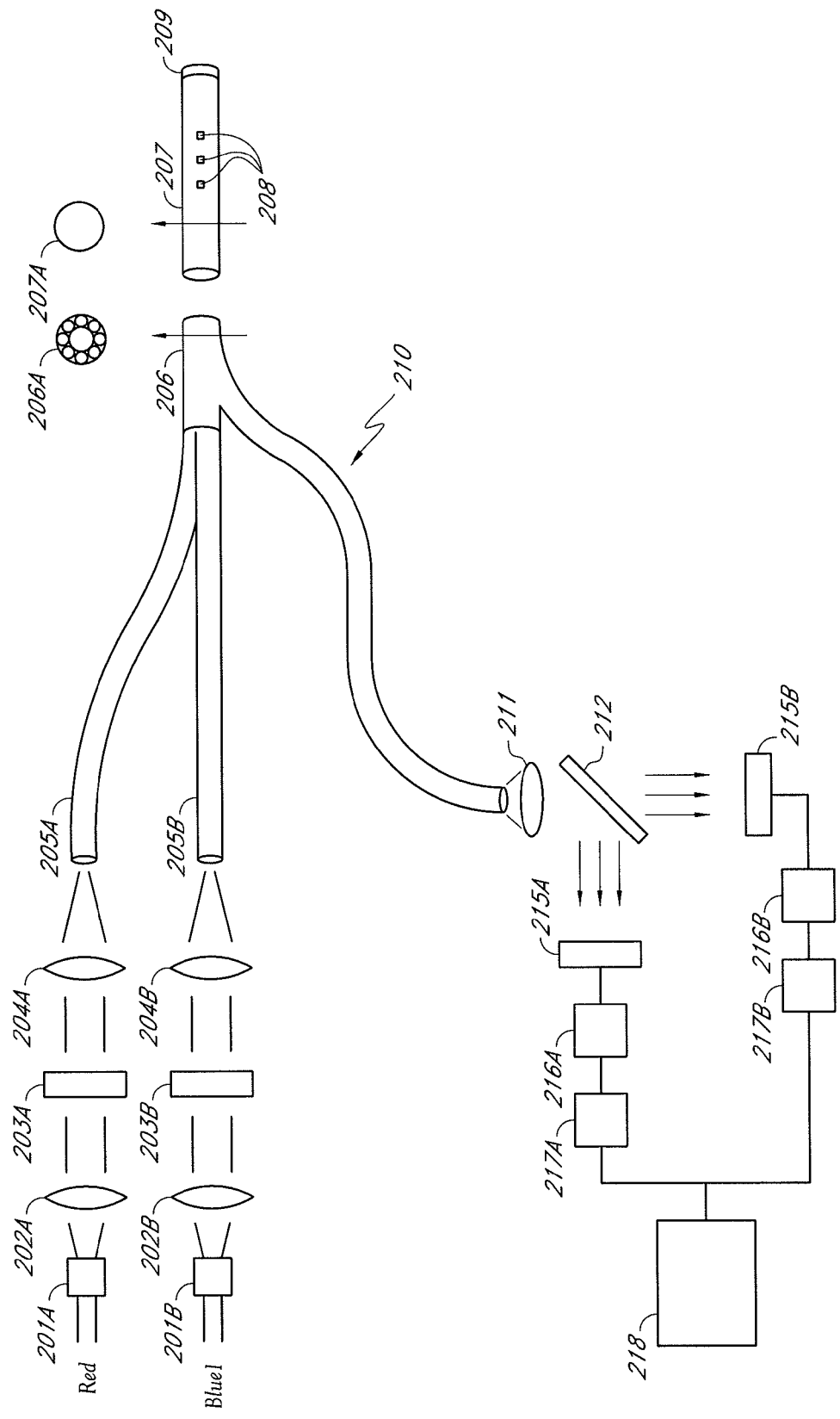
FIG. 2C is a glucose measurement system embodiment comprising a beam splitter with one excitation light source and one reference light source transmitting light into the glucose sensor.

The systems described above, with reference to FIG. 2A, may be augmented to include only two light sources 201A, 201B and the corresponding optical module comprising collimator lenses, interference filters, and focusing lenses, as shown in FIG. 2C or to include more than three light sources (figure not shown). The systems described above with reference to FIGS. 2A and 2B and 2C, in certain embodiments, can be augmented by partially coating the mirror 209 with a paint that partially absorbs the reference light to compensate for the saturation of reference light at the first detector 215A.

Example 5

Describes Ways to Deal with Large Intensity Differences Between the Various Signals The systems described above with reference to FIGS. 2A and 2B and 2C produce relatively small amounts of emission light relative to the amount of excitation light. To compensate for these disparate signal intensities, in certain embodiments, the amplifier gain for the first amplifier 216A can be set higher than the amplifier gain for the second amplifier 216B6. In certain embodiments, the beam splitter 212 is configured to transmit more reference light through the beam splitter in order to compensate for the high gain amplification at amplifier 216. Instead of adjusting the beam splitter 212 as described above, an interference filter can be employed to block a portion of the reference light transmitted to the first detector 215A in order to compensate for the high gain amplification at the amplifier 216A.

Example 6

System Using a Spectrometer in Place of a Beam Splitter

Figure 3:
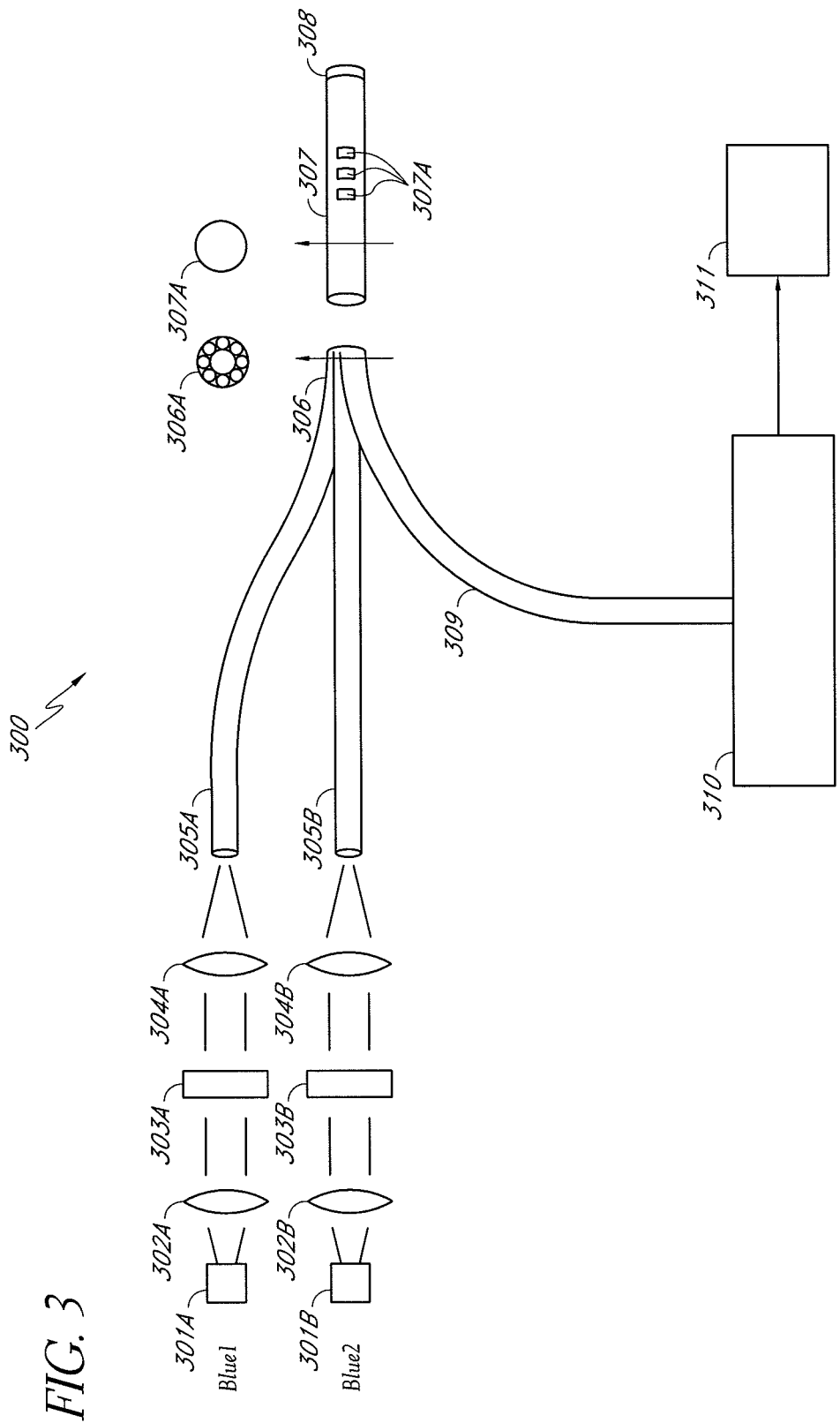
FIG. 3 illustrates an embodiment of a glucose measurement system comprising two excitation light sources and a microspectrometer and or spectrometer.

With reference to FIG. 3, certain embodiments comprise at least two light sources. In certain embodiments, the light sources 301 generate excitation light that is transmitted through a optical module comprising a collimator lens 302, an interference filter 303, and/or a focusing lens 304. The resulting light from collimator lens 302 can be transmitted to interference filters 303. The resulting light from interference filters 303 can be focused by focusing lens 304 into fiber optic lines 305. In certain embodiments, fiber optic lines may be a single fiber or a bundle of fibers surrounding optical fiber 309. The fiber optic line 309 may be a single fiber or a bundle of fibers. The fiber optic lines 305, 309 can be bundled together at junction 306 and are connected at glucose sensor 307. As described above with reference to FIG. 3, the glucose sensor 307 can comprise hydrogels 307A.

The emission light and the excitation lights can be transmitted from the glucose sensor into the fiber optic line 309, as described above with reference to FIG. 2. In certain embodiments, the fiber optic line 309 is connected to a light sensitive module comprising a microspectrometer 310 that measures the entire spectrum of light in the glucose measurement system 300. The ratio of emission light over the corresponding excitation light can be related to the concentration of glucose as described above with reference to FIG. 2. As described above with reference to FIG. 2, the ratio of the emissions light (for example, the acid form) produced by the first excitation light over the emission light (for example, the base form) produced by the second excitation light can be related to pH levels in the test solution, for example blood.

The microspectrometer can be the UV/VIS Microspectrometer Module manufactured by Boehringer Ingelheim. Any microspectrometer can be used. Alternatively, the microspectrometer could be substituted with other spectrometer, such as those manufactured by Ocean Optic Inc.

In certain embodiments described above, the ratiometric calculations require measurements of various light intensities. These measurements can be determined by measuring the peak amplitudes at a particular wavelength or wavelength band. These measurements can be determined by calculating the area under the curve between two particular wavelengths as for example with the output from a microspectrometer.

The use of a microspectrometer and/or spectrometer can allow the glucose measurement system 300 to be easily changed when different fluorophore systems are employed. For example, if the system 300 is manufactured with a fluorophore system that emits a green emission wavelength and if later research and development shows that a fluorophore system that emits a red emission wavelength is better at detecting glucose concentrations, then in such a situation one would only need to replace the glucose sensor and the software to perform the ratiometric calculations. In such an example, one would not need to change interference filters or beam splitters.

Example 7

Figure 3A:
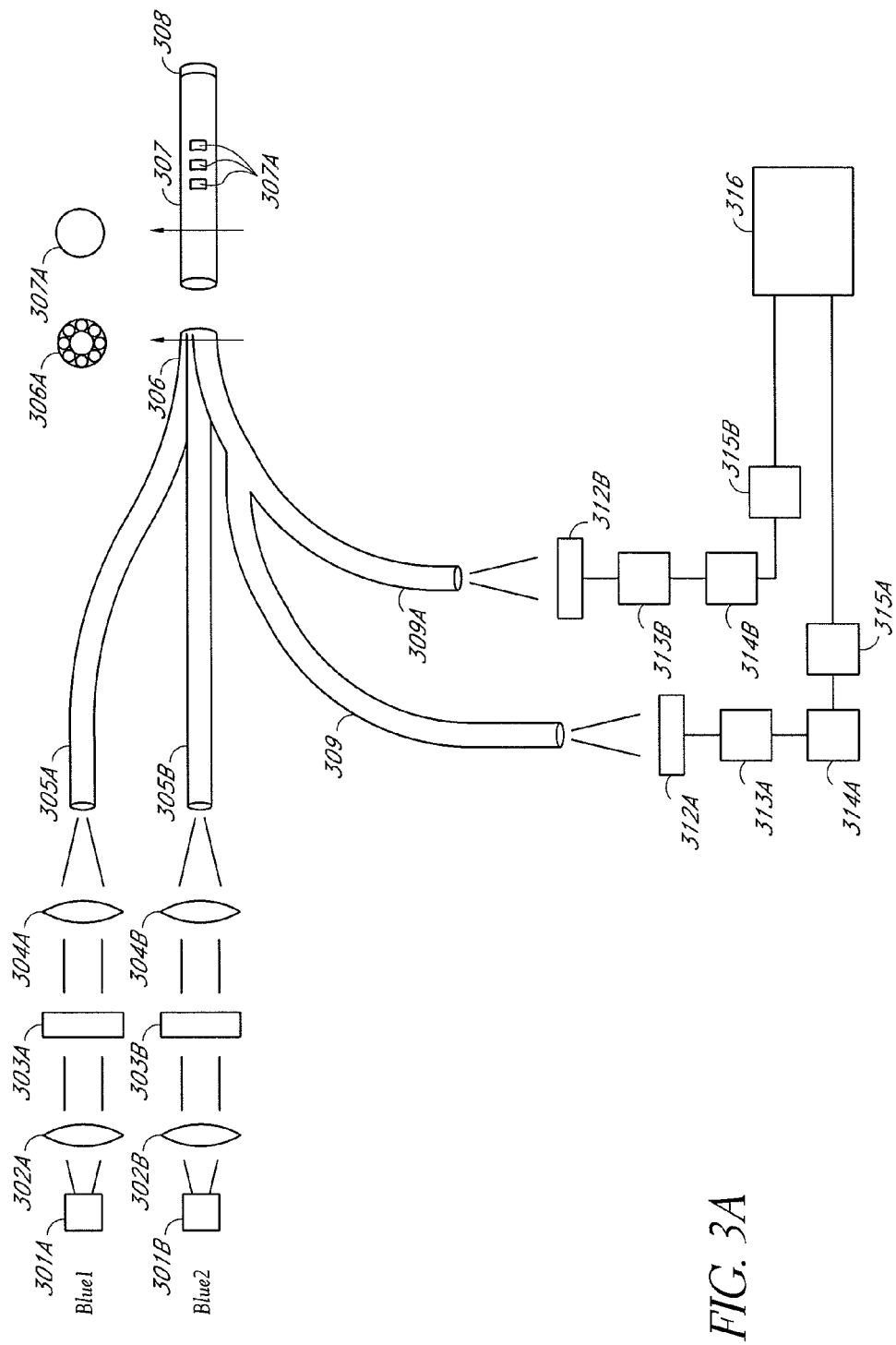
FIG. 3A is an embodiment of a glucose measurement system comprising two excitation light sources and two detectors.
Figure 3B:
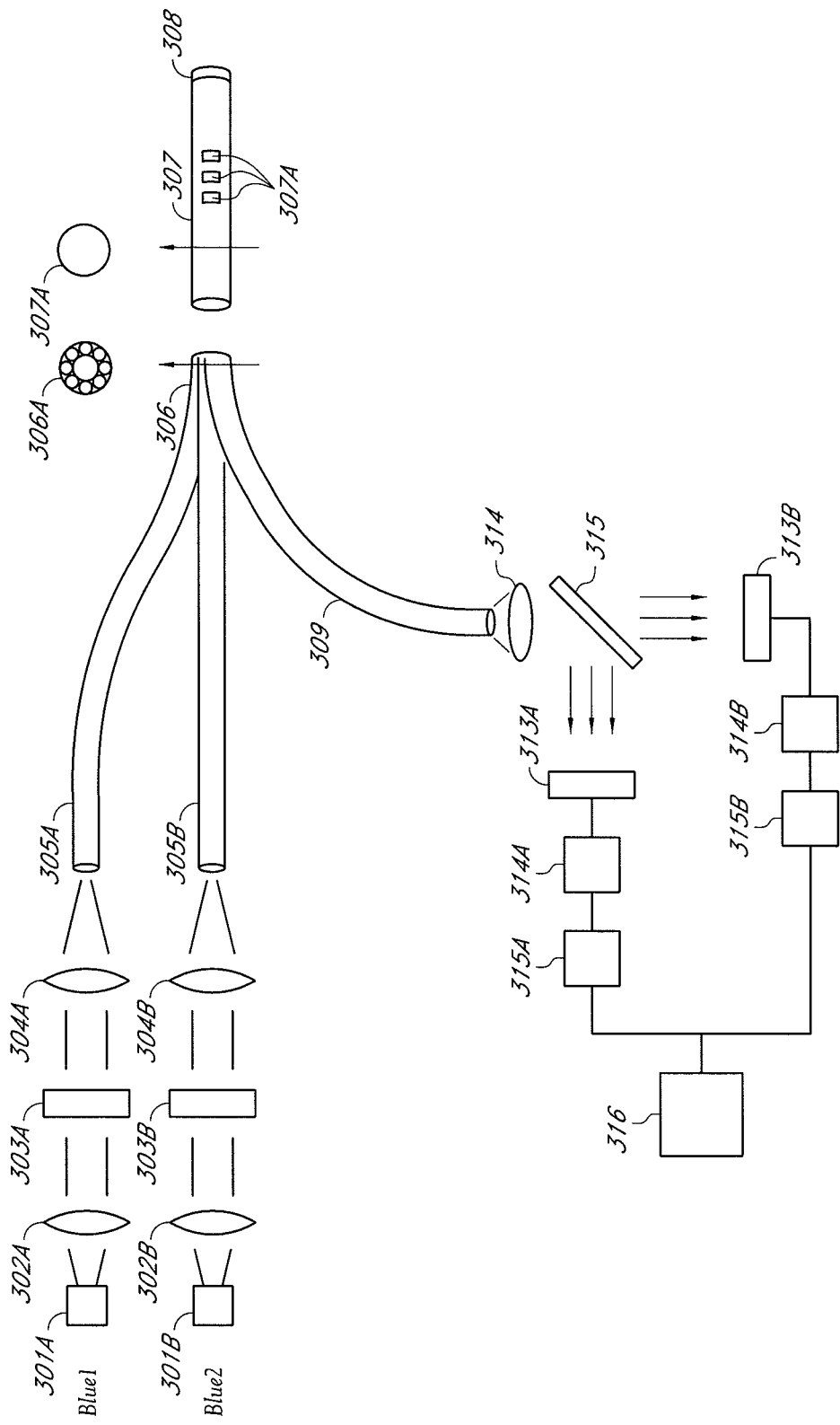
FIG. 3B illustrates a glucose measurement system embodiment comprising two excitation light sources and two detectors and a beam splitter.

System without Microspectrometer—Uses a Beam Splitter or at Least Two Fibers Going Directly to the Two Detectors The systems described above with reference to FIG. 3 can be augmented by comprising a light sensitive module comprising two interference filters 312A, 312B and two detectors 313A, 313B as shown in FIG. 3A. In certain embodiments, substantially half of the emission light and half of the excitation light are transmitted from the glucose sensor into the fiber optic line 309 and the remainder of the emission light and the excitation lights are transmitted from the glucose sensor into the fiber optic line 309A. The interference filter 312A can be configured to block the excitation lights and allow the emission light to pass to detector 313A where the emission light is measured. The signal produced by the detector 313A can be amplified by the amplifier 314A and converted into a digital signal by analog-to-digital converter 315A and transmitted to computer 316. The interference filter 312B can be configured to block the emission light and allow the excitation lights to pass to detector 313B where the excitation light is measured. In certain embodiments, the signal produced by the detector 313B can be amplified by the amplifier 314B and converted into a digital signal by analog-to-digital converter 315B and transmitted to computer 316. Similar to the above disclosure referring to FIG. 1, ratiometric calculations can be employed to substantially eliminate or reduce non-glucose related factors affecting the intensity of the measured emission light and measured excitation light. In certain embodiments, the measured emission light is divided by the measured excitation light, wherein such calculations substantially eliminate or reduce non-glucose related factors affecting the intensity of the lights. Alternatively, the bifurcated fibers 309, 309A can be substituted with a single fiber or fiber bundle 309 and a beam splitter 315, as illustrated for example in FIG. 3B.

Example 8

Figure 4:
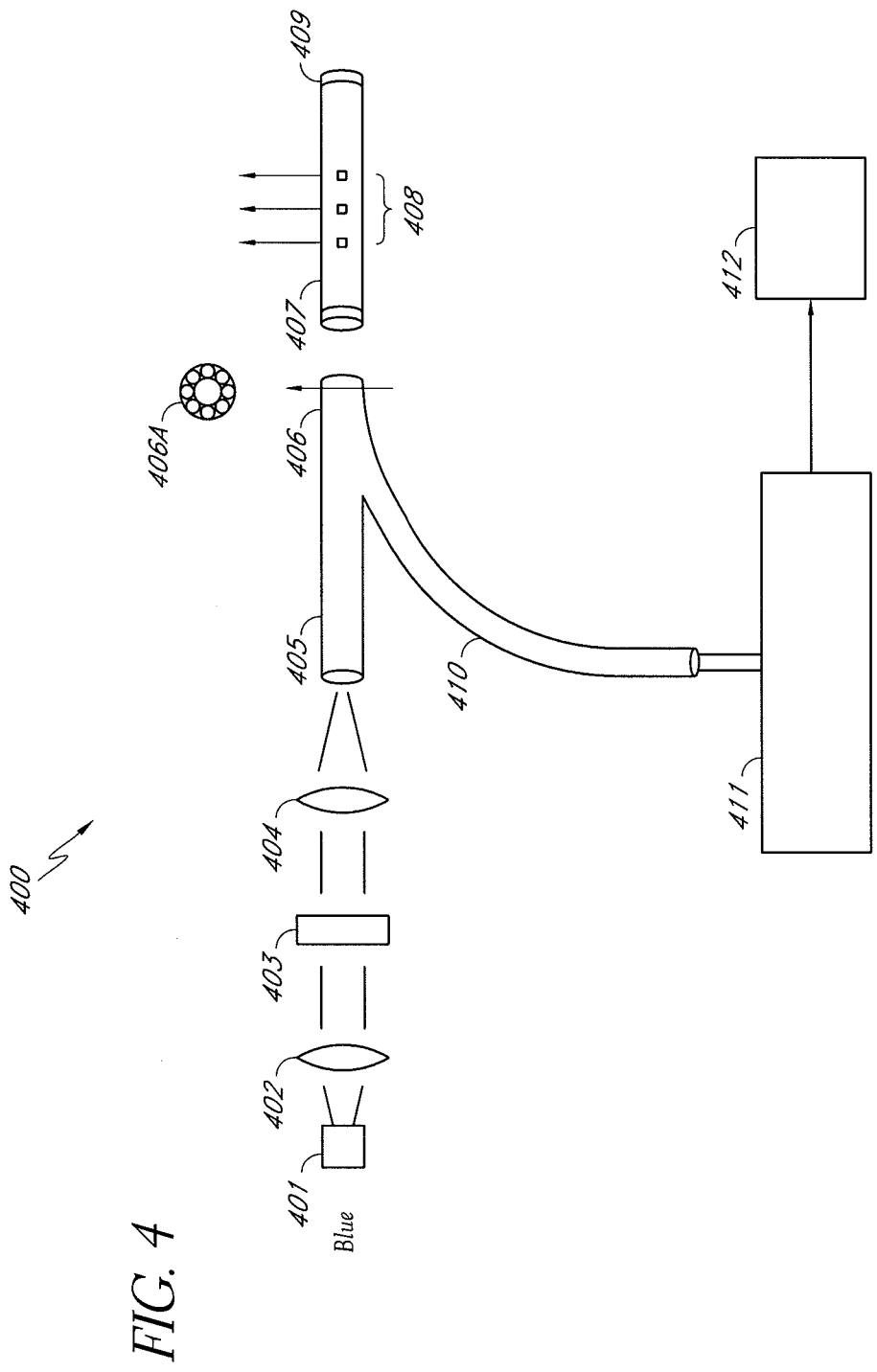
FIG. 4 depicts an embodiment of a glucose measurement system comprising one excitation light source, a single exciter-dual emitter fluorophore system, and a microspectrometer and or spectrometer.

System Using a Spectrometer in Conjunction with a Single Exciter and Dual Emitter Fluorophore The systems described above with reference to FIG. 3 can be augmented by including only one light source, and a fluorophore system that is a single exciter, dual emitter fluorophore system. With reference to FIG. 4, in certain embodiments, the light generated by the single light source 401 is transmitted through a optical module comprising a collimator lens 402, an interference filter 403, and/or a focusing lens 404 as described above. The resulting light can be filtered through an interference filter 403. The resulting light can be focused by a focusing lens 404 into a fiber optic line 405, which may be a single fiber or a bundle of fibers. The fiber optic line 405 can surround a fiber optic line 410 as both fiber optic lines connect to the first end of the glucose sensor 407. In certain embodiments, a mirror or reflective surface 409 is attached to the second end of the glucose sensor 407. The fiber optic line 410 may be a single fiber or a bundle of fibers. The glucose sensor can comprise hydrogels that further comprise a fluorophore system that produces two emission wavelengths, a first emission wavelength and a second emission wavelength. In certain embodiments, the fluorophore system is excited by the light generated by light source 401. In certain embodiments, the fiber optic line 410 is connected to a light sensitive module comprising a microspectrometer 411 that measures the entire spectrum of light in the glucose measurement system 400. Data from the microspectrometer 411 can be transmitted to computer 412 for processing. The microspectrometer 411 can allow system 400 to simultaneously measure the excitation light intensity as well as both emission light intensities. Similar to the above disclosure referring to FIG. 1, ratiometric calculations are employed to substantially eliminate or reduce non-glucose related factors affecting the intensity of the measured emission light and measured excitation light. The measured emission light can be divided by the measured excitation light, wherein such calculations substantially eliminate or reduce non-glucose related factors affecting the intensity of the lights.

The first emission wavelength can be related to the concentration of acid in the blood. In certain embodiments, the second emission wavelength is related to the concentration of base in the blood. The ratio of intensities of the first emission light over the second emission light can be related to the pH level of the blood. As described above with reference to FIG. 2, the ratio of the first emission light over the excitation light can be related to the glucose concentration in the blood. As described above with reference to FIG. 2, the ratio of the second emission light over the excitation light can be related to the glucose concentration in the blood.

Example 9

System Using Two Fluorophores, One as a Glucose and pH Indicator the Other as a Reference, in the Same Gel The systems described above with reference to FIGS. 3, 3a, 3b, and 4 can be augmented, as shown in FIGS. 5, 5a, 5b and 6 by immobilizing two fluorophore systems in the hydrogels 509, 510, and by not attaching a mirror or other reflective surface at the second end of the glucose sensor 508 (for example, mirror or reflective surface 511 in FIGS. 5, 5a, 5b, and 6 is not a feature in these foregoing embodiments). With reference to FIGS. 5, 5a, 5b, and 6 in certain embodiments, a portion of the light that is transmitted into the glucose sensor 508 is reflected back and into fiber 512. Another portion of the light that is transmitted into the glucose sensor 508 can be transmitted through the glucose sensor 508 and into the blood stream. A portion of the light that is transmitted into the blood stream can be reflected off of various particles in the blood and back into the glucose sensor 508. Accordingly, the intensities of the excitation and emission signals as well as the ratio of the excitation and emission signals are varying over time in response to various parameters other than changes in glucose (for example, varying degrees of excitation light re-entering the glucose sensor 508). In certain embodiments, these changes are accounted for by using a reference light produced by a second fluorophore system.

Figure 5:
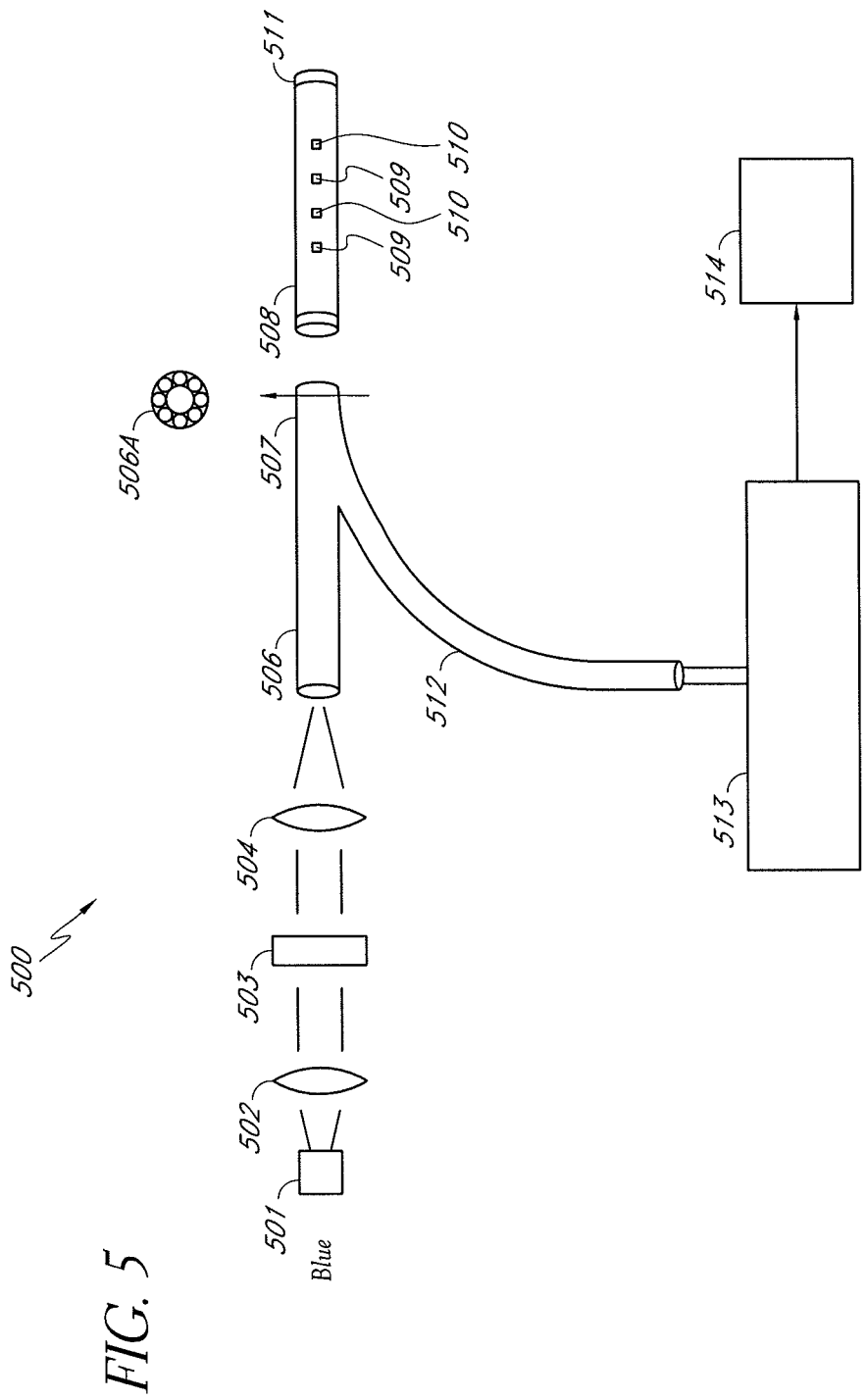
FIG. 5 is an illustration depicting a glucose measurement system embodiment comprising one excitation light source, two fluorophore systems, and a microspectrometer and or spectrometer.
Figure 5A:
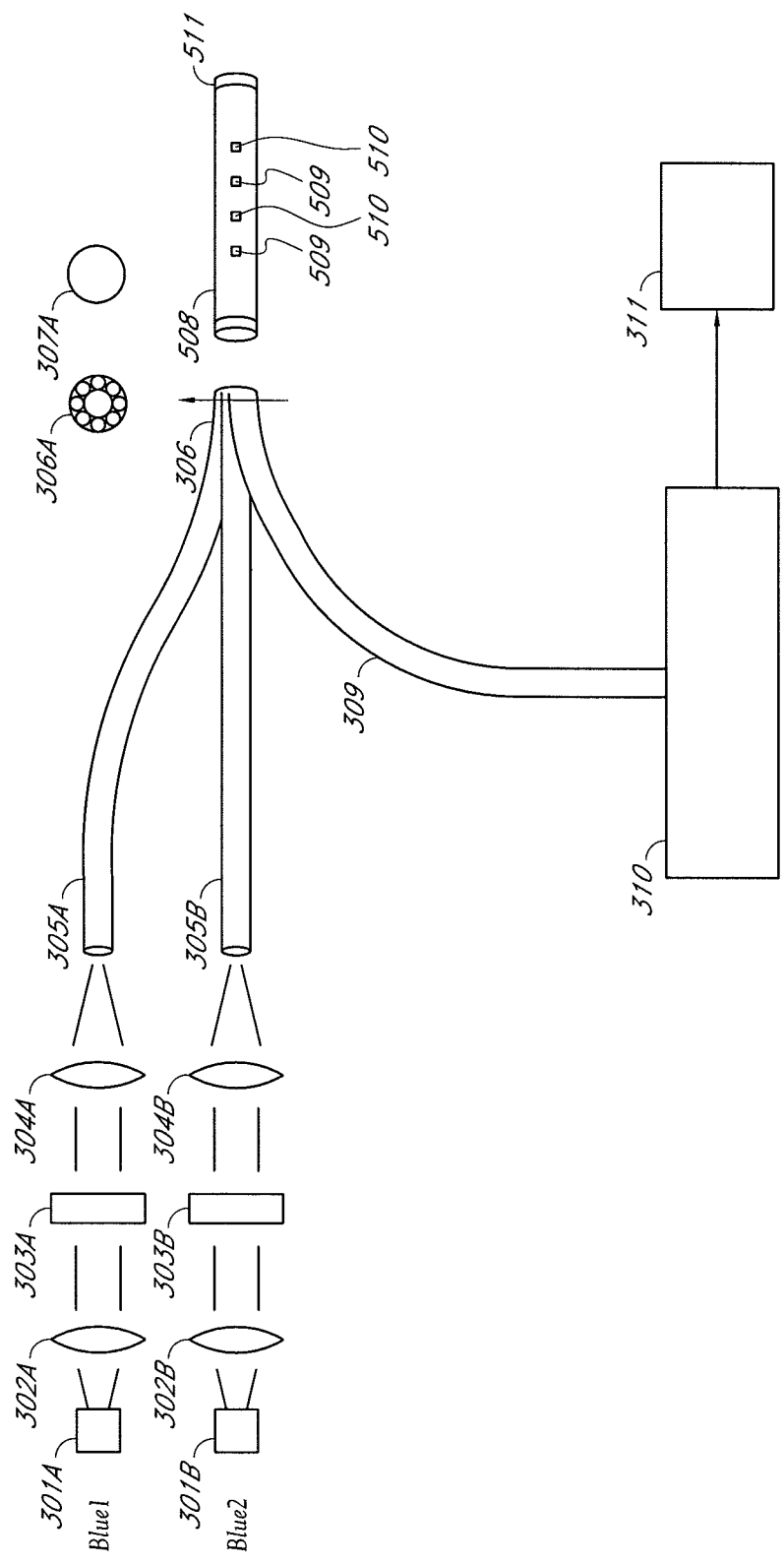
FIG. 5a is an illustration depicting a glucose measurement system embodiment comprising two excitation light sources, two fluorophore systems, and a microspectrometer and or spectrometer.
Figure 5B:
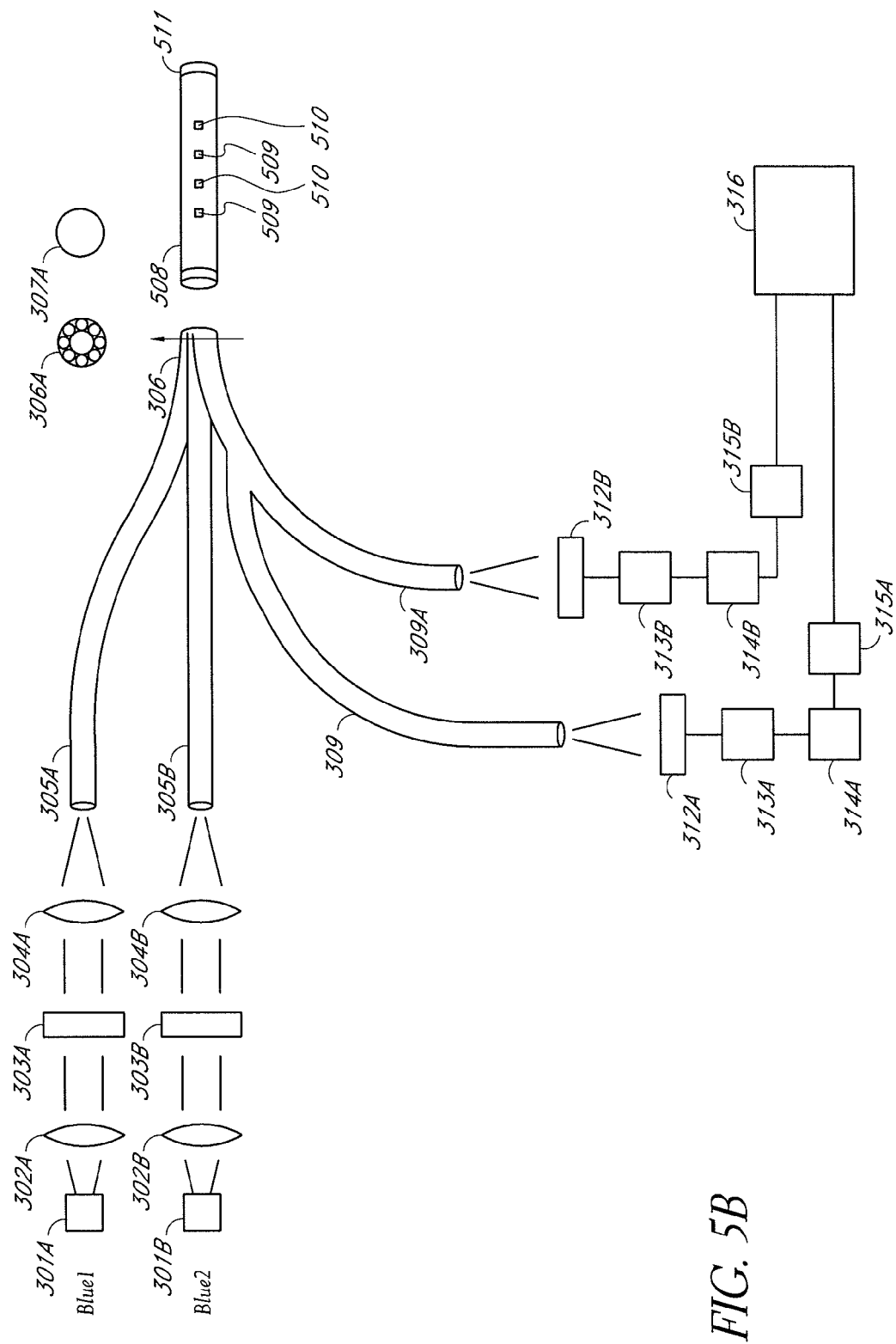
FIG. 5b is an illustration depicting a glucose measurement system embodiment comprising two excitation light sources, two fluorophore systems, two detectors, and bifurcated fiber optic line.

With reference to FIG. 5, in certain embodiments, for example where the first fluorophore is a single exciter, dual emitter, the first fluorophore system produces a first and a second emission light intensity in response to a first excitation light, that is related to glucose and pH, as described above with reference to FIG. 4. With reference FIGS. 5a, 5b, and 6 in certain embodiments, for example where the first fluorophore is a dual exciter, single emitter, the first fluorophore system produces a first and second emission light intensity in response to a first and second light, that is related to glucose and pH, as described above with reference to FIGS. 3, 3a, and 3b. The second fluorophore system can produce a third emission wavelength that does not change with glucose concentration changes or pH level changes and it excites at least one of the same excitation wavelengths as the first fluorophore system. The third emission wavelength can be used as a reference light. The ratio of the first emission light over the reference light can produce a ratiometric corrected ratio that is related to glucose and is independent of light source intensity changes, coupling efficiency and fiber bending. In certain embodiments, the ratio of the second emission light over the reference light produces a ratiometric corrected ratio that is related to glucose and is independent of light source intensity changes, coupling efficiency and fiber bending. The ratio of these two ratios can be related to the pH and is independent of the light source intensity, coupling efficiency, fiber bending, and the concentration of the first fluorophore. In certain embodiments, the systems described above with reference to FIGS. 5, 5a, 5b and 6 comprises a mirror 511 attached at the second end of the glucose sensor 508.

Example 10

System where the Use of the Two Fluorophore System Above can be Employed so as to Eliminate the Need for Holes in the Fiber and a Mirror The systems described above with reference to FIGS. 5, 5a, 5b and 6 can be augmented to exclude a mirror at the second end of the glucose sensor and the holes in the sensor (509 and 510) and to include a tubular permeable membrane or some other means of containing and attaching a uniform hydrogel mixture to the end of the fiber comprising two fluorophore systems as described above with reference to FIGS. 5 5a, 5b and 6. In certain embodiments, the tubular permeable membrane or container means resembles a receptacle or pouch or sack for containing a uniform hydrogel mixture. Alternatively, the end of the glucose sensor fiber 508 can also comprise a cavity or receptacle formed within the end of the fiber, wherein the cavity or receptacle is configured to contain the hydrogel mixture.

Example 11

System where the Second Fluorophore is not in the Gel, but is Coated on the Mirror and the Mirror Embedded into the End of the Fiber. This Allows the Second Fluorophore to be Sensitive to pH and Other Analytes (that is, a Larger Number of Fluorophores to Choose from) Since it is Isolated from the Blood by being Embedded in the End of the Fiber With reference to FIGS. 5, 5a, 5b and 6, in certain embodiments the systems described above are augmented to include a mirror 511 that is at least partially coated with a second dye. The second dye can be a reference dye as described above with reference to FIGS. 5, 5a, 5b, and 6. As previously described, the second dye is preferably not sensitive to changes in glucose and pH levels in the blood when the second dye is immobilized in the hyrdrogels that are exposed to the blood. To avoid exposing the second dye to the blood, in certain embodiments, the mirror 511 is at least partially coated with a second dye and embedded in the end of the fiber. In this embodiment the intrinsic insensitivity of the second dye to glucose, pH or any other blood constituents is not required.

Example 12

Figure 7:
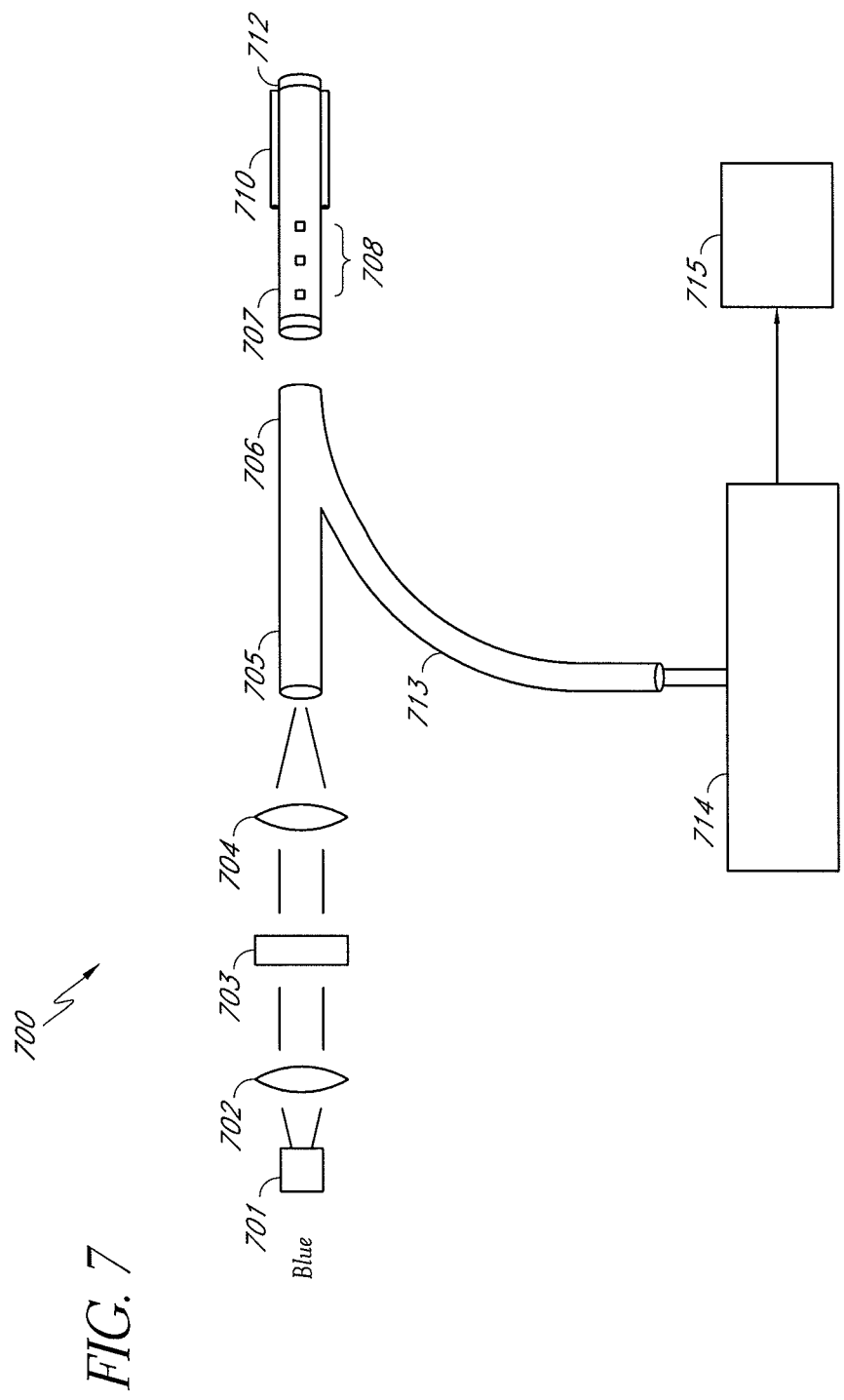
FIG. 7 illustrates an embodiment of a glucose measurement system comprising a colored optical fiber attached to the glucose sensor.

System as in Example 11 but Instead of a Mirror Coated with the Reference Fluorophore the Fluorophore is Embedded into a Second Optical Fiber which is Attached to the End of the First Optical Fiber The systems described above with reference to FIGS. 5, 5a, 5b and 6 can be augmented to include a second fiber. With reference to FIG. 7 for example, in certain embodiments, the second fiber 610 is attached to the second end of the glucose sensor, wherein the second fiber is embedded with a fluorophore. When light is shown through the second fiber the fiber can be configured to emit a second emission wavelength. The second fiber can be hydrophobic and as such the embedded fluorophore is not exposed to changes in the blood, for example pH or glucose concentration. The embedded dye can be a reference dye as described above with reference to FIGS. 5, 5a, 5b, and 6. In this embodiment, the intrinsic insensitivity of the second dye to glucose, pH or any other blood constituents may not be required.

Example 15

System where the Spectrometer is Replaced with Two Beam Splitter in Series Allowing the Separate Detection of Up to Three Different Wavelength Bands. For Example with a Single Exciter and Dual Emitter Fluorophore Both Emission Signals as Well as the Excitation Signal can be Measured. With a Two Fluorophore System Again Both Emission as Well as the Excitation Signal can be Measured The systems described above with reference to FIGS. 4, 5, and 7 may substitute the microspectrometer or spectrometer with a beam splitter as described above with reference to FIGS. 2A and 2B. The systems described above with reference to FIGS. 4, 5, and 7 may substitute the microspectrometer (or spectrometer) in the light sensitive module with two beam splitters such that for example, a first beam splitter reflects excitation light to a first detector and then a second beam splitter reflects emission wavelengths to a second detector, while allowing all remaining wavelengths (for example, a second emission wavelength or reference light) to pass through the two beam splitters and into a third detector. In certain embodiments, ratiometric calculations would be employed as described above.

Example 16

Figure 6:
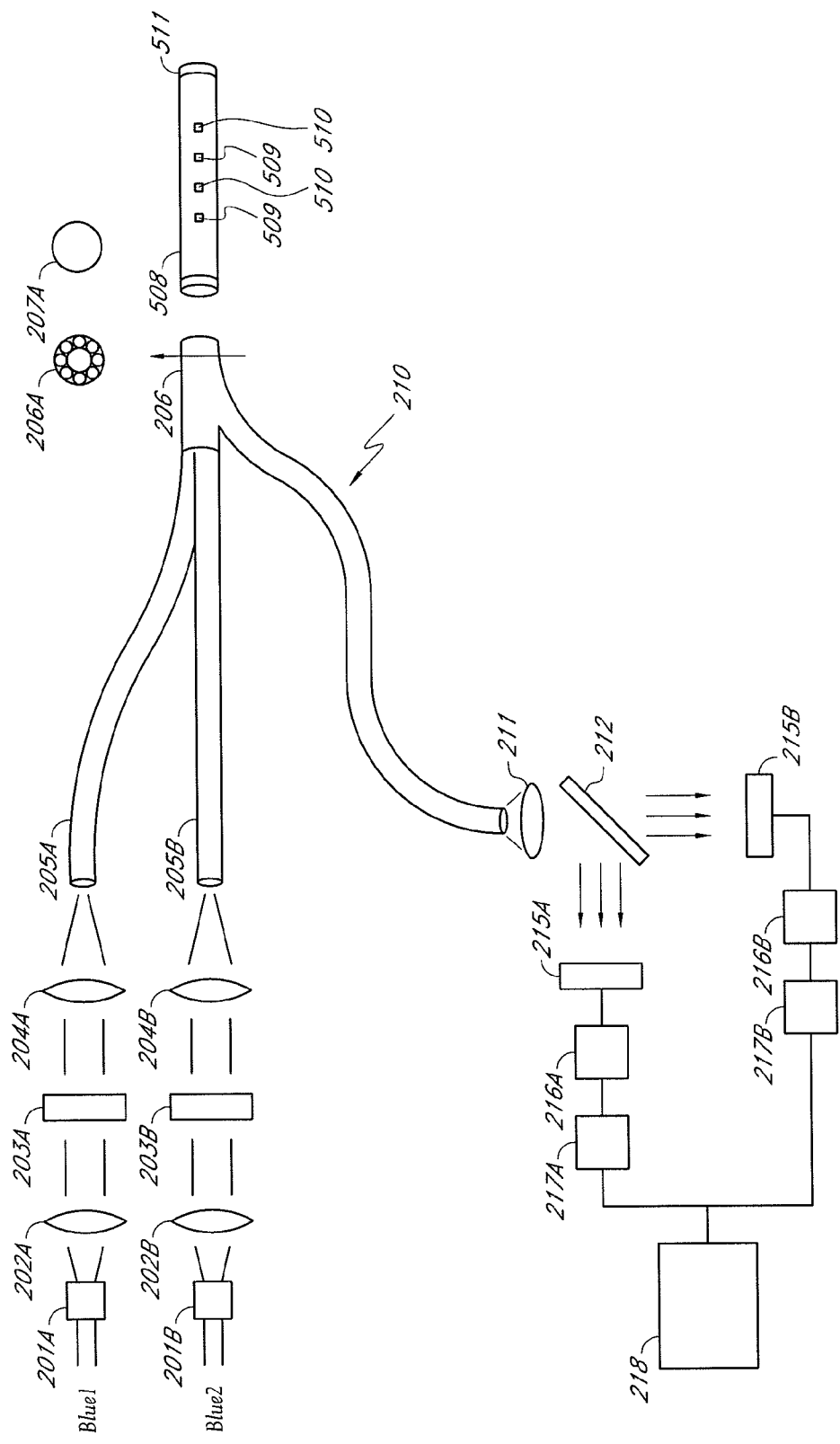
FIG. 6 is an illustration depicting a glucose measurement system embodiment comprising two excitation light sources, two fluorophore systems, two detectors, and a beam splitter.
Figure 6A:
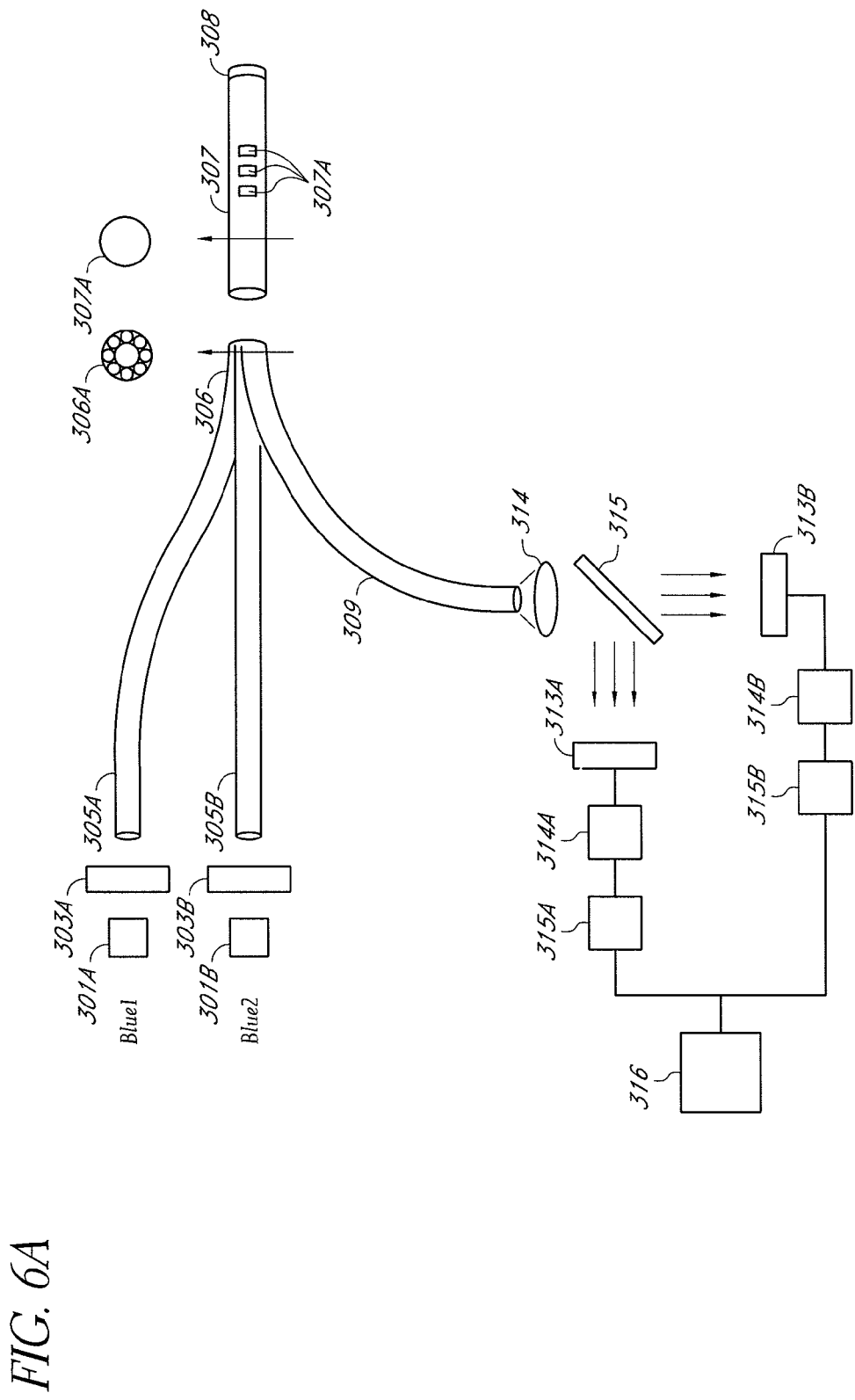
FIG. 6a is an illustration depicting a glucose measurement system embodiment comprising two excitation light sources wherein the fiber acts as a spatial filter.

System where Both the Collimating and Focusing Lens can be Eliminated by Using the Spatial Filtering Characteristics of the Optical Fiber—Specifically the Numerical Aperture—to Only Allow Light Passing Through the Filter within a Defined Angle of Incidence Range to Enter the Fiber With reference to all of the foregoing systems described above, in certain embodiments, the light transmitted from the light sources does not travel through an optical module comprising a collimator lens, an interference filter, and a focusing lens before being transmitted through the glucose sensor. Instead, as shown in FIG. 6A for example, the optical module comprises only the interference filters, 303A and 303B, which block the portion of spectrum that overlaps with the emission wavelength, are disposed between the light source and optical fibers. The collimator and focusing lenses are not used in this embodiment. In such embodiments, the optical fiber itself is used as a spatial filter. The light source can attach to an interference filter, which is attached to an optical fiber that acts as a spatial filter (as shown in FIG. 6A). By selecting an optical fiber having a certain acceptance angle or a numerical aperture, the optical fiber restricts the angle of light allowed to enter the optical fiber. The use of the optical fiber as a spatial filter is advantageous for several reasons. There are fewer pieces to assemble when using only the optical fiber as a spatial filter as oppose to using a collimator lens, a focusing lens, and a housing to house these components. The use of the optical fiber as a spatial filter is also less expensive than using a collimator lens, and a focusing lens. The amount of light coupled into the fiber by using the optical fiber as a spatial filter is substantially the same as the amount of light coupled into the fiber by using a collimator lens, and a focusing lens.

With reference to all of the foregoing systems described above, in certain embodiments, the interference filter may be replaced with other types of filters, for example, wratten filters.

The indicator system (also referred to herein as a fluorophore system) can comprise a fluorophore operably coupled to a quencher. In certain embodiments, the fluorophore system comprises a polymer matrix comprising a fluorophore susceptible to quenching by a viologen, a viologen quencher with quenching efficacy dependent on glucose concentration, and a glucose permeable polymer, wherein said matrix is in contact with blood in vivo. Preferably the fluorophore is a fluorescent organic dye, the quencher is a boronic acid functionalized viologen, and the matrix is a hydrogel.

Fluorophores

"Fluorophore" refers to a substance that when illuminated by light at a particular wavelength emits light at a longer wavelength; i.e. it fluoresces. Fluorophores include but are not limited to organic dyes, organometallic compounds, metal chelates, fluorescent conjugated polymers, quantum dots or nanoparticles and combinations of the above. Fluorophores may be discrete moieties or substituents attached to a polymer.

Fluorophores that may be used in preferred embodiments are capable of being excited by light of wavelength at or greater than about 400 nm, with a Stokes shift large enough that the excitation and emission wavelengths are separable by at least 10 nm. In some embodiments, the separation between the excitation and emission wavelengths may be equal to or greater than about 30 nm. These fluorophores are preferably susceptible to quenching by electron acceptor molecules, such as viologens, and are resistant to photo-bleaching. They are also preferably stable against photo-oxidation, hydrolysis and biodegradation.

In some embodiments, the fluorophore may be a discrete compound.

In some embodiments, the fluorophore may be a pendant group or a chain unit in a water-soluble or water-dispersible polymer having molecular weight of about 10,000 daltons or greater, forming a dye-polymer unit. In one embodiment, such dye-polymer unit may also be non-covalently associated with a water-insoluble polymer matrix $M^1$ and is physically immobilized within the polymer matrix $M^1$, wherein $M^1$ is permeable to or in contact with analyte solution. In another embodiment, the dye on the dye-polymer unit may be negatively charged, and the dye-polymer unit may be immobilized as a complex with a cationic water-soluble polymer, wherein said complex is permeable to or in contact with the analyte solution. In one embodiment, the dye may be one of the polymeric derivatives of hydroxypyrene trisulfonic acid. The polymeric dyes may be water-soluble, water-swellable or dispersible in water. In some embodiments, the polymeric dyes may also be cross-linked. In preferred embodiments, the dye has a negative charge.

In other embodiments, the dye molecule may be covalently bonded to the water-insoluble polymer matrix $M^1$, wherein said $M^1$ is permeable to or in contact with the analyte solution. The dye molecule bonded to $M^1$ may form a structure $M^1$-$L^1$-Dye. $L^1$ is a hydrolytically stable covalent linker that covalently connects the sensing moiety to the polymer or matrix. Examples of $L^1$ include lower alkylene (e.g., $C_1$-$C_8$ alkylene), optionally terminated with or interrupted by one or more divalent connecting groups selected from sulfonamide (—$SO_2NH$—), amide —(C=O)N—, ester —(C=O)—O—, ether. —O—, sulfide —S—, sulfone (—$SO_2$—), phenylene —$C_6H_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like, or a combination thereof. In one embodiment, the dye is bonded to a polymer matrix through the sulfonamide functional groups.

In some embodiments, useful dyes include pyranine derivatives (e.g. hydroxypyrene trisulfonamide derivatives and the like), which have the following formula:

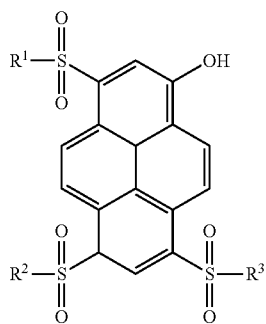

wherein $R^1$, $R^2$, $R^3$ are each —$NHR^4$, $R^4$ is —$CH_2CH_2$(—$OCH_2CH_2$—)$_n X^1$; wherein $X^1$ is —OH, —$OCH_3COOH$, —$CONH_2$, —$SO_3H$, —$NH_2$, or OMe; and n is between about 70 and 10,000. In one embodiment, the dyes may be bonded to a polymer through the sulfonamide functional groups. In other embodiments, the dye may be one of the polymeric derivatives of hydroxypyrene trisulfonic acid.

In some embodiments, the fluorescent dye may be 8-hydroxypyrene-1,3,6-trisulfonate (HPTS). The counterions can be $H^+$ or any other cation. HPTS exhibits two excitation wavelengths at around 450 nm and around 405 nm, which correspond to the absorption wavelengths of the acid and its conjugate base. The shift in excitation wavelength is due to the pH-dependent ionization of the hydroxyl group on HPTS. As the pH increases, HPTS shows an increase in absorbance at about 450 nm, and a decrease in absorbance below about 420 nm. The pH-dependent shift in the absorption maximum enables dual-excitation ratiometric detection in the physiological range. This dye has a molecular weight of less than 500 daltons, so it will not stay within the polymer matrix, but it can be used with an anion exclusion membrane.

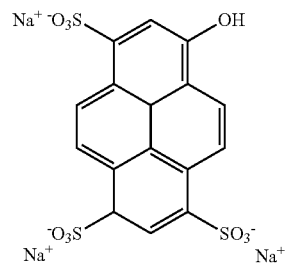

(the $Na^+$ salt of HPTS-"pyranine")

In another embodiment, the fluorescent dye may be polymers of 8-acetoxy-pyrene-1,3,6-N,N',N"-tris-(methacrylpropylamidosulfonamide) (acetoxy-HPTS-MA):

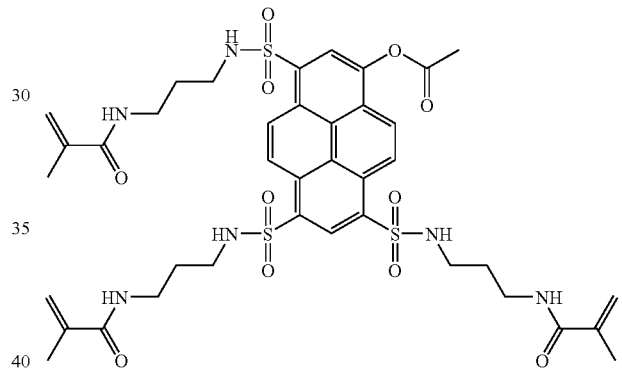

It is noted that dyes such as acetoxy-HPTS-MA (above) having no anionic groups, may not give very strong glucose response when operably coupled to a viologen quencher, particularly a viologen quencher having only a single boronic acid moiety.

In another embodiment, the fluorescent dye may be 8-hydroxy-pyrene-1,3,6-N, N',N"-tris-(carboxypropylsulfonamide) (HPTS-$CO_2$):

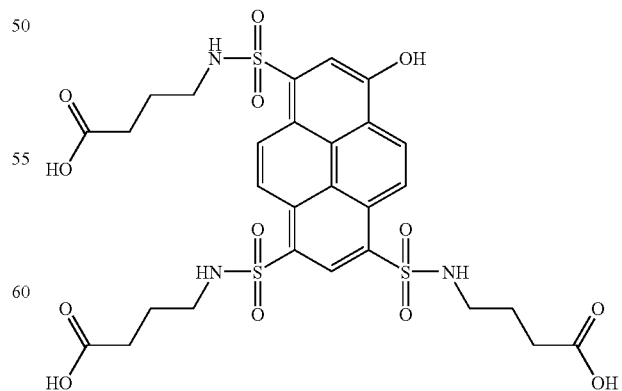

In another embodiment, the fluorescent dye may be 8-hydroxy-pyrene-1,3,6-N, N',N"-tris-(methoxypolyethoxyethyl (~125)sulfonamide) (HPTS-PEG):

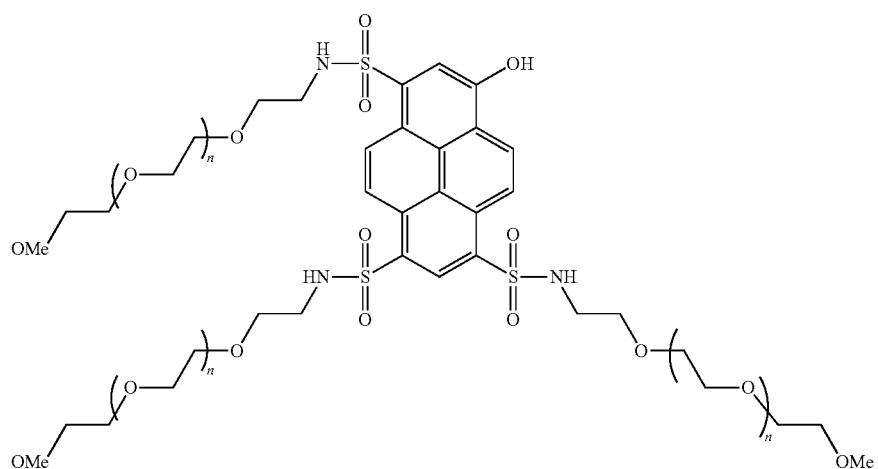

It is noted that dyes such as HPTS-PEG (above) having no anionic groups, may not provide a very strong glucose response when operably coupled to a viologen quencher, particularly a viologen quencher having only a single boronic acid moiety.

Representative dyes as discrete compounds are the tris adducts formed by reacting 8-acetoxypyrene-1,3,6-trisulfonylchloride (HPTS-Cl) with an amino acid, such as amino butyric acid. Hydroxypyrene trisulfonamide dyes bonded to a polymer and bearing one or more anionic groups are most preferred, such as copolymers of 8-hydroxypyrene-1-N-(methacrylamidopropylsulfonamido)-N',N'''-3,6-bis(carboxypropylsulfonamide) HPTS-CO$_2$-MA with HEMA, PEGMA, and the like.

In another embodiment, the fluorescent dye may be HPTS-TriCys-MA:

This dye may be used with a quencher comprising boronic acid, such as 3,3'-oBBV.

Of course, in some embodiments, substitutions other than Cys-MA on the HPTS core are consistent with aspects of the present invention, as long as the substitutions are negatively charged and have a polymerizable group. Either L or D stereoisomers of cysteine may be used. In some embodiments, only one or two of the sulfonic acids may be substituted. Likewise, in variations to HPTS-CysMA shown above, other counterions besides NBu$_4^+$ may be used, including positively charged metals, e.g., Na$^+$. In other variations, the sulfonic acid groups may be replaced with e.g., phosphoric, carboxylic, etc. functional groups.

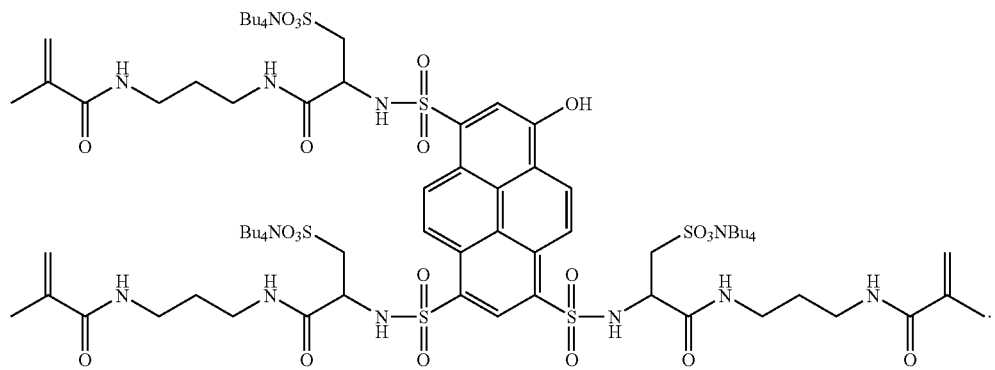

Another suitable dye is HPTS-LysMA, which is pictured below as follows:

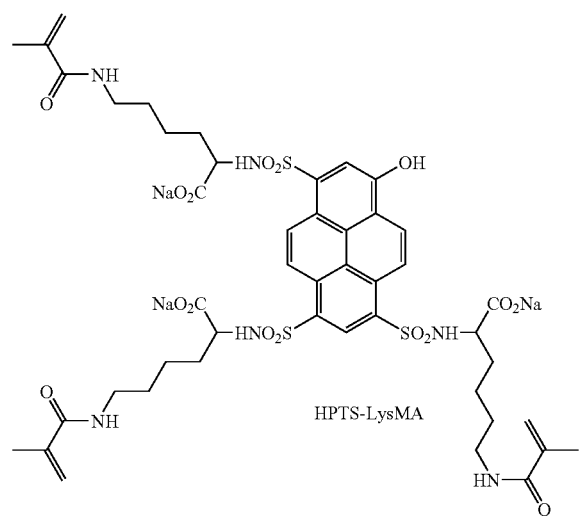

HPTS-LysMA

Other examples include soluble copolymers of 8-acetoxypyrene-1,3,6-N,N', N''-tris(methacrylamidopropylsulfonamide) with HEMA, PEGMA, or other hydrophilic comonomers. The phenolic substituent in the dye is protected during polymerization by a blocking group that can be removed by hydrolysis after completion of polymerization. Such suitable blocking groups, as for example, acetoxy, trifluoroacetoxy, and the like, are well known in the art.

Fluorescent dyes, including HPTS and its derivatives are known and many have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. Nos. 11/296,898, 11/671,880, 11/782,553, and 60/954,204; each of which is incorporated herein in its entirety by reference thereto.

The SNARF and SNAFL dyes from Molecular Probes may also be useful fluorophores in accordance with aspects of the present invention. The structures of SNARF-1 and SNAFL-1 are shown below.

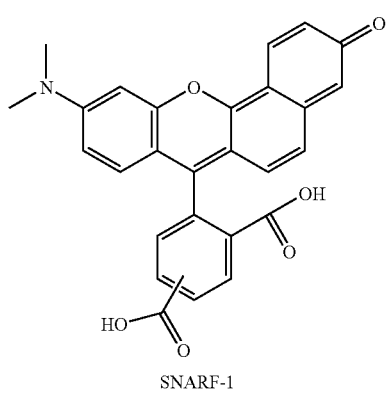

SNARF-1

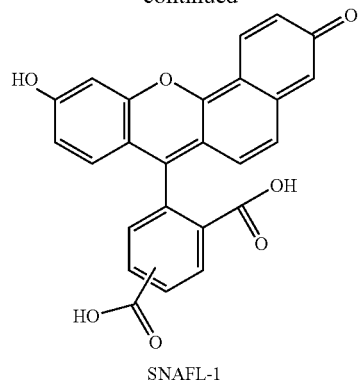

SNAFL-1

Additionally, a set of isomeric water-soluble fluorescent probes based on both the 6-aminoquinolinium and boronic acid moieties which show spectral shifts and intensity changes with pH, in a wavelength-ratiometric and calorimetric manner may be useful in accordance with some embodiments of the present invention (See e.g., Badugu, R. et al. 2005 Talanta 65 (3):762-768; and Badugu, R. et al. 2005 Bioorg. Med. Chem. 13 (1):113-119); incorporated herein in its entirety by reference.

Another example of a fluorescence dye that may be pH and saccharide sensitive is tetrakis(4-sulfophenyl)porphine (TSPP)—shown below. TSPP may not work optimally in blood, where the porphyrin ring may react with certain metal ions, like ferric, and become non-fluorescent.

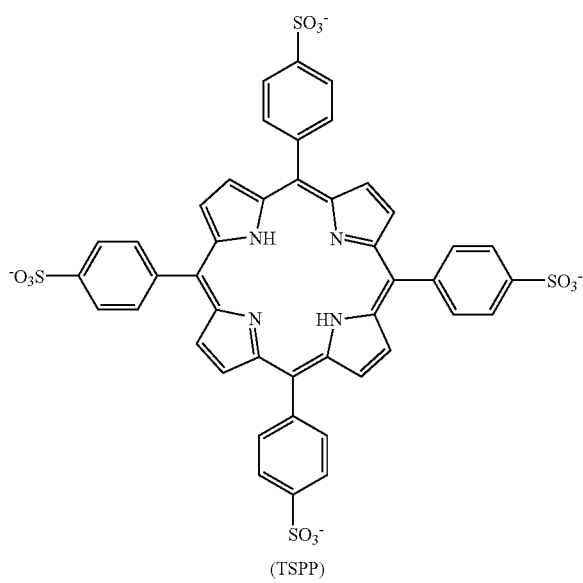

(TSPP)

Additional examples of pH sensitive fluorescent indicators that may be useful for simultaneous determination of pH and glucose in the sensor of the present invention are described in US 2005/0233465 and US 2005/0090014; each of which is incorporated herein by reference in its entirety.

Analyte Binding Moieties—Quenchers

In accordance with broad aspects of the present invention, the analyte binding moiety provides the at least dual functionality of being able to bind analyte and being able to modulate the apparent concentration of the fluorophore (e.g., detected as a change in emission signal intensity) in a manner related to the amount of analyte binding. In preferred embodiments, the analyte binding moiety is associated with a quencher. "Quencher" refers to a compound that reduces the emission of a fluorophore when in its presence. Quencher (Q) is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally crosslinked.

In one example, the moiety that provides glucose recognition in the embodiments is an aromatic boronic acid. The boronic acid is covalently bonded to a conjugated nitrogen-containing heterocyclic aromatic bis-onium structure (e.g., a viologen). "Viologen" refers generally to compounds having the basic structure of a nitrogen containing conjugated N-substituted heterocyclic aromatic bis-onium salt, such as 2,2'-, 3,3'- or 4,4'-N,N' bis-(benzyl) bipyridium dihalide (i.e., dichloride, bromide chloride), etc. Viologen also includes the substituted phenanthroline compounds. The boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the fluorphore by the viologen resulting in an increase in fluorescence dependent on glucose concentration. A useful bis-onium salt is compatible with the analyte solution and capable of producing a detectable change in the fluorescent emission of the dye in the presence of the analyte to be detected.

Bis-onium salts in the embodiments of this invention are prepared from conjugated heterocyclic aromatic di-nitrogen compounds. The conjugated heterocyclic aromatic di-nitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic di-nitrogen compounds in which both nitrogens can be substituted are useful in this invention. In one embodiment, the quencher may be one of the bis-onium salts derived from 3,3'-dipyridyl, 4,4'-dipyridyl and 4,7-phenanthroline.

In some embodiments, the viologen-boronic acid adduct may be a discrete compound having a molecular weight of about 400 daltons or greater. In other embodiments, it may also be a pendant group or a chain unit of a water-soluble or water-dispersible polymer with a molecular weight greater than about 10,000 daltons. In one embodiment, the quencher-polymer unit may be non-covalently associated with a polymer matrix and is physically immobilized therein. In yet another embodiment, the quencher-polymer unit may be immobilized as a complex with a negatively charge water-soluble polymer.

In other embodiments, the viologen-boronic acid moiety may be a pendant group or a chain unit in a crosslinked, hydrophilic polymer or hydrogel sufficiently permeable to the analyte (e.g., glucose) to allow equilibrium to be established.

In other embodiments, the quencher may be covalently bonded to a second water-insoluble polymer matrix $M^2$, which can be represented by the structure $M^2$-$L^2$-Q. $L_2$ is a linker selected from the group consisting of a lower alkylene (e.g., $C_1$-$C_8$ alkylene), sulfonamide, amide, quaternary ammonium, pyridinium, ester, ether, sulfide, sulfone, phenylene, urea, thiourea, urethane, amine, and a combination thereof. The quencher may be linked to $M^2$ at one or two sites in some embodiments.

For the polymeric quencher precursors, multiple options are available for attaching the boronic acid moiety and a reactive group which may be a polymerizable group or a coupling group to two different nitrogens in the heteroaromatic centrally located group. These are:

a) a reactive group on a first aromatic moiety is attached to one nitrogen and a second aromatic group containing at least one —B(OH)2 group is attached to the second nitrogen;

b) one or more boronic acid groups are attached to a first aromatic moiety which is attached to one nitrogen and one boronic acid and a reactive group are attached to a second aromatic group which second aromatic group is attached to the second nitrogen;

c) one boronic acid group and a reactive group are attached to a first aromatic moiety which first aromatic group is attached to one nitrogen, and a boronic acid group and a reactive group are attached to a second aromatic moiety which is attached to the second nitrogen; and d) one boronic acid is attached to each nitrogen and a reactive group is attached to the heteroaromatic ring.

Preferred embodiments comprise two boronic acid moieties and one polymerizable group or coupling group wherein the aromatic group is a benzyl substituent bonded to the nitrogen and the boronic acid groups are attached to the benzyl ring and may be in the ortho-meta or para-positions.

In some embodiments, the boronic acid substituted viologen as a discrete compound useful for in vitro sensing may be represented by one of the following formulas:

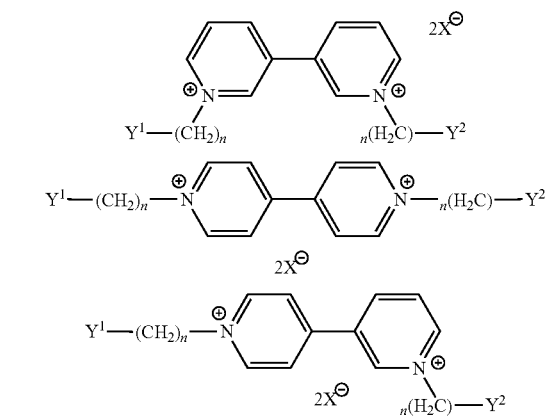

where n=1-3, X is halogen, and $Y^1$ and $Y^2$ are independently selected from phenyl boronic acid (o- m- or p-isomers) and naphthyl boronic acid. In other embodiments, the quencher may comprise a boronic acid group as a substituent on the heterocyclic ring of a viologen.

A specific example used with TSPP is m-BBV:

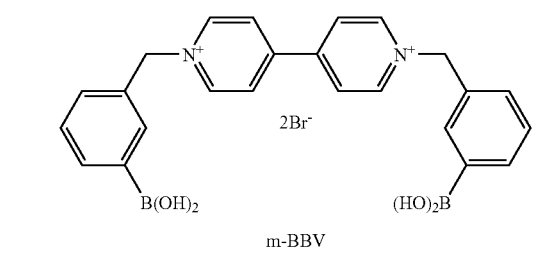

m-BBV

The quencher precursors suitable for making sensors may be selected from the following:
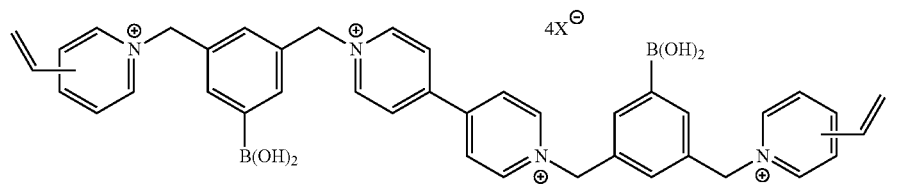
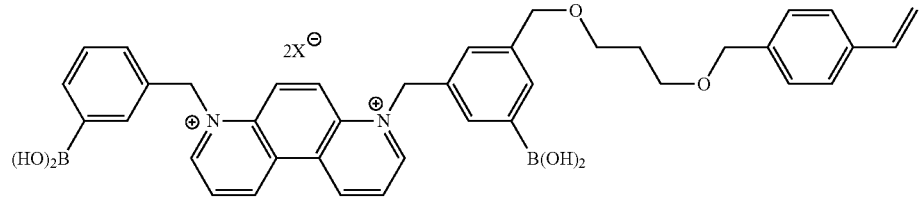
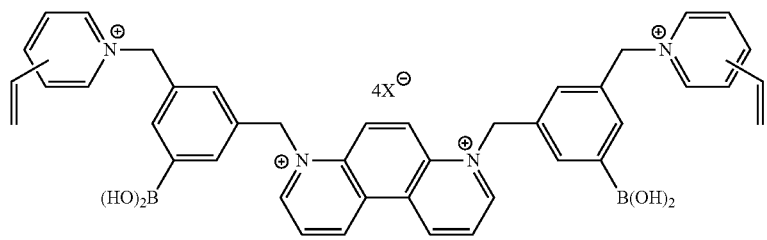
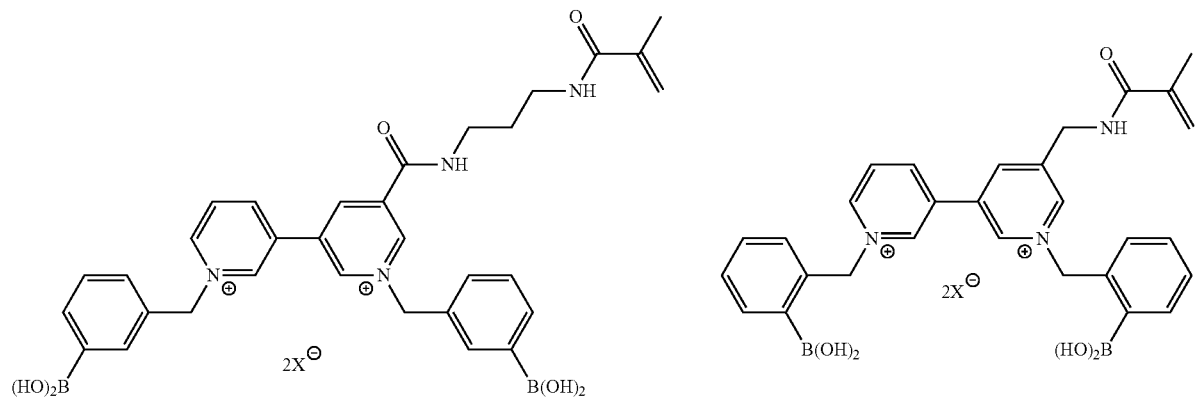
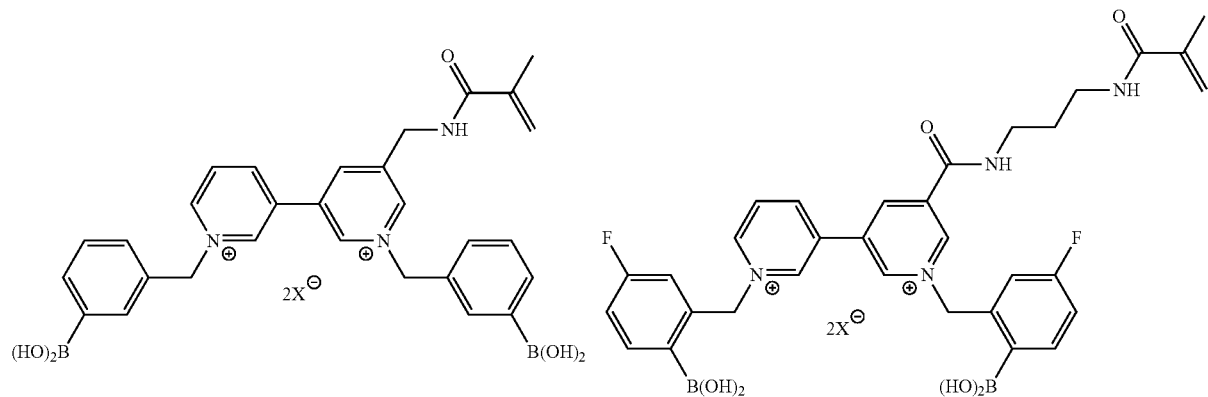

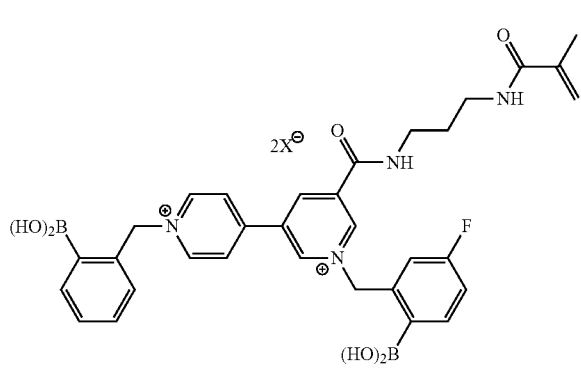

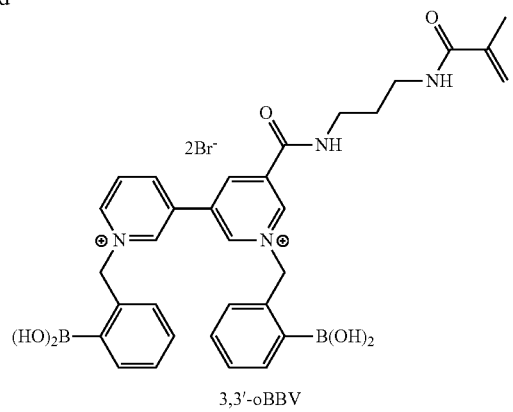

3,3'-oBBV

The quencher precursor 3,3'-oBBV may be used with HPTS-LysMA or HPTS-CysMA to make hydrogels in accordance with preferred aspects of the invention.

Preferred quenchers are prepared from precursors comprising viologens derived from 3,3'-dipyridyl substituted on the nitrogens with benzylboronic acid groups and at other positions on the dipyridyl rings with a polymerizable group or a coupling group. Representative viologens include:

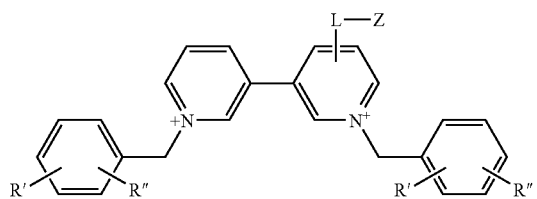

where L is L1 or L2 and is a linking group
Z is a reactive group; and
R' is —B(OH)$_2$ in the ortho- meta- or para-positions on the benzyl ring and R" is H—; or optionally R" is a coupling group as is defined herein or a substituent specifically used to modify the acidity of the boronic acid such as fluoro- or methoxy-L is a divalent moiety that covalently connects the sensing moiety to a reactive group that is used to bind the viologen to a polymer or matrix. Examples of L include those which are each independently selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like.

Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$.

Boronic acid substituted polyviologens are another class of preferred quenchers. The term polyviologen includes: a discrete compound comprised of two or more viologens covalently bonded together by a linking group, a polymer comprised of viologen repeat units in the chain, a polymer with viologen groups pendant to the chain, a dendrimer comprised of viologen units, preferably including viologen terminal groups, an oligomer comprised of viologen units, preferably including viologen endgroups, and combinations thereof. Polymers in which mono-viologen groups form a minor component are not included. The preferred quenchers are water soluble or dispersible polymers, or crosslinked, hydrophilic polymers or hydrogels sufficiently permeable to glucose to function as part of a sensor. Alternatively the polyviologen boronic acid may be directly bonded to an inert substrate.

A polyviologen quencher as a polymer comprised of viologen repeat units has the formula:

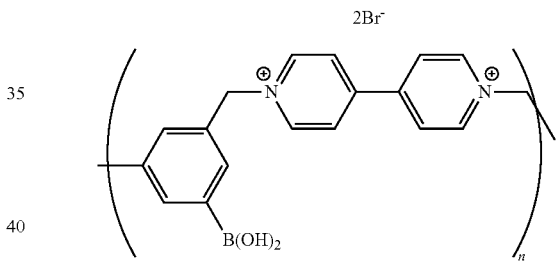

In another embodiment, the polyviologen boronic acid adducts are formed by covalently linking two or more viologen/boronic acid intermediates. The bridging group is typically a small divalent radical bonded to one nitrogen in each viologen, or to a carbon in the aromatic ring of each viologen, or one bond may be to a ring carbon in one viologen and to a nitrogen in the other. Two or more boronic acid groups are attached to the polyviologen. Optionally, the polyviologen boronic acid adduct is substituted with a polymerizable group or coupling group attached directly to the viologen or to the bridging group. Preferably the polyviologen moiety includes only one such group. Preferably, the bridging group is selected to enhance cooperative binding of the boronic acids to glucose.

The coupling moiety is a linking group as defined previously with the proviso that the linking group is optionally further substituted with a boronic acid, a polymerizable group, an additional coupling group, or is a segment in a polymer chain in which the viologen is a chain unit, a pendant group, or any combination thereof.

Glucose-binding quenchers are known and many have been used in analyte detection. See e.g., U.S. Pat. Nos. 6,653,141, 6,627,177 and co-pending U.S. patent application Ser. Nos. 11/296,898, 11/671,880, 11/782,553, 60/915,372 and 60/949,145; each of which is incorporated herein in its entirety by reference thereto.

Immobilizing Means—e.g., Hydrogels

For embodiments that are to be used in vitro, the sensing components are used as individual (discrete) components. The analyte, dye and quencher are mixed together in liquid solution, the change in fluorescence intensity is measured, and the components are discarded. Polymeric matrices which can be used to trap the components to prevent leaching need not be present.

For in vivo applications, the sensor is used in a moving stream of physiological fluid which contains one or more polyhydroxyl organic compounds or is implanted in tissue such as muscle which contains said compounds. Therefore, it is preferred that none of the sensing moieties escape from the sensor assembly. Thus, for use in vivo, the sensing components are preferably part of an organic polymer sensing assembly. Soluble dyes and quenchers can be confined by a semi-permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably the sensing moieties are immobilized in an insoluble polymer matrix, which is freely permeable to glucose. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium. chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is derived from an ethylenically unsaturated derivative of a dye molecule, such as 8-acetoxypyrene-1,3,6-N,N',N"-tris(methacrylamidopropylsulfonamide), the quencher moiety is derived from an ethylenically unsaturated viologen such as 4-N-(benzyl-3-boronic acid)-4'-N'-(benzyl-4ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

In some embodiments, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2 hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

In other embodiments, multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and through complex formation with the fluorophore. In some embodiments, the sensing moieties are immobilized by an insoluble polymer matrix which is freely permeable to polyhydroxyl compounds. Additional details on hydrogel systems have been disclosed in US Patent Publications Nos. US2004/0028612, and 2006/0083688 which are hereby incorporated by reference in their entireties.

The polymer matrix is comprised of organic, inorganic or combinations of polymers thereof. The matrix may be composed of biocompatible materials. Alternatively, the matrix is coated with a second biocompatible polymer that is permeable to the analytes of interest. The function of the polymer matrix is to hold together and immobilize the fluorescent dye and quencher moieties while at the same time allowing contact with the analytes (e.g., polyhydroxyl compounds, $H^+$ and $OH^-$), and binding of the polyhydroxyl compounds to the boronic acid. Therefore, the matrix is insoluble in the medium and in close association with it by establishing a high surface area interface between matrix and analyte solution. The matrix also does not interfere with transport of the analyte to the binding sites so that equilibrium can be established between the two phases. In one embodiment, an ultra-thin film or microporous support matrix may be used. In another embodiment, the matrix that is swellable in the analyte solution (e.g. a hydrogel matrix) can be used for aqueous systems. In some embodiments, the sensing polymers are bonded to a surface such as the surface of a light conduit, or impregnated in a microporous membrane. Techniques for preparing ultra-thin films, microporous polymers, microporous sol-gels, and hydrogels have been established in the prior art.

In one preferred embodiment, the boronic acid substituted viologen may be covalently bonded to a fluorescent dye. The adduct may be a polymerizable compound or a unit in a polymer. One such adduct for example may be prepared by first forming an unsymmetrical viologen from 4,4'-dipyridyl by attaching a benzyl-3-boronic acid group to one nitrogen and an aminoethyl group to the other nitrogen atom. The viologen is condensed sequentially first with 8-acetoxy-pyrene-1,3,6-trisulfonyl chloride in a 1:1 mole ratio followed by reaction with excess PEG diamine to obtain a prepolymer mixture. An acid acceptor is included in both steps to scavenge the byproduct acid. The prepolymer mixture is crosslinked by reaction with a polyisocyanate to obtain a hydrogel. The product is treated with base to remove the acetoxy blocking group. Incomplete reaction products and unreacted starting materials are leached out of the hydrogel by exhaustive extraction with deionized water before further use. The product is responsive to glucose when used as the sensing component as described herein.

Alternatively, such adducts are ethylenically unsaturated monomer derivatives. For example, dimethyl bis-bromomethyl benzene boronate is reacted with excess 4,4'-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with the 8-acetoxypyrene-tris sulfonyl chloride in a 1:1 mole ratio in the presence of an acid acceptor followed by reaction with excess aminopropylmethacrylamide. Finally, any residual amino groups may be reacted with methacrylol chloride. After purification, the dye/viologen monomer may be copolymerized with HEMA and PEGDMA to obtain a hydrogel.

Immobilizing means, e.g., hydrogels, are known and many have been used in analyte detection. See e.g., U.S. Pat. Nos. 6,653,141, 6,627,177 and co-pending U.S. patent application Ser. Nos. 11/296,898, 11/671,880, and 11/782,553; each of which is incorporated herein in its entirety by reference thereto.

Solution Example

Figure 8:
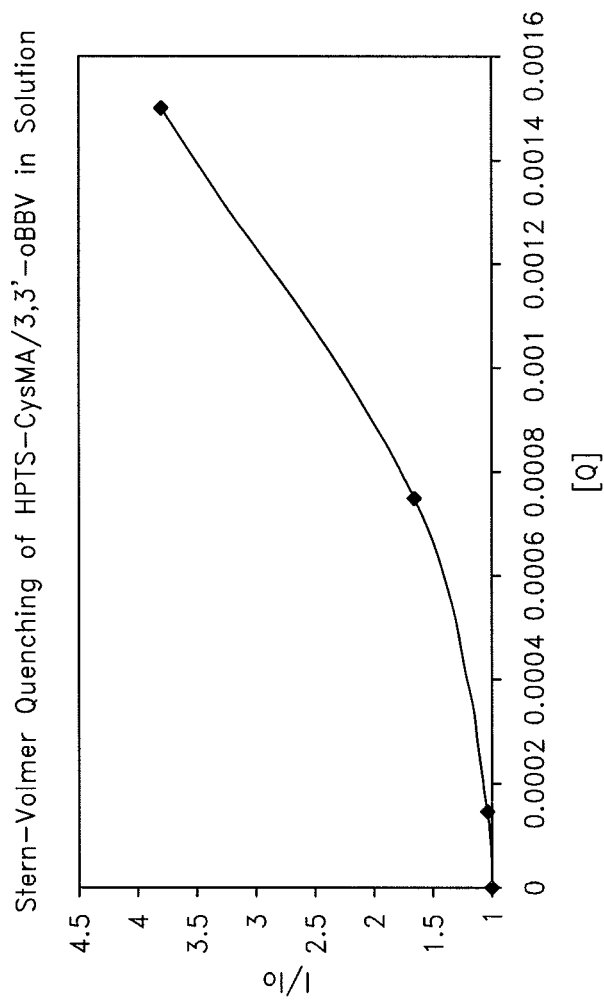
FIG. 8 depicts an embodiment of the Stem-Volmer quenching of HPTS-CysMA/3,3'-oBBV in solution.

To a solution of HPTS-CysMA ($1 \times 10^{-5}$ M in pH 7.4 PBS) was added increasing amounts of 3,3'-oBBV (30 mM in MeOH) and the fluorescence emission measured after each addition. FIG. 8 gives the relative emission change (Stem-Volmer curve) upon addition of 3,3'-oBBV indicating the quenching of HPTS-CysMA with 3,3'-oBBV. The fluorimeter settings were as follows: 1% attenuation, ex slit 8 nm, em slit 12 nm, 486 nm ex λ, 537 nm em λ.

Figure 9:
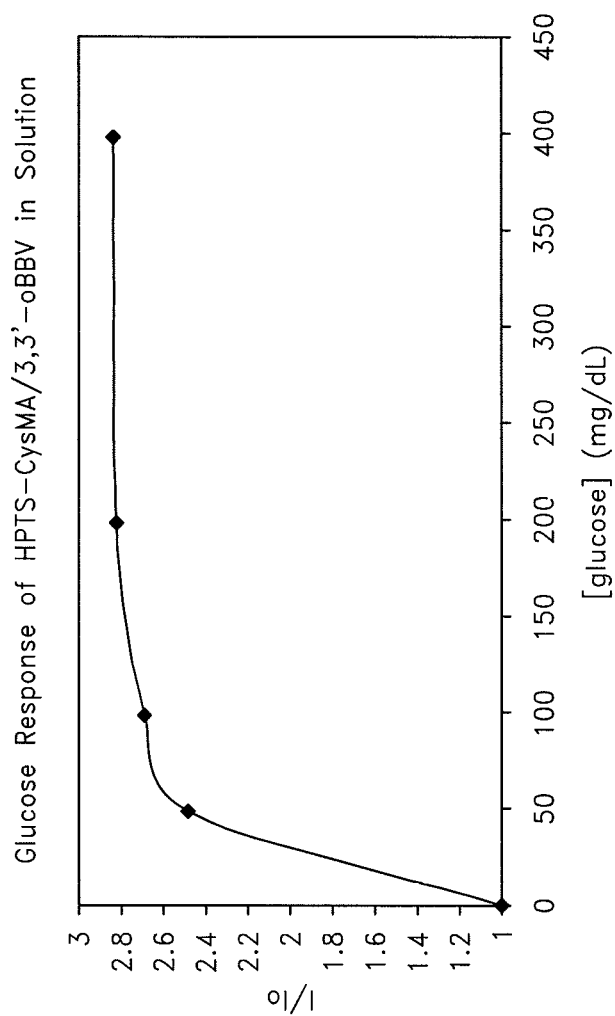
FIG. 9 illustrates the glucose response of HPTS-CysMA/3,3'-oBBV in solution.

HPTS-CysMA ($1 \times 10^{-5}$ M) and 3,3'-oBBV ($3 \times 10^{-3}$ M) were titrated with a stock solution of glucose (31250 mg/dL) in pH 7.4 PBS and the fluorescence emission measured after each addition of glucose The relative change upon addition of glucose is given in FIG. 9.

Hydrogel Example

Figure 10:
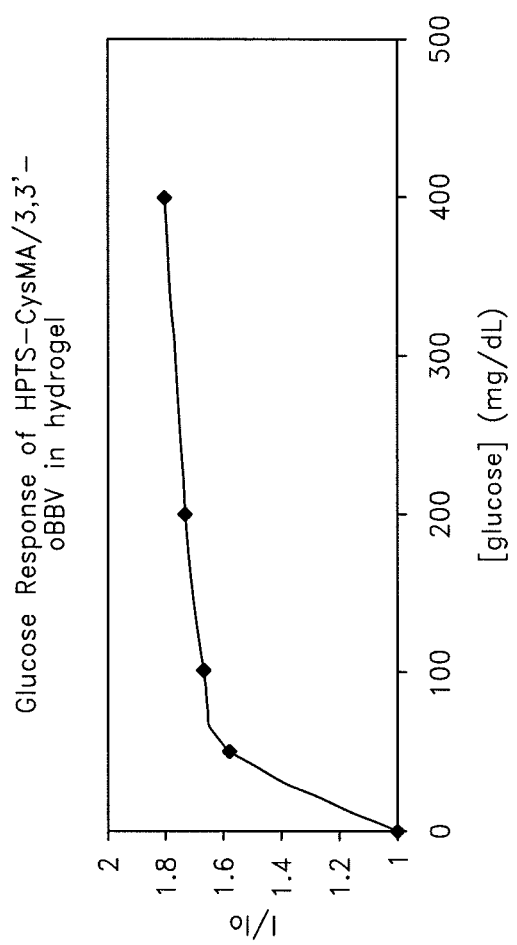
FIG. 10 depicts the glucose response of HPTS-CysMA/3,3'-oBBV in hydrogel.

HPTS-CysMA (2 mg), 3,3'-oBBV (15 mg), N,N'-dimethylacrylamide (400 mg), N,N'-methylenebisacrylamide (8 mg), HCl (10 μL of 1 M solution), and VA-044 (1 mg) were dissolved in water and diluted to 1 mL in a volumetric flask. The solution was freeze-pump-thawed (3×), injected into a mold containing a 0.005" polyimide spacer and polymerized at 55° C. for 16 h. The resultant film was placed in pH 7.4 phosphate buffer and was tested in a flow cell configuration with increasing amounts of glucose (0, 50, 100, 200, 400 mg/dL). The relative fluorescence change upon addition of glucose is given in FIG. 10. The fluorimeter settings were as follows: ex slit 8 nm, em slit 3.5 nm, 515 nm cutoff filter, 486 nm ex λ, 532 nm em λ.

System Information

In certain embodiments, the examples, systems and methods set forth in the foregoing disclosure may be embodied in part or in whole in software that is running on a computing device. The functionality provided for in the components and modules of the computing device may comprise one or more components and/or modules. For example, the computing device may comprise multiple central processing units (CPUs) and a mass storage device, such as may be implemented in an array of servers.

In general, the word "module," as used herein (except where it is used in connection with the optical and light sensitive modules described above), refers to logic embodied in hardware or firmware, or to a collection of software instructions, possibly having entry and exit points, written in a programming language, such as, for example, Java, C or C++. A software module may be compiled and linked into an executable program, installed in a dynamic link library, or may be written in an interpreted programming language such as, for example, BASIC, Perl, Lua, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In certain embodiments, the computing device communicates with one or more databases that store information, including credit data and/or non-credit data. This database or databases may be implemented using a relational database, such as Sybase, Oracle, CodeBase and Microsoft® SQL Server as well as other types of databases such as, for example, a flat file database, an entity-relationship database, and object-oriented database, and/or a record-based database.

In certain embodiments, the computing device is IBM, Macintosh, or Linux/Unix compatible. In certain embodiments, the computing device comprises a server, a laptop computer, a cell phone, a personal digital assistant, a kiosk, or an audio player, for example. In certain embodiment, the computing device includes one or more CPUs, which may each include microprocessors. The computing device may further include one or more memory devices, such as random access memory (RAM) for temporary storage of information and read only memory (ROM) for permanent storage of information, and one or more mass storage devices, such as hard drives, diskettes, or optical media storage devices. In certain embodiments, the modules of the computing are in communication via a standards based bus system, such as bus systems using Peripheral Component Interconnect (PCI), Microchannel, SCSI, Industrial Standard Architecture (ISA) and Extended ISA (EISA) architectures, for example. In certain embodiments, components of the computing device communicate via a network, such as a local area network that may be secured.

The computing is generally controlled and coordinated by operating system software, such as the Unix, VxWorks, Windows 95, Windows 98, Windows NT, Windows 2000, Windows XP, Windows Vista, Linux, SunOS, Solaris, PalmOS, Blackberry OS, or other compatible operating systems or real-time operating systems. In other embodiments, the computing device may be controlled by a proprietary operating system. Conventional operating systems control and schedule computer processes for execution, perform memory management, provide file system, networking, and I/O services, and provide a user interface, such as a graphical user interface ("GUI"), among other things.

The computing device may include one or more commonly available input/output (I/O) devices and interfaces, such as a keyboard, mouse, touchpad, microphone, and printer. Thus, in certain embodiments the computing device may be controlled using the keyboard and mouse input devices, while in another embodiment the user may provide voice commands to the computing device via a microphone. In certain embodiments, the I/O devices and interfaces include one or more display device, such as a monitor, that allows the visual presentation of data to a user. More particularly, a display device provides for the presentation of GUIs, application software data, and multimedia presentations, for example. The computing device may also include one or more multimedia devices, such as speakers, video cards, graphics accelerators, and microphones, for example.

In certain embodiments, the I/O devices and interfaces provide a communication interface to various external devices. For example, the computing device may be configured to communicate with one or more networks, such as any combination of one or more LANs, WANs, a virtual private network (VPN), or the Internet, for example, via a wired, wireless, or combination of wired and wireless, communication links. The network communicates with various computing devices and/or other electronic devices via wired or wireless communication links.

Although the foregoing invention has been described in terms of certain embodiments and examples, other embodiments will be apparent to those of ordinary skill in the art from the disclosure herein. Moreover, the described embodiments have been presented by way of example only, and are not intended to limit the scope of the inventions. Indeed, the novel methods and systems described herein may be embodied in a variety of other forms without departing from the spirit thereof. Accordingly, other combinations, omissions, substitutions and modifications will be apparent to the skilled artisan in view of the disclosure herein. Thus, the present invention is not intended to be limited by the example or preferred embodiments. The accompanying claims provide exemplary claims and their equivalents are intended to cover forms or modifications as would fall within the scope and spirit of the inventions.

What is claimed is:

1. An optical device for determining blood glucose concentration, comprising:

an excitation light source that emits an excitation light signal; a fiber optic sensor optically coupled to the excitation light source through an optical fiber configured as a spatial filter and comprising an indicator system comprising a fluorophore operably coupled to a glucose binding moiety, wherein upon absorption of at least a portion of the excitation light signal, the indicator system emits an emission light signal having an intensity related to the blood glucose concentration; and a light sensitive module operably coupled to at least the fiber optic sensor, wherein the light sensitive module detects the emission light signal and at least a second light signal, wherein the second light signal is derived from the excitation light source or an optional reference light source;

wherein the fiber optic sensor is mechanically coupled to the optical fiber configured as the spatial filter.

2. The optical device of claim 1, further comprising a data processing device configured to determine the blood glucose concentration by performing a ratiometric analysis of the emission light signal and the at least second light signal therein substantially compensating for changes in the optical emission signal intensity unrelated to the blood glucose concentration.

3. The optical device of claim 1, further comprising at least one optical module configured to deliver the excitation light signal and the reference light signal to the fiber optic sensor.

4. The optical device of claim 3, wherein the optical module comprises an interference filter.

5. The optical device of claim 1, further comprising a mode mixing scrambler configured to remove high mode light from at least the excitation light signal.

6. The optical device of claim 1, further comprising a second excitation light source that emits a second excitation light signal at a different wavelength than the first excitation light source.

7. The optical device of claim 6, wherein the fluorophore is excited by the first and second excitation light signals and emits a first and second light signal at the same wavelengths.

8. The optical device of claim 1, wherein the light sensitive module comprises a beam splitter configured to receive at least the emission light signal and the excitation light signal from the fiber optic sensor, wherein the beam splitter is configured to reflect a first portion of light and configured to allow a second portion of light to pass through the beam splitter.

9. The optical device of claim 1, wherein the light sensitive module comprises at least a first detector, a second detector, a first amplifier, a second amplifier, and a first analog to digital converter, and a second analog to digital converter.

10. The optical device of claim 1, wherein the light sensitive module comprises a micro spectrometer.

11. The optical device of claim 1, wherein the fiber optic sensor further comprises a second fluorophore, wherein upon absorption of at least a portion of the excitation light signal, the second fluorophore emits a second emission light signal having an intensity insensitive to at least the blood pH and glucose concentration.

12. The optical device of claim 1, wherein the fiber optic sensor further comprises a dye coated surface that emits a second emission light upon excitation by the excitation light signal.

13. A ratiometric method for correcting an optical measurement of blood glucose concentration for optical artifacts unrelated to the blood glucose concentration, comprising:
providing the optical device of claim 1;
deploying the fiber optic sensor;
actuating the excitation light source therein exciting the indicator system, and optionally actuating the optional reference light source;
detecting the emission light signal and the second light signal; and
correcting the blood glucose concentration, comprising:
calculating a ratio of the emission light signal to the second light signal; and
comparing said ratio with a predetermined function that correlates ratios of emission light signals to second light signals with blood glucose concentrations.

14. The device of claim 1, further comprising a reflective surface.

15. The device of claim 14, wherein the reflective surface is configured to reflect the emission light signal and the excitation light signal through the optical device.

16. The device of claim 14, wherein the reflective surface is a mirror.

17. The device of claim 1, wherein the indicator system is housed within a cavity and is immobilized within a hydrogel which is permeable to glucose in the blood vessel.

18. The device of claim 17, wherein the cavity comprises a geometric design.

19. The device of claim 18, wherein the design of the cavity comprises a plurality of holes in the sensor.

20. The device of claim 19, wherein the plurality of holes are positioned perpendicular to a tangent along a length of the sensor, and wherein the plurality of holes are evenly spaced horizontally and evenly rotated around the sides of the sensor.

21. The device of claim 19, wherein the plurality of holes are positioned at an angle to a tangent along a length of the sensor, and wherein the plurality of holes are evenly spaced horizontally and evenly rotated around the sides of the sensor.

22. The device sensor of claim 18, wherein the design of the cavity comprises a groove along a length of the sensor.

23. The device sensor of claim 22, wherein the groove comprises a depth that extends to the center of the sensor.

24. The device sensor of claim 22, wherein the groove spirals around the length of the sensor.

25. The device sensor of claim 18, wherein the design of the cavity comprises a plurality of sections cut from the sensor.

26. The device sensor of claim 25, wherein the sections form a triangular wedge area that extends to the center of the sensor, and wherein the sections are evenly spaced horizontally and evenly rotated around the sides of the sensor.

27. The device of claim 17, wherein the hydrogel is confined by a semi-permeable membrane that allows passage of glucose and blocks passage of the indicator system.

28. The optical device of claim 1, wherein no collimating or focusing lens is used.

\* \* \* \* \*